(12) United States Patent
Fukagawa et al.

(10) Patent No.: US 8,178,601 B2
(45) Date of Patent: May 15, 2012

(54) POLYMER FILM, POLARIZING PLATE PROTECTIVE FILM, POLARIZING PLATE AND LIQUID CRYSTAL DISPLAY DEVICE

(75) Inventors: Nobutaka Fukagawa, Minami-Ashigara (JP); Masaki Noro, Minami-Ashigara (JP); Teruki Niori, Minami-Ashigara (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 877 days.

(21) Appl. No.: 12/204,438

(22) Filed: Sep. 4, 2008

(65) Prior Publication Data

US 2009/0080074 A1  Mar. 26, 2009

(30) Foreign Application Priority Data

Sep. 7, 2007 (JP) ................................ 2007-232819

(51) Int. Cl.
 *C08K 5/34* (2006.01)
 *F21V 9/06* (2006.01)
(52) U.S. Cl. ........................ 524/100; 359/500
(58) Field of Classification Search .................. 524/100
 See application file for complete search history.

(56) References Cited

U.S. PATENT DOCUMENTS

| 6,712,896 B2 | 3/2004 | Ono et al. | |
| 7,646,457 B2 * | 1/2010 | Fukagawa et al. | 349/122 |
| 2007/0182895 A1 | 8/2007 | Fukagawa et al. | |
| 2007/0184232 A1 * | 8/2007 | Takahashi et al. | 428/64.4 |

FOREIGN PATENT DOCUMENTS

| CN | 1908772 A | | 2/2007 |
| JP | 09240161 A | * | 9/1997 |
| JP | 2002-47357 A | | 2/2002 |
| JP | 2002047357 A | * | 2/2002 |
| JP | 2007-156433 A | | 6/2007 |

OTHER PUBLICATIONS

Translation of JP 2002047357, Feb. 2002.*
Translation of JP 09240161, Sep. 1997.*
Office Action from the State Intellectual Property Office of the People's Republic of China issued in corresponding Chinese Patent Application No. 200810212575.4 dated Jun. 24, 2011, with an English translation.

* cited by examiner

*Primary Examiner* — Ling Choi
*Assistant Examiner* — Hui Chin
(74) *Attorney, Agent, or Firm* — Buchanan Ingersoll & Rooney PC

(57) ABSTRACT

A polymer film includes: a wavelength dispersion regulator represented by formula (I):

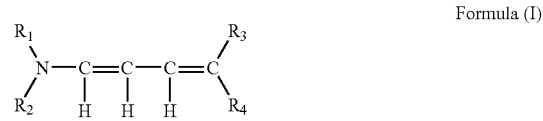

Formula (I)

wherein $R_1$ and $R_2$ each independently represents a hydrogen atom, an alkyl group or an aryl group, provided that both $R_1$ and $R_2$ are not hydrogen atoms at the same time; and $R_3$ and $R_4$ each independently represents an electron-withdrawing substituent, and $R_1$ and $R_2$, or $R_3$ and $R_4$ may be bonded together to form a ring, and wherein the polymer film has a retardation value that satisfies the following formulae (1) and (2):

$70 \text{ nm} \leq Rth(548) \leq 300 \text{ nm}$   Formula (1)

$Rth(628) < Rth(548) < Rth(446)$   Formula (2)

wherein $Rth(\lambda)$ represents a retardation value expressed in nm in a film thickness direction measured at a wavelength of $\lambda$ nm.

9 Claims, 1 Drawing Sheet

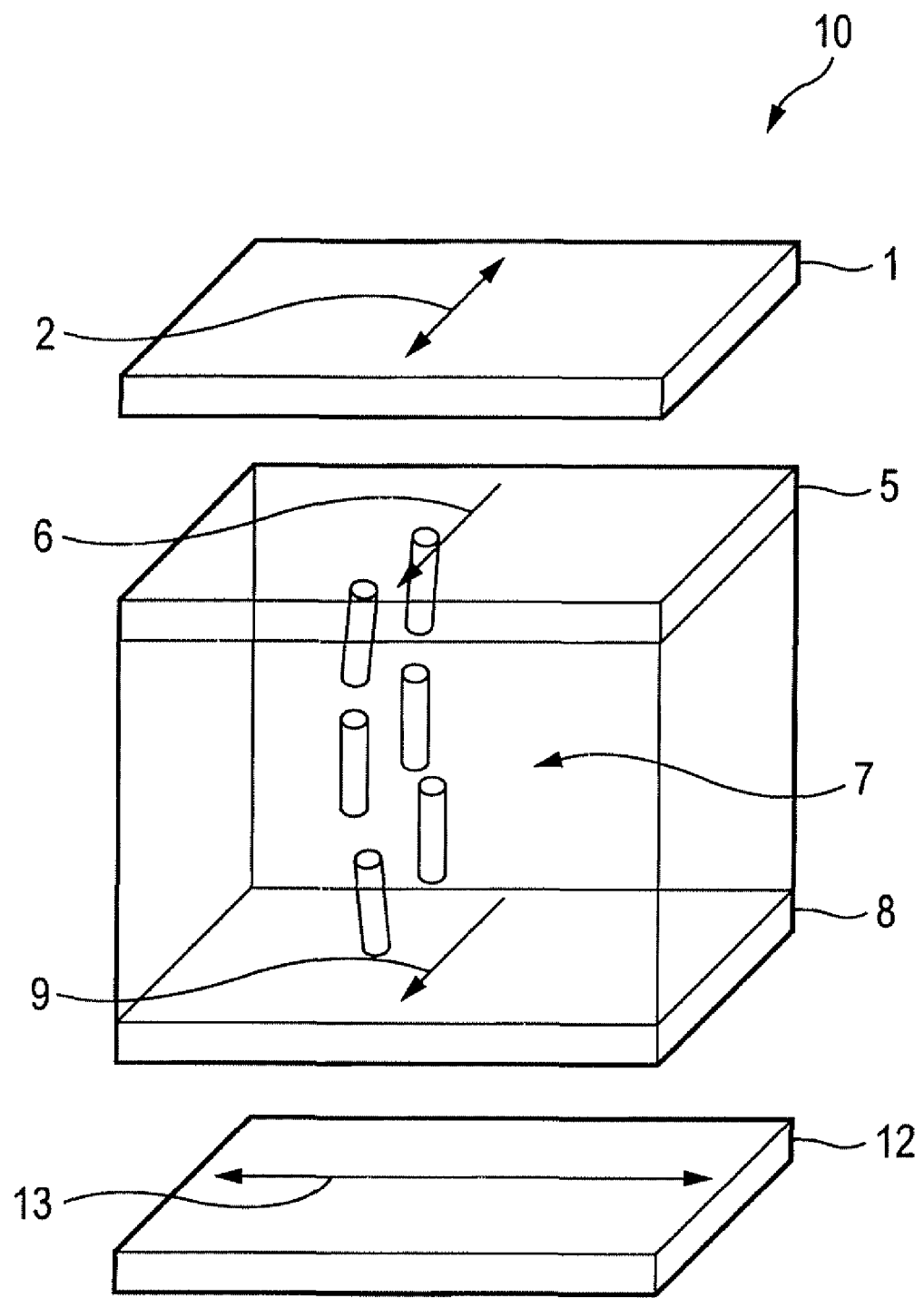

POLYMER FILM, POLARIZING PLATE PROTECTIVE FILM, POLARIZING PLATE AND LIQUID CRYSTAL DISPLAY DEVICE

BACKGROUND OF THE INVENTION

1. Field of the Invention

The present invention relates to a liquid crystal display device, and, in particular, to a VA mode liquid crystal display device excellent in the viewing angle property and a polymer film etc, to be used in the display device.

2. Description of the Related Art

The application of liquid crystal display devices has been increasing year by year as electric-power saving and space-saving image display devices. The existing liquid crystal display devices have a large defect of having large viewing angle dependency of images. In the recent years, however, a wide viewing angle liquid crystal mode has been put into practical use, which brings about a rapid increase in the demand of liquid crystal display devices even in a market of, for example, televisions with a need for high grade images.

Although VA mode liquid crystal display devices are advantageous in showing high contrast in general compared with devices having other liquid crystal display modes, they suffer from such problem that the contrast and hue largely change depending on the viewing angle.

To solve this problem, optically compensatory films having various optical properties and methods for combining the same have been proposed hitherto. Among all, there is a highly promising method comprising combining an optically compensatory film in which the in-plane retardation (hereinafter referred to as Re) becomes smaller at a shorter wavelength (hereinafter referred to as inverse dispersion) with another optically compensatory film in which the retardation in the thickness direction (hereinafter referred to as Rth) becomes larger at a shorter wavelength (hereinafter referred to as normal dispersion). For example, JP-A-2007-156433 discloses a method wherein a stretched cellulose acylate film is used as an optically compensatory film with inverse dispersion while a film having a polyimide layer formed on a tack is used as an optically compensatory film with normal dispersion. Although use of such a film having a polyimide layer formed on a tack is an effective way for obtaining an optically compensatory film with normal dispersion, it costs high because of the double-layered structure.

To improve weatherability of polymer films such as cellulose acylate films, on the other hand, there has been known a method of adding an additive having an absorption in the ultraviolet wavelength region (hereinafter referred to as a UV absorber). As the UV absorber, a colorless compound showing an absorption band in the ultraviolet region of as long wavelength as possible is preferred. JP-A-2002-47357 discloses a cellulose acylate film containing a compound having a structure wherein an amino group is attached to one end of a butadiene structure and an electron-withdrawing group is added to the other end thereof (hereinafter referred to as an aminobutadiene compound). However, the aminobutadiene compound is liable to be degraded after prolonged photo-irradiation and, therefore, further improvement is still required. Moreover, JP-A-2002-47357 refers nothing to the use of an aminobutadiene compound for controlling the retardation, in particular, controlling the wavelength dependency of the retardation in the thickness direction.

In the case of adding an aminobutadiene compound to a cellulose acetate film, in particular, bleed-out frequently occurs. As a result, there arises a problem that the compound can be added only in a limited amount and, therefore, retardation cannot be sufficiently controlled. Thus, it has been required to overcome this problem.

SUMMARY OF THE INVENTION

An object of the present invention is to provide a polymer film for providing a liquid crystal display device which has a high oblique contrast, a low dependency on viewing angle of tint and an excellent light-fastness and in which the occurrence of bleed-out is regulated.

As the results of intensive studies, the present inventors have found out that the photostability of an aminobutadiene compound can be largely improved by adding a triazine compound having proton acceptability, thereby completing the invention. They have further found out that the above-described triazine compound having proton acceptability is also effective in regulating bleed-out of the aminobutadiene compound. The present inventors furthermore have found out that use of a cellulose acetate propionate having acetyl groups and propionyl groups wherein the acetyl substitution degree and the propionyl substitution degree satisfy a definite range makes it possible to obtain wavelength dispersion of a desired retardation without causing bleed-out, thereby completing the present invention.

Accordingly, the above-described problems have been solved by the following means.

(1) A polymer film, comprising:
a wavelength dispersion regulator represented by formula (I):

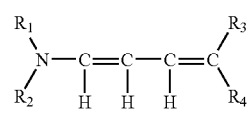

Formula (I)

wherein $R_1$ and $R_2$ each independently represents a hydrogen atom, an alkyl group or an aryl group, provided that both $R_1$ and $R_2$ are not hydrogen atoms at the same time; and $R_3$ and $R_4$ each independently represents an electron-withdrawing substituent, and $R_1$ and $R_2$, or $R_3$ and $R_4$ may be bonded together to form a ring, and wherein the polymer film has a retardation value that satisfies the following formulae (1) and (2):

$$70 \text{ nm} \leq Rth(548) \leq 300 \text{ nm} \quad \text{Formula (1)}$$

$$Rth(628) < Rth(548) < Rth(446) \quad \text{Formula (2)}$$

wherein $Rth(\lambda)$ represents a retardation value expressed in nm in a film thickness direction measured at a wavelength of $\lambda$ mm.

(2) The polymer film as described in (1) above, further comprising:
a light-fastness improving agent represented by formula (II):

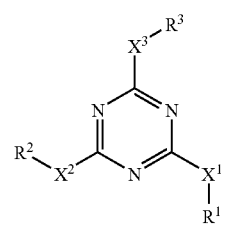

Formula (II)

wherein $X^1$ represents —$NR^4$—, —O— or —S—;
$X^2$ represents —$NR^5$—, —O— or —S—;
$X^3$ represents —$NR^6$—, —O— or —S—;
$R^1$, $R^2$ and $R^3$ each independently represents an alkyl group, an alkenyl group, an aryl group or a heterocyclic group; and
$R^4$, $R^5$ and $R^6$ each independently represents a hydrogen atom, an alkyl group, an alkenyl group, an aryl group or a heterocyclic group.

(3) The polymer film as described in (1) or (2) above, comprising:
a cellulose acylate.

(4) The polymer film as described in (3) above,
wherein the cellulose acylate contains acetyl groups and propionyl groups, and
when a substitution degree of acetyl groups is A and a substitution degree of propionyl groups is P, the acetyl substitution degree A and the propionyl substitution degree P satisfy the following formulae (3) and (4):

$$2.00 \leq A+P \leq 2.70 \qquad \text{Formula (3)}$$

$$(3-A<P) \times 0.5 \leq P \leq (3-A-P) \times 2. \qquad \text{Formula (4)}$$

(5) The polymer film as described in (3) or (4) above, which contains 1.0 to 20% by mass of the wavelength dispersion regulator represented by formula (I) based on the cellulose acylate.

(6) The polymer film as described in any of (2) to (5) above, which contains 10% by mass or more but not more than 1000% by mass of the light-fastness improving agent represented by formula (II) based on the wavelength dispersion regulator represented by formula (I).

(7) The polymer film as described in any of (1) to (6) above wherein the wavelength dispersion regulator represented by formula (I) is a compound represented by formula (I-2):

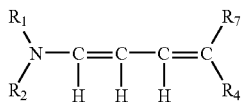

Formula (I-2)

wherein $R_1$, $R_2$ and $R_4$ are each as defined in formula (I); and
$R_7$ represents —$COOR_5$ or —$SO_2R_5$, in which $R_5$ represents a hydrogen atom or a substituent, (8) A polarizing plate protective film, comprising:
the polymer film as described in any of (1) to (7) above.

(9) A polarizing plate, comprising:
a polarizer; and
a protective film that is provided in at least one side of the polarizer,
wherein the protective film is the polarizing plate protective film as described in (8) above.

(10) A liquid crystal display device, comprising:
a liquid crystal cell; and
the polarizing plate as described in (9) above.

BRIEF DESCRIPTION OF THE DRAWING

FIG. 1 is a schematic view which shows an exemplary example of the liquid crystal display device according to an aspect of the invention,
wherein 1 denotes upper polarizing plate, 2 denotes absorption axis direction of upper polarizing plate, 5 denotes upper electrode substrate of liquid crystal cell, 6 denotes alignment control direction of upper substrate, 7 denotes liquid crystal layer, 8 denotes lower electrode substrate of liquid crystal cell, 9 denotes alignment control direction of lower substrate, 10 denotes liquid crystal display device, 12 denotes lower polarizing plate and 13 denotes absorption axis direction of lower polarizing plate.

DETAILED DESCRIPTION OF THE INVENTION

Hereinafter, the content of the invention will be described in greater detail. Incidentally, the expression "n to m" as used herein means including numerals n and m as the lower limit and the upper limit, respectively.
The polymer film according to the invention comprises a wavelength dispersion regulator represented by the formula (I) and has retardation that satisfies the following formulae (1) and (2):

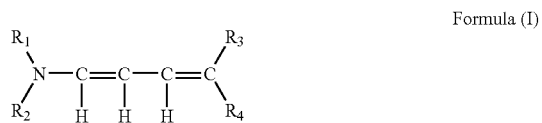

Formula (I)

wherein $R_1$ and $R_2$ each independently represents a hydrogen atom, an alkyl group or an aryl group, provided that both $R_1$ and $R_2$ are not hydrogen atoms at the same time; and $R_3$ and $R_4$ each independently represents an electron-withdrawing substituent, or $R_1$ and $R_2$, or $R_3$ and $R_4$ may be bonded together to form a ring;

$$70 \text{ nm} \leq Rth(548) \leq 300 \text{ nm} \qquad \text{Formula (1)}$$

$$Rth(628)<Rth(548)<Rth(446) \qquad \text{Formula (2)}$$

wherein Rth(λ) represents the retardation (expressed in nm) in the film thickness direction that is measured at a wavelength of λ nm.
First, the wavelength dispersion regulator represented by the formula (I) will be described in detail.

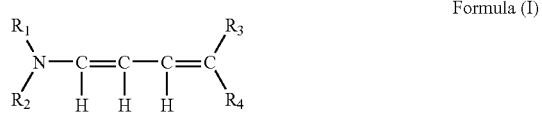

Formula (I)

In the formula (I), $R_1$ and $R_2$ each independently represents a hydrogen atom, an alkyl group or an aryl group, provided that both $R_1$ and $R_2$ are not hydrogen atoms at the same time. $R_3$ and $R_4$ each independently represents an election-withdrawing substituent. $R_1$ and $R_2$ or $R_3$ and $R_4$ may be bonded together to form a ring.
The alkyl group in $R_1$ and $R_2$ is preferably an alkyl group having 1 to 20 carbon atoms and optionally having an unsaturated bond in its carbon chain. Examples thereof include a methyl group, an ethyl group, a butyl group, an n-hexyl group, a cyclohexyl group, an n-decyl group, an n-dodecyl group, an n-octadecyl group, an eicosyl group, a methoxyethyl group, an ethoxypropyl group, a 2-ethylhexyl group, a hydroxyethyl group, a chloropropyl group, an N,N-diethylpropyl group, a cyanoethyl group, a phenethyl group, a pentyl group, a p-t-butylphenethyl group, a p-t-octylphenoxyethyl group, a 3-(2,4-di-tert-amylphenoxy)propyl group, an ethoxycarbonylmethyl group, a 2-(2-hydroxyethoxy)ethyl group, a 2-furylethyl group and so on. It may be further substituted by an alkyl group or aryl group having 1 to 20 carbon atoms.

The aryl group in $R_1$ and $R_2$ is preferably an aryl group having 6 to 20 carbon atoms. Examples thereof include a tolyl group, a phenyl group, an anisyl group, a mesityl group, a chlorophenyl group, a 2,4-di-tert-amylphenyl group, a naphthyl group and so on. It may be further substituted by an alkyl group or aryl group having 1 to 20 carbon atoms.

Both of $R_1$ and $R_2$ are not hydrogen atoms at the same time.

Further, $R_1$ and $R_2$ may be bonded together to form a ring. In this case, they represent groups required for forming a cyclic amino group (for example, a piperidino group, a morpholino group, a pyrrolidino group, a hexahydroazepino group, piperadino group and so on).

$R_3$ and $R_4$ each independently represents an electron-withdrawing substituent. The "electron-withdrawing substituent" as referred to herein means a group whose Hammett's substituent constant σp value is larger than 0. A substituent having a Hammett's substituent constant σp value larger than 0.1 is preferred and a substituent having a Hammett's substituent constant σp value larger than 0.3 is still preferred. In particular, one selected from among —$COR_5$, —$CO_2R_6$, —$CONR_5R_6$, a carboxyl group, a cyano group, —$SO_2R_5$ or —$SO_2NR_5R_6$ is preferable.

$R_5$ and $R_6$ each independently represents a hydrogen atom or a substituent, or $R_5$ and $R_6$ may be bonded to each other to form a ring.

It is preferable that the substituent in $R_5$ is an alkyl group having 1 to 20 carbon atoms, a substituted or unsubstituted cycloalkyl group having 3 to 20 carbon atoms, a substituted or unsubstituted alkenyl group having 2 to 20 carbon atoms, a substituted or unsubstituted aryl group having 6 to 20 carbon atoms, or a substituted or unsubstituted 5- or 6-membered, aromatic or non-aromatic heterocyclic group. More preferably, it is an alkyl group having 1 to 15 carbon atoms, a substituted or unsubstituted cycloalkyl group having 3 to 15 carbon atoms, or a substituted or unsubstituted alkenyl group having 2 to 15 carbon atoms. Still preferably, it is an alkyl group having 1 to 10 carbon atoms, a substituted or unsubstituted cycloalkyl group having 3 to 10 carbon atoms, or a substituted or unsubstituted alkenyl group having 2 to 10 carbon atoms.

It is preferable that the substituent in $R_6$ is a hydrogen atom, an alkyl group having 1 to 10 carbon atoms, a substituted or unsubstituted cycloalkyl group having 3 to 10 carbon atoms, a substituted or unsubstituted alkenyl group having 2 to 10 carbon atoms, a substituted or unsubstituted aryl group having 6 to 10 carbon atoms or a substituted or unsubstituted 5- or 6-membered, aromatic or non-aromatic heterocyclic group. More preferably, it is a hydrogen atom, an alkyl group having 1 to 8 carbon atoms, a substituted or unsubstituted cycloalkyl group having 3 to 8 carbon atoms, or a substituted or unsubstituted alkenyl group having 2 to 8 carbon atoms Still preferably, it is a hydrogen atom, an alkyl group having 1 to 4 carbon atoms or a substituted or unsubstituted alkenyl group having 2 to 4 carbon atoms.

About the Hammett's substituent constant up, detailed description are given by, for example, Inamoto Naoki, *Hammett Soku—Kozo to Hannosei (Hammett's Rule—Structure and Reactivity—)*, (Maruzen); The Chemical Society of Japan Ed., *Shin Jikkenkagaku Koza* 14, *Yukikagobutsu no Gosei to Hannou V (New Course of Experimental Chemistry 14, Synthesis and Reaction of Organic Compound V)*, p. 2605 (Maruzen); Nakaya Tadao, *Riron Yukikagaku Kaisetsu (Interpretation of Theoretical Organic Chemistry)*, p, 217 (TOKYO KAGAKU DOJIN); and Chemical Review vol. 91, pp. 165 to 195 (1991).

Further, $R_3$ and $R_4$ may be bonded together to form a ring. As the ring formed in this case, a 5- or 6-membered carbon ring or heterocyclic ring is preferred. Preferable examples of the carbon ring include 1,3-cyclohexanedione, 1,3-cyclopentanedione and indanedione. Preferable examples of the heterocylic ring include 2-pyrazolin-5-one, rhodamine, hydantoin, thiohydantoin, 2,4-oxazolidinedione, isoxazolone, barbituric acid, thiobarbituric acid, 6-alkoxy-5H-pyrimidine-2,4-dione, dioxopyrazolopyridine, hydroxypyridine, pyrazolidinedione, 2,5-dihydrofuran-2-one, and pyrrolin-2-one, though the invention is not restricted thereto Such a ring may have a substituent.

Furthermore, it may be a compound having a plural number of aminobutadiene skeletons via any of the substituents represented by $R_1$ to $R_6$.

Among the compounds represented by the formula (I), a compound represented by the following formula (I-2) is most preferable.

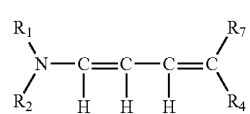

Formula (I-2)

In the formula (I-2), $R_1$, $R_2$ and $R_4$ are each as defined in the formula (I). $R_7$ represents —$COOR_5$ or —$SO_2R_5$ wherein $R_5$ is as defined in the formula (I).

In the above formula (I-2), the substituents $R_1$ to $R_7$ may further have a substituent. Examples of the substituent include a hydroxyl group, a halogen atom (for example, Cl, Br, F or I), a cyano group, a nitro group, a carboxyl group, a sulfo group, a chain or cyclic alkyl group having 1 to 8 carbon atoms (for example, methyl, ethyl, isopropyl, n-butyl, n-hexyl, cyclopropyl, cyclohexyl, 2-hydroxyethyl, 4-carboxybutyl, 2-methoxyethyl, 2-diethylaminoethyl), an alkenyl group having 1 to 8 carbon atoms (for example, vinyl, allyl, 2-hexenyl), an alkynyl group having 2 to 8 carbon atoms (for example, ethynyl, 1-butynyl, 3-hexynyl), an aralkyl group having 7 to 12 carbon atoms (for example, benzyl, phenethyl), an aryl group having 6 to 10 carbon atoms (for example, phenyl, naphthyl, 4-carboxyphenyl, 4-acetamidophenyl, 3-methanesulfonamidophenyl, 4-methoxyphenyl, 3-carboxyphenyl, 3,5-dicarboxyphenyl, 4-methanesulfonamidophenyl, 4-butanesulfonamidophenyl), an acyl group having 1 to 10 carbon atoms (for example, acetyl, benzoyl, propanoyl, butanoyl), an alkoxycarbonyl group having 2 to 10 carbon atoms (for example, methoxycarbonyl, ethoxycarbonyl), an aryloxycarbonyl group having 7 to 12 carbon atoms (for example, phenoxycarbonyl, naphthoxycarbonyl), a carbamoyl group having 1 to 10 carbon atoms (for example, unsubstituted carbamoyl, methylcarbamoyl, diethylcarbamoyl, phenylcarbamoyl), an alkoxy group having 1 to 8 carbon atoms (for example, methoxy, ethoxy, butoxy, methoxyethoxy), an aryloxy group having 6 to 12 carbon atoms (for example, phenoxy, 4-carboxyphenoxy, 3-methylphenoxy, naphthoxy), an acyloxy group having 2 to 12 carbon atoms (for example, acetoxy, benzoyloxy), a sulfonyloxy group having 1 to 12 carbon atoms (for example, methylsulfonyloxy, phenylsulfonyloxy), an amino group having 0 to 10 carbon atoms (for example, unsubstituted amino, dimethylamino, diethylamino, 2-carboxyethylamino), an acylamino group having 1 to 10 carbon atoms (for example, acetamido, benzamido), a sulfonylamino group having 1 to 8 carbon atoms (for example, methylsulfonylamino, phenylsulfonylamino, butylsulfonylamino, n-octylsulfonylamino), a ureido group having 1 to 10 carbon atoms (for example, ureido, methylureido), a urethane group having 2 to 10 carbon atoms (for example, methoxycarbonylamino, ethoxycarbonylamino), an alkylthio group having 1 to 12 carbon atoms (for example, methylthio, ethylthio, octylthio), an arylthio group having 6 to 12 carbon atoms (for example, phenylthio, naphthylthio), an alkylsulfonyl group having 1 to 8 carbon atoms (for example, methylsulfonyl, butylsulfonyl), an arylsulfonyl group having 7 to 12 carbon atoms (for example, phenylsulfonyl, 2-naphthylsulfonyl), a sulfamoyl group having 0 to 8 carbon atoms (for example, unsubstituted sulfamoyl, methylsulfanoyl, etc.) a heterocyclic group (for example, 4-pyridyl, piperidino, 2-furyl, furfuryl, 2-thienyl, 2-pyrrolyl, 2-quinolylmorpholino) and so on.

Next, specific examples of the compound represented by the formula (I) as described above will be presented.

Now, typical examples of the compound represented by the formula (I) as described above will be presented, though the invention is not restricted thereto.

Wavelength Dispersion Regulator 1

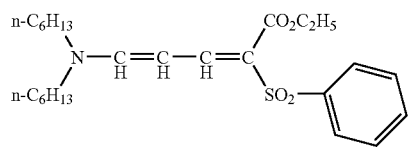

Wavelength Dispersion Regulator 2

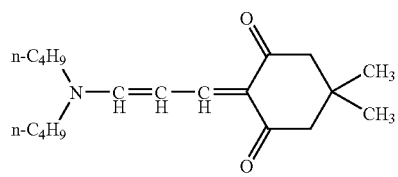

Wavelength Dispersion Regulator 3

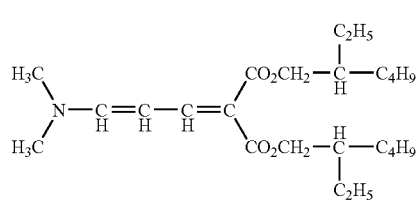

Wavelength Dispersion Regulator 4

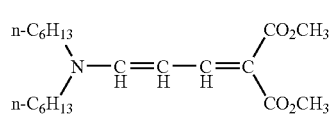

Wavelength Dispersion Regulator 5

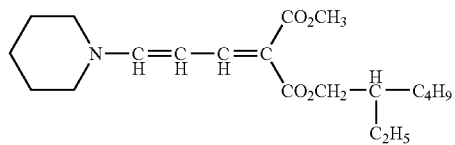

Wavelength Dispersion Regulator 6

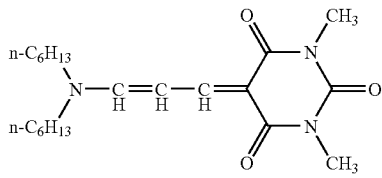

Wavelength Dispersion Regulator 7

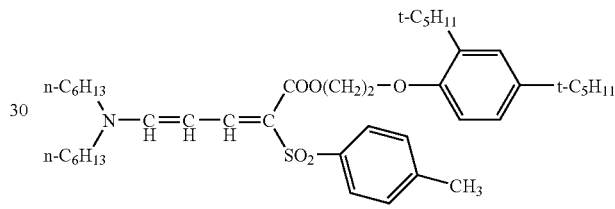

Wavelength Dispersion Regulator 8

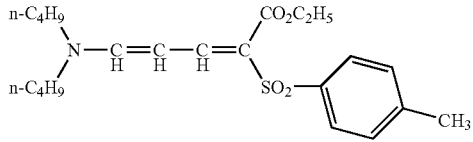

Wavelength Dispersion Regulator 9

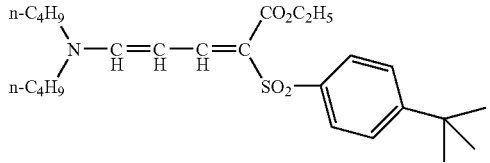

Wavelength Dispersion Regulator 10

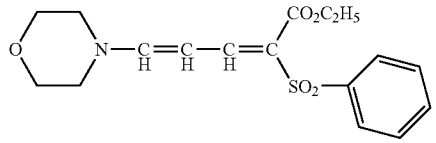

Wavelength Dispersion Regulator 11

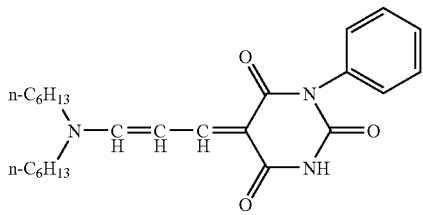

Wavelength Dispersion Regulator 12

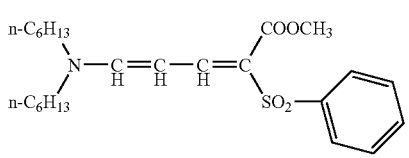

Wavelength Dispersion Regulator 13

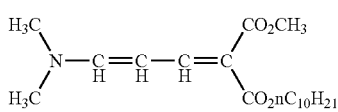

Wavelength Dispersion Regulator 14

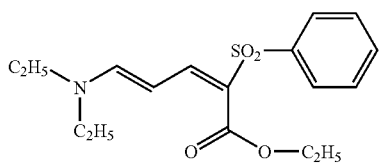

Wavelength Dispersion Regulator 15

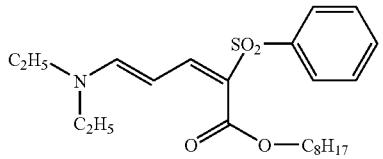

Wavelength Dispersion Regulator 16

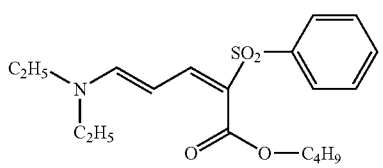

Wavelength Dispersion Regulator 17

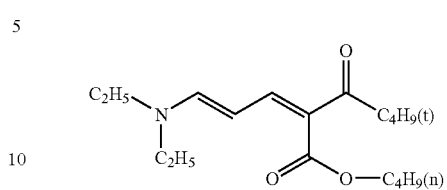

Wavelength Dispersion Regulator 18

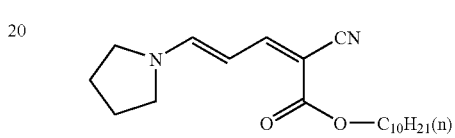

Wavelength Dispersion Regulator 19

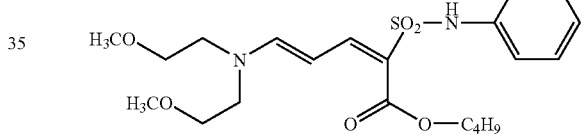

Wavelength Dispersion Regulator 20

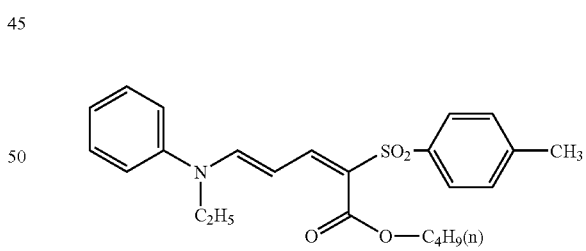

Wavelength Dispersion Regulator 21

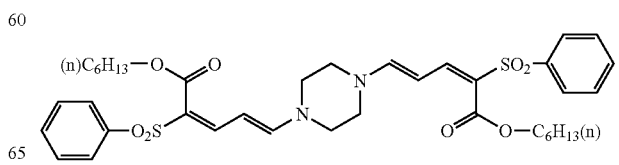

Wavelength Dispersion Regulator 22

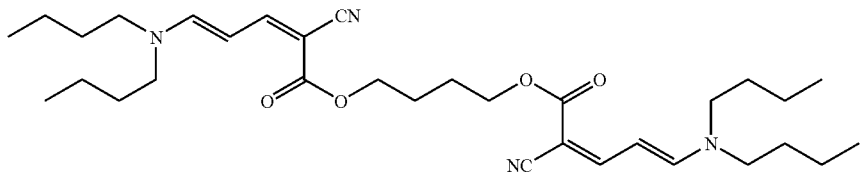

It is preferable that the polymer film according to the invention further comprises a light-fastness improving agent represented by the formula (II).

Next, the light-fastness improving agent represented by the following formula (II) will be described in detail.

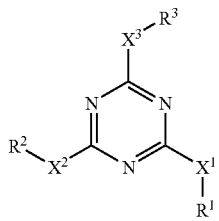

Formula (II)

In the formula (II), $X^1$ represents —$NR^4$—, —O— or —S—; $X^2$ represents —$NR^5$—, —O— or —S—; $X^3$ represents —$NR^6$—, —O— or —S—; $R^1$, $R^2$ and $R^3$ each represents an alkyl group, an alkenyl group, an aryl group or a heterocyclic group; and $R^4$, $R^5$ and $R^6$ each represents a hydrogen atom, an alkyl group, an alkenyl group, an aryl group or a heterocyclic group.

In the formula (II), $R^1$, $R^2$ and $R^3$ each independently represents an alkyl group, an alkenyl group, an aromatic ring group or a heterocyclic group and an aromatic ring group or a heterocyclic group is more preferable. As an aromatic group represented by each of $R^1$, $R^2$ and $R^3$, phenyl or naphthyl is preferable and phenyl is particularly preferable.

$R^1$, $R^2$ and $R^3$ may have a substituent in the aromatic ring or heterocyclic ring. Examples of the substituent include a halogen atom, a hydroxyl group, a cyano group, a nitro group, a carboxyl group, an alkyl group, an alkenyl group, an aryl group, an alkoxy group, an alkenyloxy group, an aryloxy group, an acyloxy group, an alkoxycarbonyl group, an alkenyloxycarbonyl group, an aryloxycarbonyl group, a sulfamoyl group, an alkyl-substituted sulfamoyl group, an alkenyl-substituted sulfamoyl group, an aryl-substituted sulfamoyl group, a sulfonamido group, a carbamoyl group, an alkyl-substituted carbamoyl group, an alkenyl-substituted carbamoyl group, an aryl-substituted carbamoyl group, an amido group, an alkylthio group, an alkenylthio group, an arylthio group and an acyl group.

In the case where $R^1$, $R^2$ and $R^3$ each represents a heterocyclic group, it is preferable that the heterocyclic group has aromatic properties A heterocyclic ring having aromatic properties is generally an unsaturated heterocyclic ring and preferably a heterocyclic ring having as many double bonds as possible. As the heterocyclic ring, a 5-membered ring, a 6-membered ring or a 7-membered ring is preferable, a 5-membered ring or a 6-membered ring is more preferable and a 6-membered ring is most preferable. As the hetero atom in the heterocyclic ring, a nitrogen atom, a sulfur atom or an oxygen atom is preferable, and a nitrogen atom is particularly preferable. As such a heterocyclic ring having aromatic properties, a pyridine ring (2-pyridyl or 4-pyridyl as a heterocyclic group) is particularly preferable. The heterocyclic group may have a substituent. Examples of the substituent are the same as those cited above. The substituent may be further substituted by a substituent as described above.

The alkyl group represented by each of $R^4$, $R^5$ and $R^6$ may be either a cyclic alkyl group or a chain alkyl group. A chain alkyl group is preferable and a linear chain alkyl group is preferred to a branched chain alkyl group. The alkyl group has preferably 1 to 30 carbon atoms, more preferably 1 to 20, more preferably 1 to 10, more preferably 1 to 8 and most preferably 1 to 6 carbon atoms. The alkyl group may have a substituent. Examples of the substituent include a halogen atom, an alkoxy group (for example, methoxy, ethoxy) and an acyloxy group (for example, acryloyloxy, methacryloyloxy).

The alkenyl group represented by each of $R^4$, $R^5$ and $R^6$ may be either a cyclic alkenyl group or a chain alkenyl group A chain alkenyl group is preferable and a linear chain alkenyl group is preferred to a branched chain alkenyl group. The alkenyl group has preferably 2 to 30 carbon atoms, more preferably 2 to 20, more preferably 2 to 10, more preferably 2 to 8 and most preferably 2 to 6 carbon atoms. The alkenyl group may have a substituent. Examples of the substituent include those cited above as the substituent of the alkyl group.

The aromatic ring (aryl) group and heterocyclic group represented by each of $R^4$, $R^5$ and $R^6$ are the same as the aromatic ring group and heterocyclic group represented by each of $R^1$, $R^2$ and $R^3$ and the preferred scope is also the same. The aromatic ring group and heterocyclic group may have a substituent. Examples of the substituent include those cited above as the substituent of the aromatic ring group and heterocyclic group of $R^1$, $R^2$ and $R^3$.

Next, preferable example of the compound represented by the formula (II) in the invention will be presented, though the invention is not restricted to these specific examples.

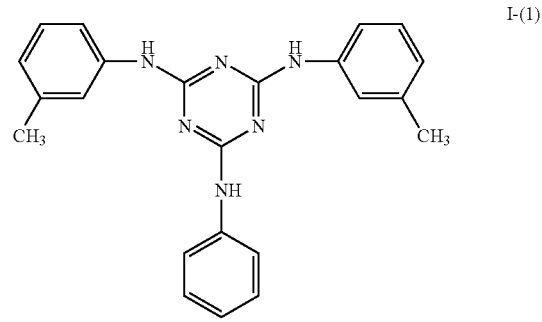

I-(1)

-continued
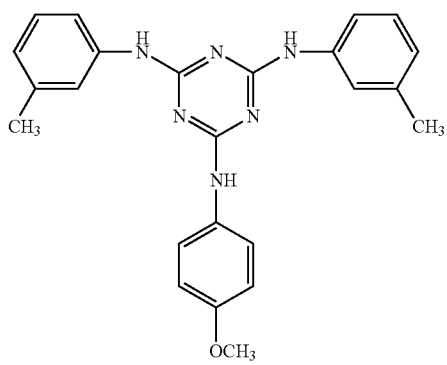
I-(2)
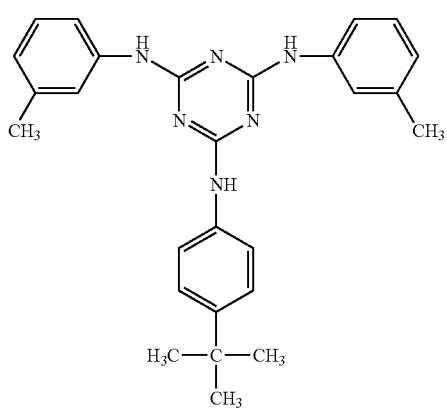
I-(3)
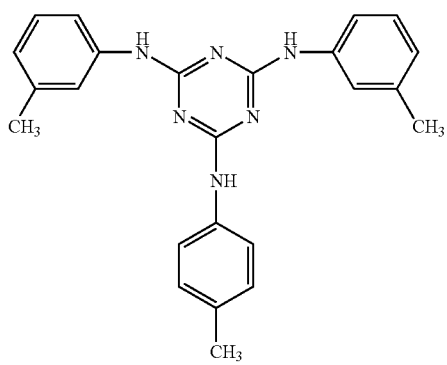
I-(4)
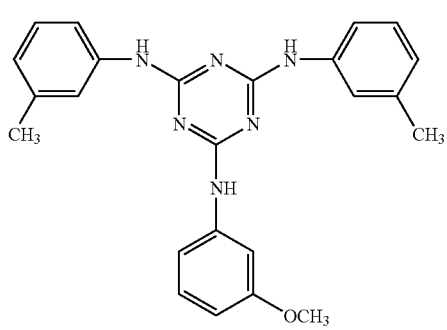
I-(5)
-continued
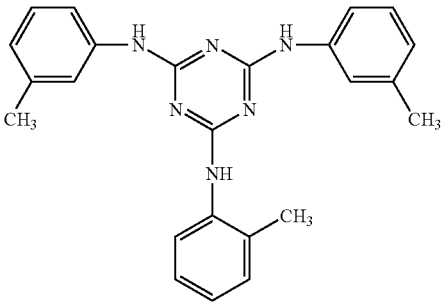
I-(6)
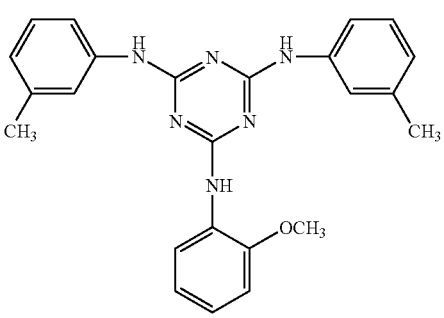
I-(7)
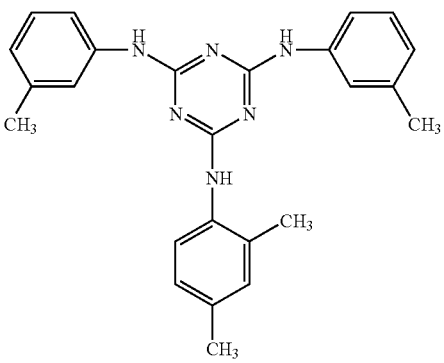
I-(8)
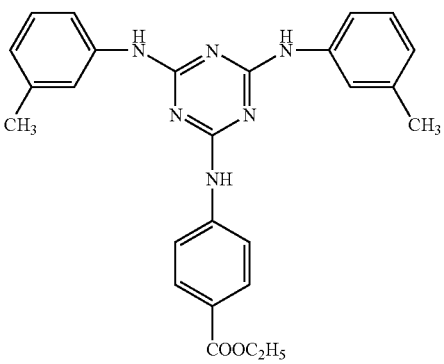
I-(9)
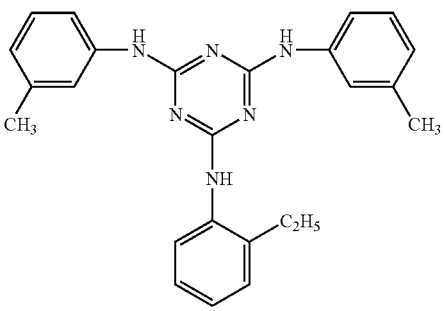
I-(10)

-continued
I-(11)
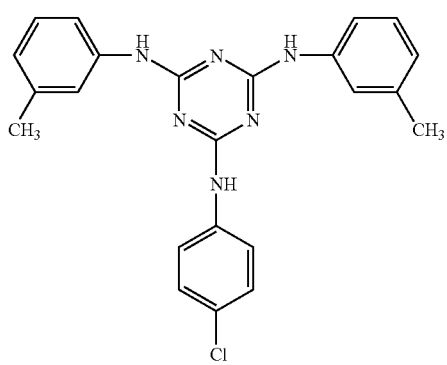
I-(12)
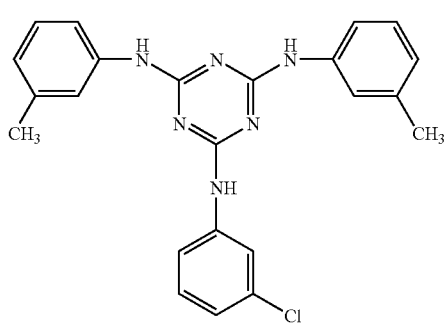
I-(13)
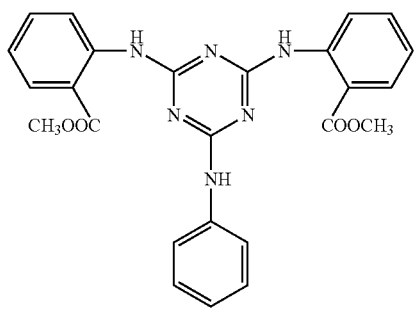
I-(14)
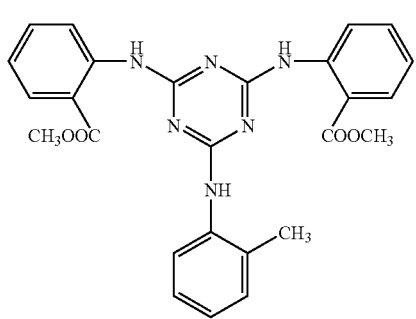
I-(15)
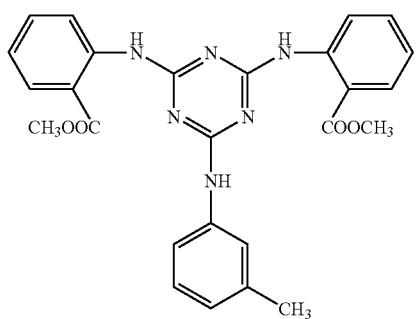
I-(16)
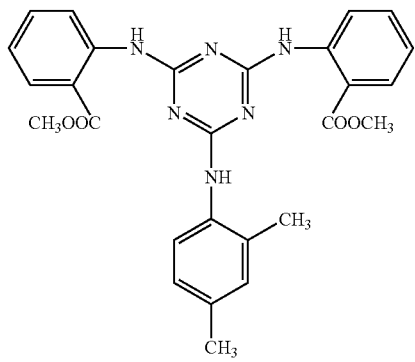
I-(17)
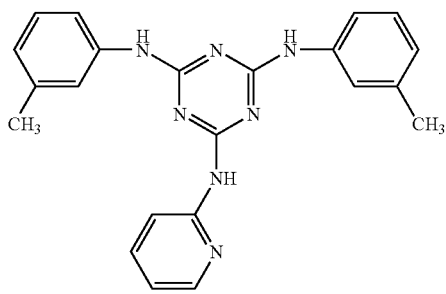
I-(18)
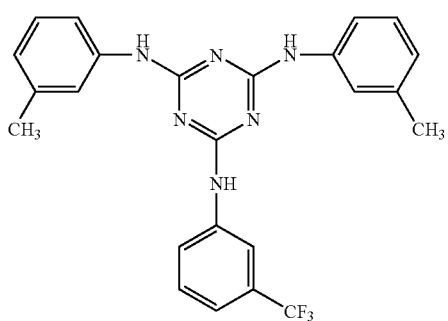
I-(19)
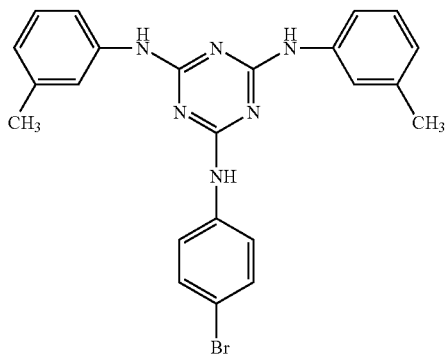
I-(20)
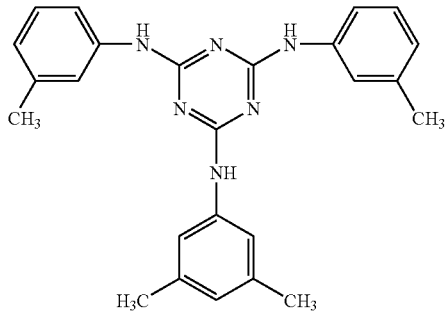

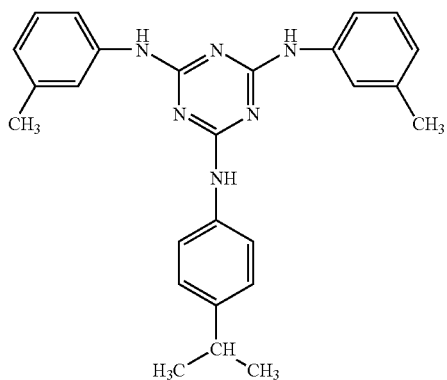
I-(21)
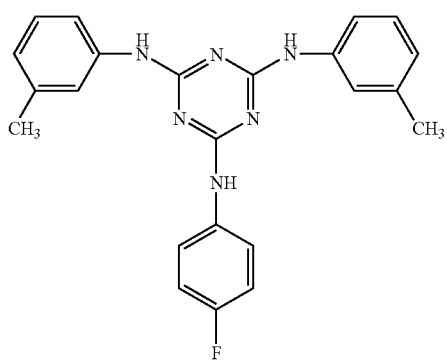
I-(22)
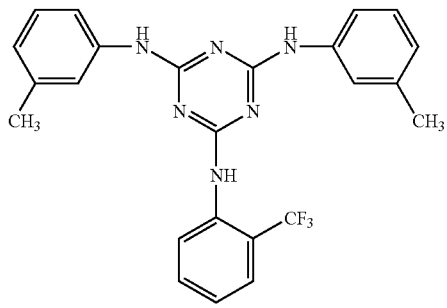
I-(23)
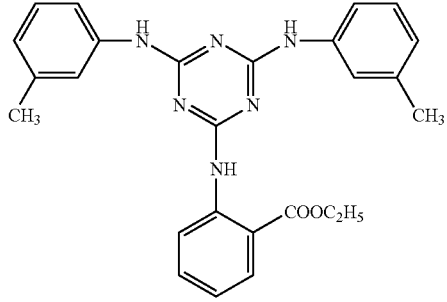
I-(24)
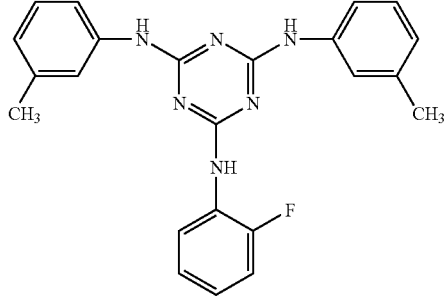
I-(25)
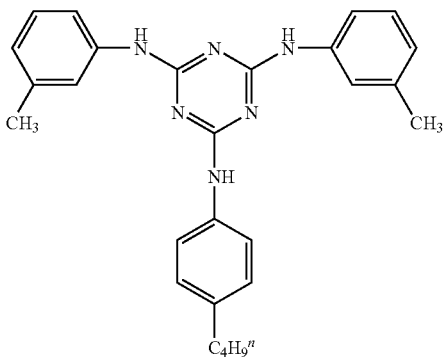
I-(26)
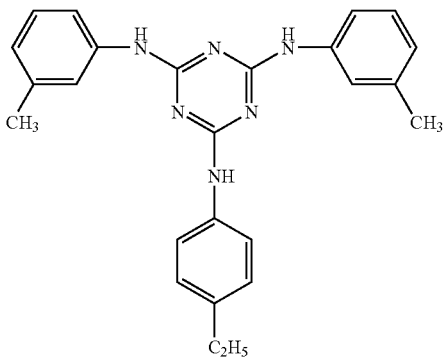
I-(27)
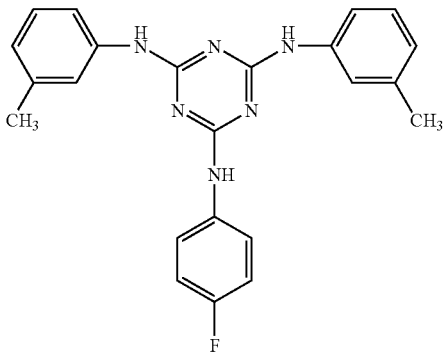
I-(28)
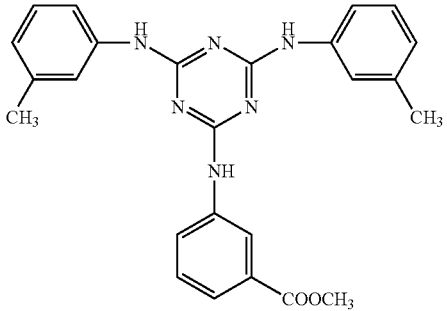
I-(29)

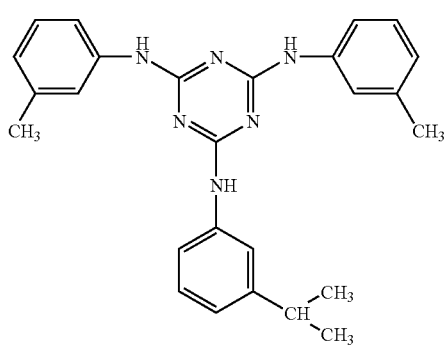 I-(30)
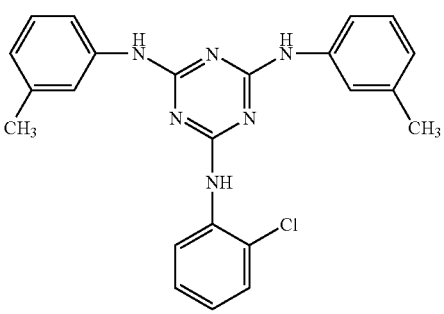 I-(35)
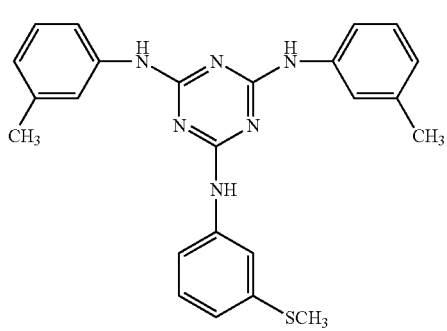 I-(31)
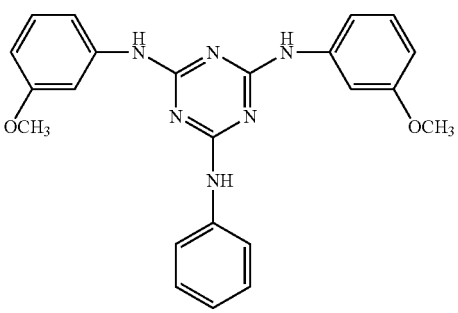 I-(36)
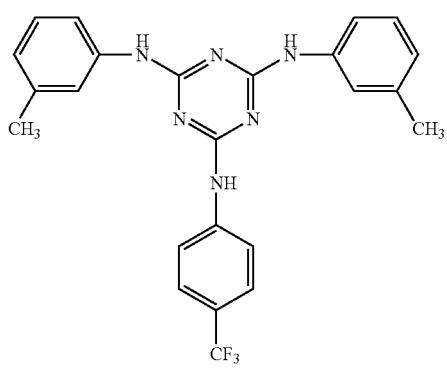 I-(32)
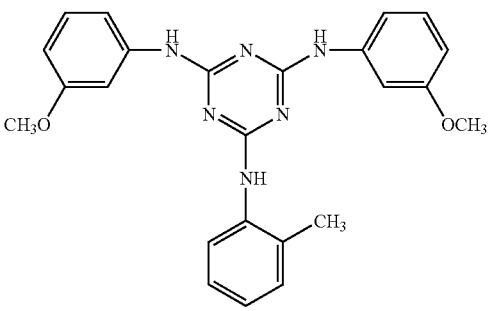 I-(37)
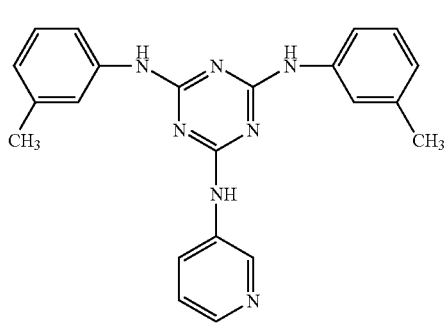 I-(33)
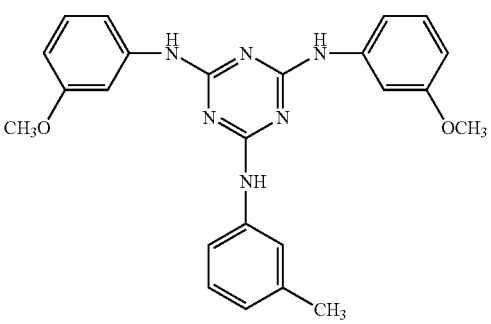 I-(38)
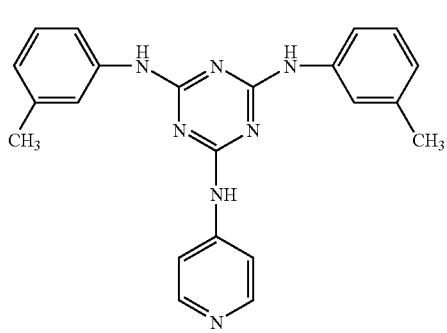 I-(34)
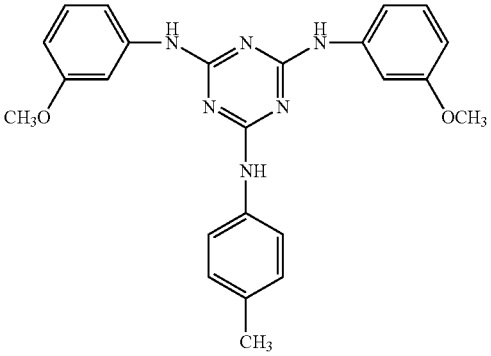 I-(39)

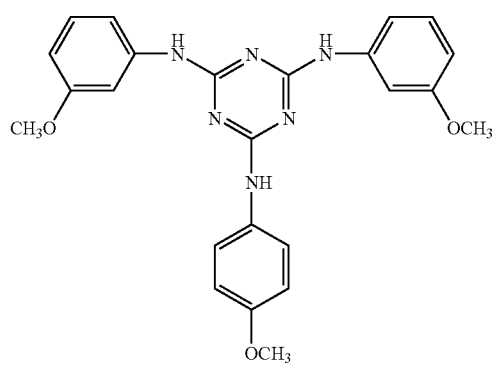
I-(40)
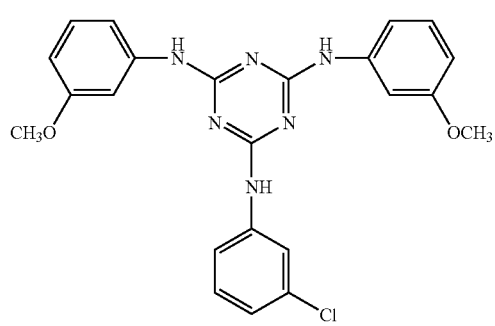
I-(41)
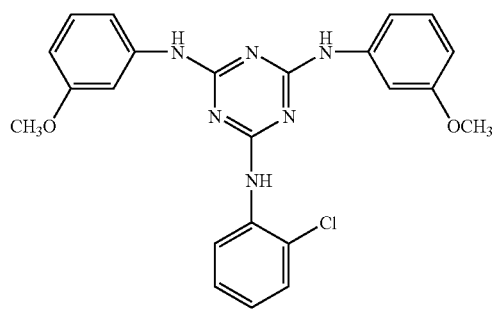
I-(42)
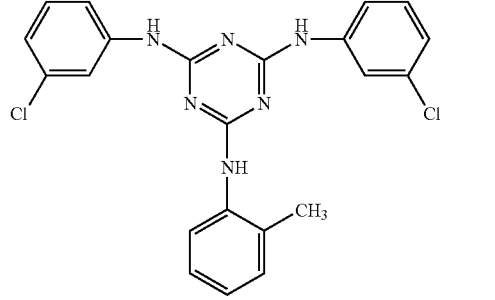
I-(43)
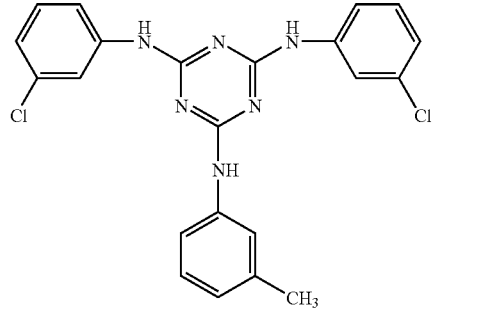
I-(44)
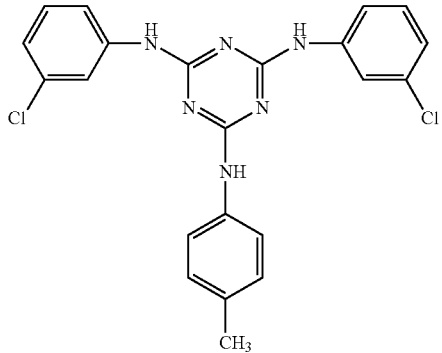
I-(45)
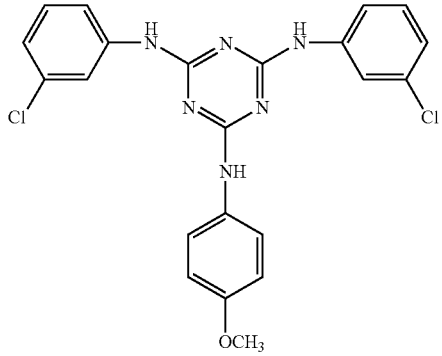
I-(46)
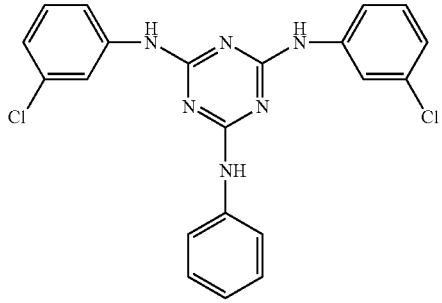
I-(47)
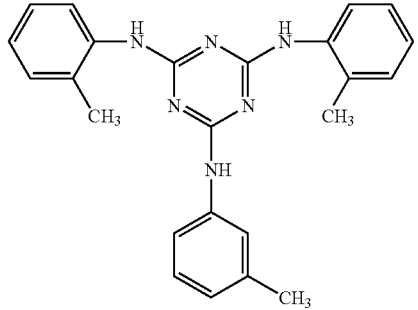
I-(48)

I-(49)
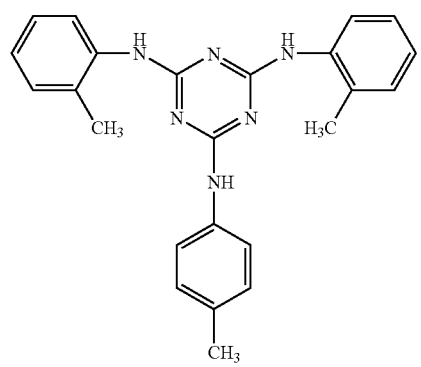
I-(50)
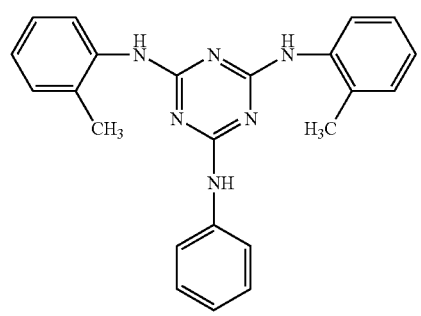
I-(51)
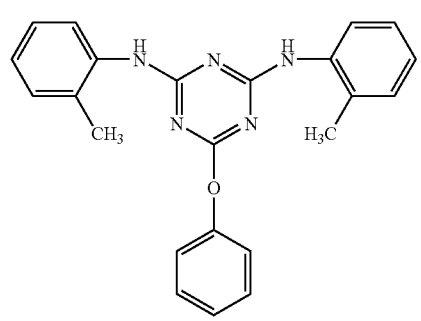
I-(52)
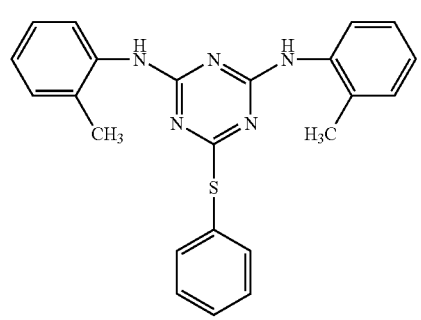
II-(1)
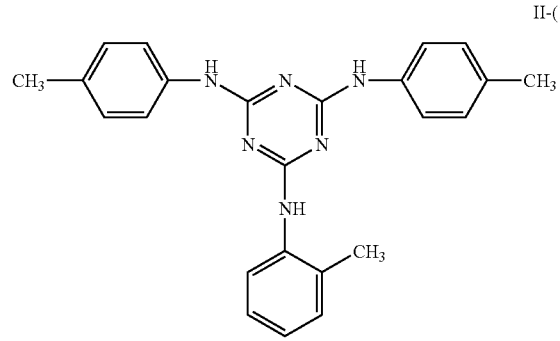
II-(2)
II-(3)
II-(4)
II-(5)

II-(6)
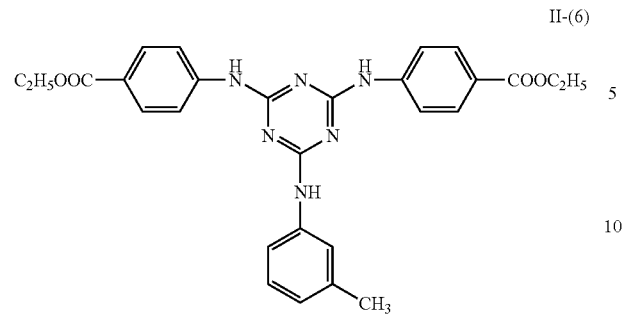
II-(7)
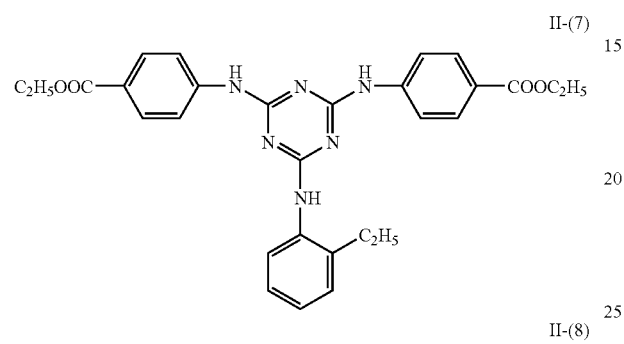
II-(8)
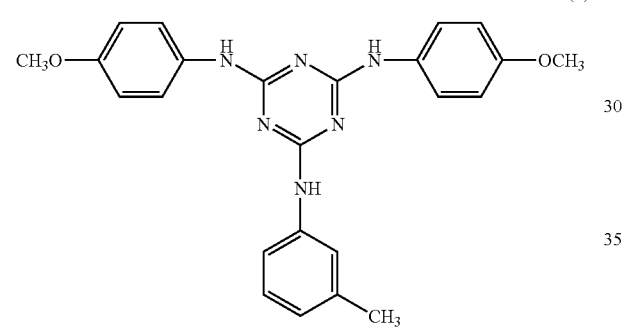
II-(9)
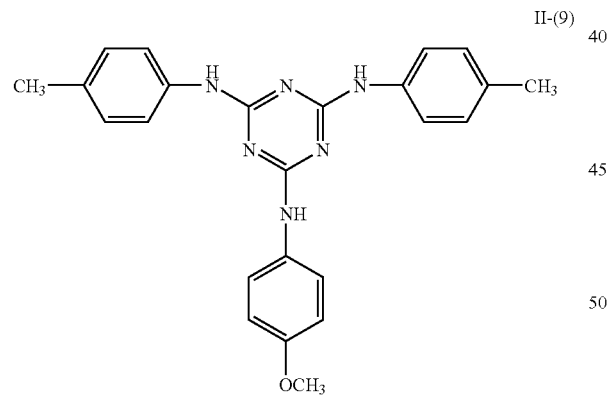
III-(1)
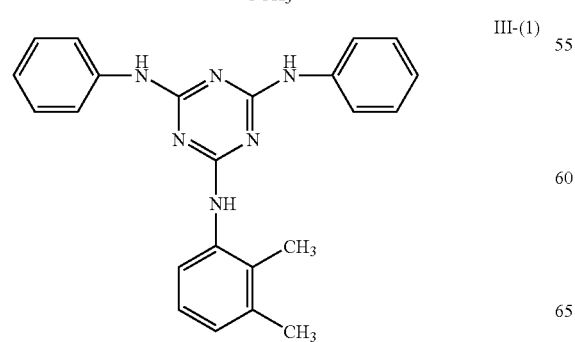
III-(2)
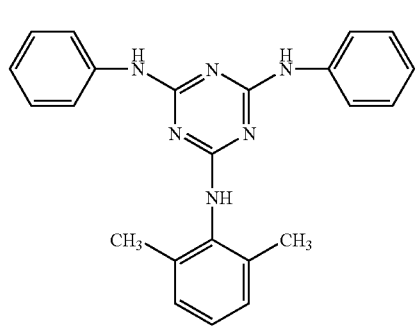
III-(3)
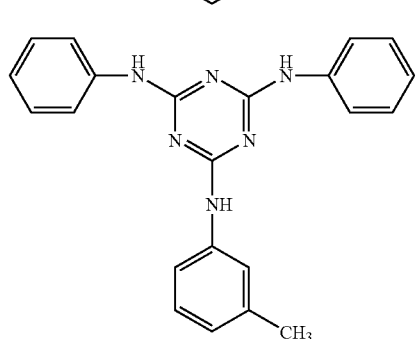
III-(4)
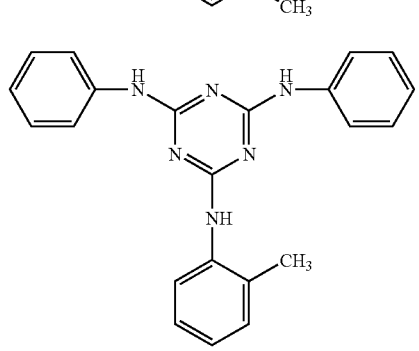
III-(5)
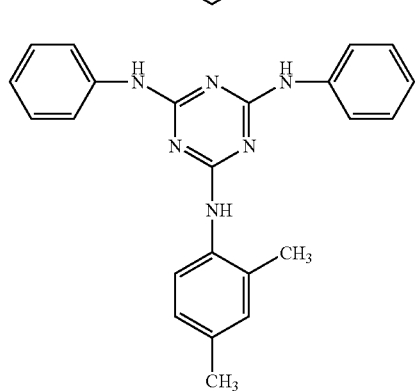
III-(6)
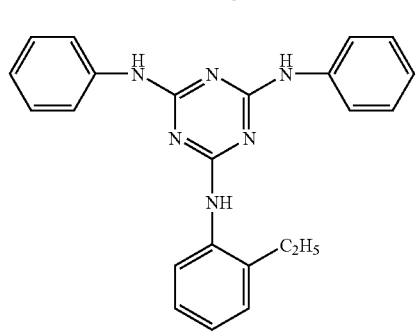

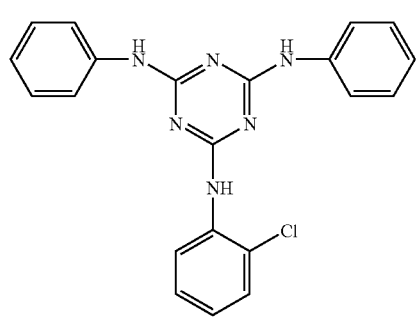
III-(7)
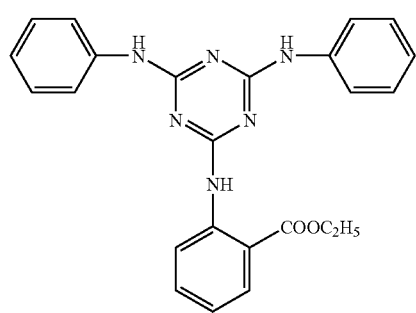
III-(8)
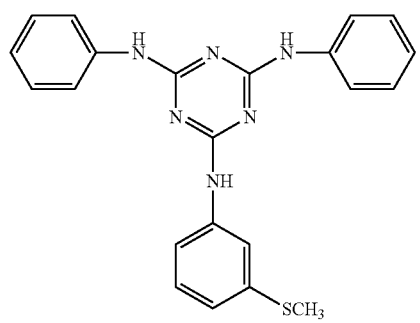
III-(9)
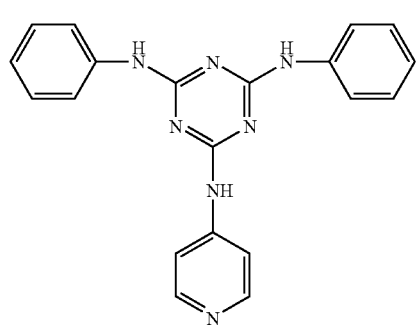
III-(10)
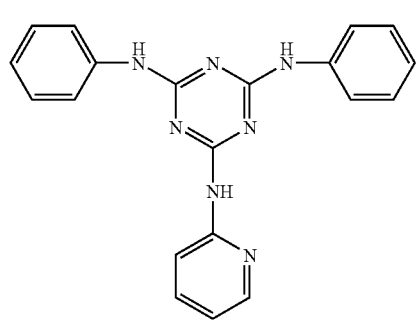
III-(11)
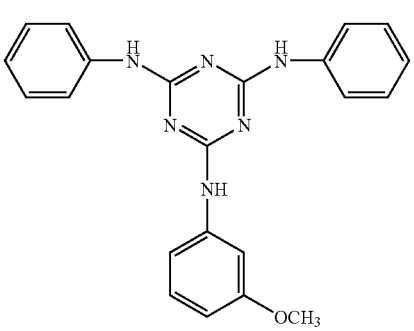
III-(12)
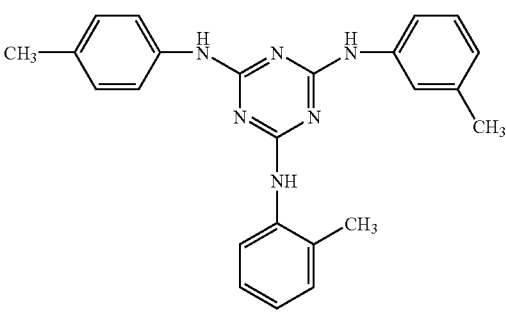
IV-(1)
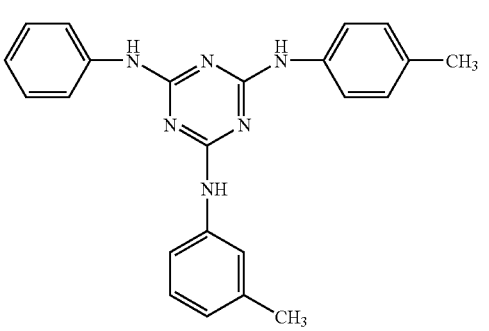
IV-(2)
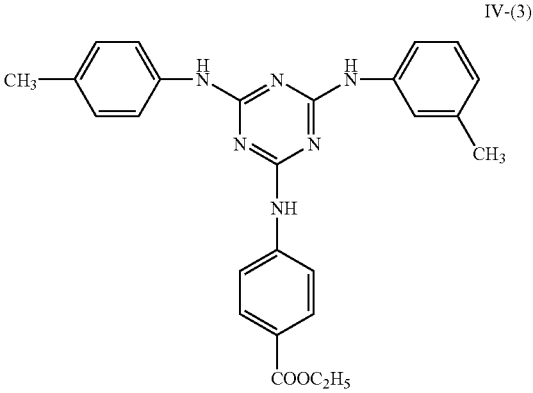
IV-(3)

-continued

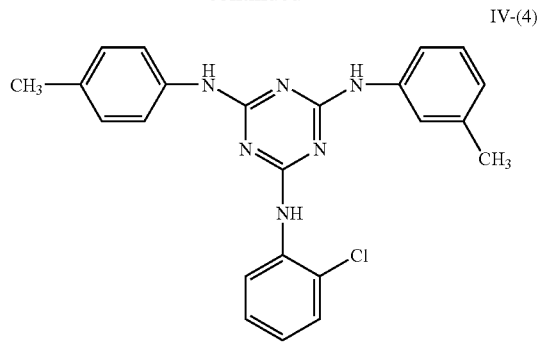
IV-(4)

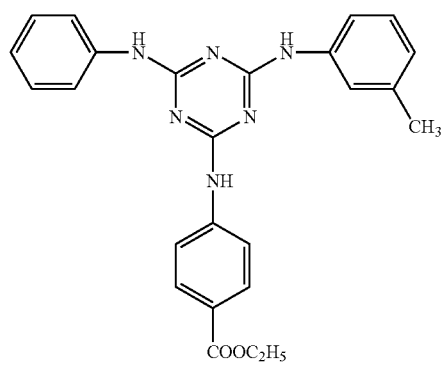
II-(5)

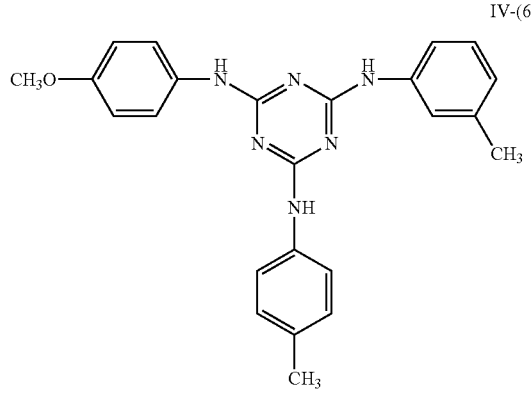
IV-(6)

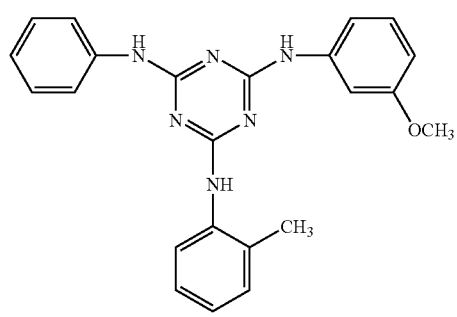
IV-(7)

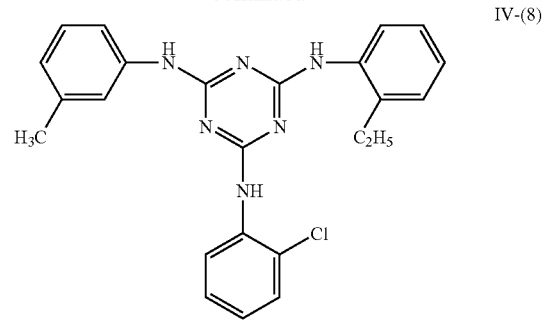
IV-(8)

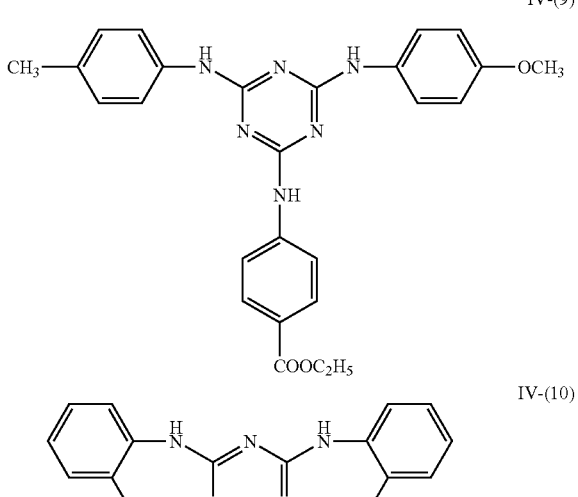
IV-(9)

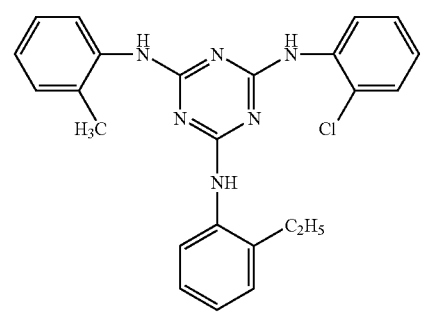
IV-(10)

The wavelength dispersion regulator and light-fastness improving agent in the invention may be preliminarily added in the step of preparing a mixed solution of cellulose acylate. Alternatively, a polymer solution (a dope solution) may be preliminarily prepared and the wavelength dispersion regulator and light-fastness improving agent may be added at any time until the casting. In the latter case, when it is intended to carry out in-line addition and mixing of a dope solution having been prepared by dissolving the polymer in a solvent and a solution having been prepared by dissolving the wavelength dispersion regulator together with a small amount of the polymer, for example, use is preferably made of an in-line mixer such as a static mixer (manufactured by Toray Engineering) and SWJ (Hi-Mixer, a static intratubular mixer manufactured by Toray). The wavelength dispersion regulator to be subsequently added may be mixed with a matting agent at the same time, and further additive(s) such as a retardation controlling agent, a plasticizer (such as triphenyl phosphate and biphenyl phosphate), a degradation inhibiter or a peeling enhancer may be mixed. In the case of using an in-line mixer, it is preferable to conduct concentration and dissolution under a high pressure. In this case, a pressure container of any type may be used without particular restriction, so long as the container withstands a predetermined pressure and allows heating and stirring under the elevated pressure. The pressure container may be appropriately equipped with measuring unit(s) such as a pressure gauge and a thermometer. The pressurization may be carried out by, for example, injecting an inert gas such as nitrogen gas or heating to raise the vapor pressure of a solvent. The heating is carried out preferably from the outside. For example, it is preferable to employ a heater of the jacket type because of easiness in the temperature control. When a solvent is added, the heating temperature is preferably being not lower than the boiling point of the solvent employed and not allowing the solvent to boil. For example, it is appropriate to set the temperature within a range of 30 to 150° C. The pressure is controlled so that the solvent does not boil under the preset temperature. After the dissolution, the resultant mixture is taken out of from the container under cooling, or withdrawn from the container using a pump etc. and cooled with a heat exchanger or the like, followed by film formation. In this step, the mixture may be cooled to room temperature. However, it is preferred to cool it to a temperature lower by 5 to 10° C. than the boiling point of the solvent and directly subject to casting at this temperature, since the dope viscosity can be lowered thereby.

As the wavelength dispersion regulator and light-fastness improving agent in the invention, either one agent or a mixture of two or more thereof may be used.

In the present invention, the wavelength dispersion regulator is added preferably 1.0 to 20% by mass based on cellulose acylate, more preferably 1.0 to 10% by mass, further more preferably 1.5 to 8.0% by mass and most preferably 2.0 to 6.0% by mass. (In this specification, mass ratio is equal to weight ratio.)

In the polymer film according to the present invention, the light-fastness improving agent is contained preferably 10% by mass (0.1 time) or more but not more than 1000% by mass (10 times) based on the wavelength dispersion regulator, preferably 20% by mass (0.2 time) or more but not more than 750% by mass (7.5 times).

In the invention, the wavelength dispersion regulator and light-fastness improving agent may be dissolved in an organic solvent such as an alcohol, methylene chloride or dioxolan and then added to the cellulose acylate solution (dope). Alternatively, they may be added directly to the dope composition.

Next, the polymer film according to the invention will be described in detail.

[Retardation of Film]

It is preferable that the polymer film according to the invention satisfies the following formulae (1) and (2):

70 nm≦R$th$(548)≦300 nm        Formula (1)

R$th$(628)<R$th$(548)<R$th$(446)        Formula (2)

In the formulae (1) and (2), Rth(λ) represents the retardation (expressed in nm) in the film thickness direction that is measured at a wavelength of λ nm.

In the formula (1), Rth(548) preferably ranges from 75 nm to 250 nm and more preferably from 80 nm to 2.30 nm.

It is still preferable that the polymer film according to the invention satisfies the following formula (3-1) or (3-2):

1.0<R$th$(446)/R$th$(548)<4.0        Formula (3-1)

0.5<R$th$(628)/R$th$(548)<1.0        Formula (3-2)

In the formula (3-1), Rth(446)/Rth(548) preferably ranges from 1.1 to 3.0 and more preferably from 1.2 to 2.0.

In the formula (3-2), Rth(628)/Rth(548) preferably ranges from 0.7 to 0.9 and more preferably from 0.8 to 0.95.

In the present specification, Re(λ) and Rth(λ) represent an in-plane retardation and a retardation in the thickness direction at a wavelength of λ, respectively Re(λ) is measured by making light having a wavelength of λ nm incident into the normal line direction in KOBRA 21ADH or WR (manufactured by Oji Science Instruments).

In the case where a film to be measured is expressed by a monoaxial or biaxial index ellipsoid, Rth(λ) can be calculated by the method as described below.

Rth(λ) is calculated by KOBRA 21ADH or WR based on six Re(λ) values, which are measured for incoming light of a wavelength λ nm in six directions which are decided by a 10° step rotation from 0 to 50° with respect to the normal direction of a sample film using an in-plane slow axis, which is decided by KOBRA 21ADH or WR, as an a tilt axis (a rotation axis; defined in an arbitrary in-plane direction if the film has no slow axis in plane); a value of hypothetical mean refractive index; and a value entered as the film thickness.

In the case of a film giving no retardation, (i.e., zero) for incoming light in the direction rotated at a certain angle with respect to the normal direction of the film using an in-plane slow axis as a rotation axis, any retardation values obtained at angles larger than that angle will be calculated by KOBRA 21ADH or WR, after being inverted in the sign to minus.

Also, Rth can be calculated from the following numerical formulae (21) and (22), based on two retardation values measured for incoming light in two rotated directions, while assuming the slow axis as a tilt axis (a rotation axis: defined in an arbitrary in-plane direction if the film has no slow axis); a hypothetical value of the mean refractive index, and an entered value of the film thickness.

$$Re(\theta) = \left[ nx - \frac{ny \times nz}{\sqrt{\left(ny\sin\left(\sin^{-1}\left(\frac{\sin(-\theta)}{nx}\right)\right)\right)^2 + \left(nz\cos\left(\sin^{-1}\left(\frac{\sin(-\theta)}{nx}\right)\right)\right)^2}} \right] \times \frac{d}{\cos\left(\sin^{-1}\left(\frac{\sin(-\theta)}{nx}\right)\right)}$$

Numerical formula (21)

In the above formula, Re(θ) represents retardation value in the direction rotated by angle θ from the direction of normal line.

In the above formula (1), nx represents in-plane refractive index in the direction of slow axis; ny represents in-plane refractive index in the direction normal to nx; nz represents refractive index in the direction normal to nx and ny; and d represents film thickness (nm) of the film.

R$th$=((nx+ny)/2−nz)×d        Numerical formula (22)

In the case where a film to be measured is not expressed by a monoaxial or biaxial index ellipsoid, i.e., a so-called optic axis-free film, Rth(λ) can be calculated by the method as described below.

Rth(λ) is calculated by using KOBRA-21ADH based on plural retardation values which are measured for incoming light of a wavelength λ nm in eleven directions which are decided by a 10° step rotation from 50° to +50° with respect to the vertical direction of the film using an in-plane slow axis, which is decided by KOBRA 21ADH or WR, as an a tilt axis (a rotation axis); value of hypothetical mean refractive index; and a value entered as the film thickness.

In the above-described measurement, the hypothetical value of mean refractive index is available from values listed in catalogues of various optical films in Polymer Handbook (John Wiley & Sons, Inc.). Films the mean refractive indices of which are unknown can be measured by using an Abbe refract meter. Mean refractive indices of some major optical films are listed below: cellulose acylate (1.48), cycloolefin polymer (1.52), polycarbonate (1.59), polymethylmethacrylate (1.49) and polystyrene (1.59). KOBRA 21ADH or WR calculates nx, ny and nz, upon enter of the hypothetical values of these mean refractive indices and the film thickness. Base on thus-calculated nx, ny and nz, Nz=(nx−nz)/(nx−ny) is further calculated.

Although various polymer films are usable as the normal wavelength dispersion polymer film according to the invention, a cellulose acylate film comprising cellulose acylate is particularly preferable from the viewpoint of inexpensiveness of the raw material and the excellent processability into a polarizing plate.

The expression "mainly comprising" cellulose acylate means that the cellulose acylate content amounts to, for example, 70% by mass or more and preferably 80% by mass or more based on the total film weight. The expression "mainly comprising" as will be used hereinafter has the same meaning.

[Cellulose Acylate]

Next, the cellulose acylate that is usable in the invention will be described.

The substitution degree of cellulose acylate means the percentage of acylation of three hydroxyl groups existing in the constitutional unit (glucose forming a (β)1,4-glycoside bond) of cellulose. The substitution degree (acylation degree) can be calculated by measuring the amount of fatty acids bound per constitutional unit mass of cellulose. The measurement is carried out according to "ASTM D817-91".

It is preferable that the cellulose acylate in the invention has an acetyl substitution degree of from 2.80 to 3.00, more preferably from 2.90 to 2.97.

Another cellulose acylate preferred in the invention is cellulose acetate propionate.

In the polymer film according to the invention, it is preferable that the cellulose acylate comprises acetyl groups and propionyl groups and the acetyl substitution degree A and the propionyl substitution degree P satisfy the following formulae (3) and (4):

$$2.00 \leq A+P \leq 2.70 \quad \text{Formula (3)}$$

$$(3-A-P) \times 0.5 \leq P \leq (3-A-P) \times 2. \quad \text{Formula (4)}$$

In the above formulae, A stands for the acetyl substitution degree while P stands for the propionyl substitution degree. With a decrease in the acyl substitution degree of cellulose acylate, the retardation developing properties of the cellulose acylate are lowered. At the same degree of substitution, propionyl groups show a larger tendency to lower the retardation in the thickness direction than acetyl groups. Concerning the bleed-out of the aminobutadiene compound represented by the formula (I), on the other hand, bleed out less occurs at a higher acyl substitution degree. In particular, propionyl groups show a larger bleed-out preventing effect than acetyl groups. By selecting the acetyl substitution degree and the propionyl substitution degree so that the ratio of propionyl groups increases with a decrease in the total acyl substitution degree, therefore, a film having desired wavelength dispersion can be obtained without causing bleed-out of the aminobutadiene compound represented by the formula (I).

As the formula (3), the following formula (3') is more preferable and the following formula (3") is still more preferable:

$$2.10 \leq A+P \leq 2.60 \quad \text{Formula (3')}$$

$$2.20 \leq A+P \leq 2.50 \quad \text{Formula (3")}$$

It is preferable that the cellulose acylate to be used in the invention has a mass average polymerization degree of from 300 to 800, and more preferably from 300 to 600. It is also preferable that the cellulose acylate to be used in the invention has a number average molecular weight of from 70,000 to 230,000, more preferably from 75,000 to 230,000, and most preferably from 78,000 to 120,000.

The cellulose acylate for to be used in the invention can be synthesized by using an acid anhydride or an acid chloride as an acylating agents. In case where the acylating agent is an acid anhydride, use may be made, as a reaction solvent, of an organic acid (for example, acetic acid) or methylene chloride. As a catalyst, a protonic catalyst such as sulfuric acid can be used. In the case where the acylating agent is an acid chloride, use can be made, as a catalyst, of a basic compound. In the most common industrial synthetic method, cellulose is esterified with a mixed organic acid component containing an organic acid (acetic acid, propionic acid, butyric acid) or anhydride thereof (acetic anhydride, propionic anhydride, butyric anhydride) corresponding to an acetyl group or other acyl groups to thereby synthesize a cellulose ester.

In this method, it has been a common practice that cellulose such as cotton linter or wood pulp is activated with an organic acid such as acetic acid and then esterified by using a liquid mixture containing the above-described organic acid components in the presence of a sulfuric acid catalyst. The organic acid anhydride component is used generally in excess relative to the amount of hydroxyl groups existing in the cellulose. In the esterification treatment, hydrolysis reaction (depolymerization reaction) of the cellulose main chain ((β)1,4-glycoside bond) proceeds, in addition to the esterification reaction. As the hydrolysis reaction of the main chain proceeds, the polymerization degree of the cellulose ester lowers and thus the physical properties of the cellulose ester film to be produced are deteriorated. Accordingly, it is preferable that the reaction conditions such as reaction temperature are determined by taking the polymerization degree and molecular weight of the cellulose ester to be obtained into consideration.

To obtain a cellulose ester having a high polymerization degree (i.e., a large molecular weight), it is important to control the maximum temperature in the course of the esterification to 50° C. or lower. The maximum temperature is controlled preferably to from 35 to 50° C., and more preferably from 37 to 47° C. It is preferable that the reaction temperature is 35° C. or higher, since the esterification reaction proceeds smoothly in this case. It is also preferable that the reaction temperature is not higher than 50° C., since no trouble such as lowering in the polymerization degree of the cellulose ester arises in this case.

After the completion of the esterification reaction, the reaction is terminated while inhibiting the temperature rise. Thus, further lowering in the polymerization degree can be inhibited and a cellulose ester having a high polymerization degree can be synthesized. By adding a reaction terminating agent (for example, water, acetic acid) after the completion of the reaction, namely, the excessive acid anhydride not having participating in the esterification reaction is hydrolyzed to produce the corresponding organic acid as a by-product. This hydrolysis reaction is accompanied with vigorous heat generation, thereby raising the temperature in the reaction apparatus. Unless the reaction terminating agent is added at an excessively high speed, there arises no such problem that heat generates rapidly exceeding the cooling capacity of the reaction apparatus and thus the hydrolysis reaction of the cellulose main chain considerably proceeds, thereby lowering the polymerization degree of the target cellulose ester. A portion of the catalyst has been bonded to the cellulose during the esterification reaction and then mostly dissociated from the cellulose during the addition of the reaction terminating agent. Unless the reaction terminating agent is added at an excessively high speed, a sufficient reaction time for the dissociation of the catalyst is ensured so that there scarcely arises such a problem that a part of the catalyst remains in the state bonded to the cellulose. A cellulose ester having a strong acid catalyst bonded partially thereto has a very poor stability, and decomposes easily upon heating in drying, etc, so as to lower the polymerization degree. From these reasons, it is desirable to add, after the completion of the esterification reaction, a reaction terminating agent over preferably 4 minutes or longer, more preferably from 4 to 30 minutes to terminate the reaction. It is preferable that the reaction terminating agent is added within a time of 30 minutes or less, since no problem such as a decrease in the industrial productivity arises in this case.

As the reaction terminating agent, use is commonly made of water or an alcohol capable of decomposing an acid anhydride. In the invention, however, it is preferable to employ a mixture of water with an organic acid as the reaction terminating agent so as to prevent the sedimentation of a triester having a low solubility in various organic solvents. By carrying out the esterification reaction under the conditions as described above, a high molecular weight cellulose ester having a mass average polymerization degree of 500 or more can be easily synthesized.

[Production of Normal Wavelength Dispersion Cellulose Acylate Film]

The cellulose acylate film in the invention can be produced by the solvent casting method. In the solvent casting method, a film is produced by using a solution of cellulose acylate dissolved in an organic solvent (dope).

The organic solvent preferably contains a solvent that is selected from an ether having 3 to 12 carbon atoms, a ketone having 3 to 12 carbon atoms, an ester having 3 to 12 carbon atoms and a halogenated hydrocarbon having 1 to 6 carbon atoms.

The ether, ketone and ester as described above may have a cyclic structure. Also use can be made of a compound having two or more of any of the functional groups of the above-described ether, ketone and ester (i.e., —O—, —CO— and —COO—) as the organic solvent. The organic solvent may have another functional group such as an alcoholic hydroxyl group. In the case of an organic solvent having two or more kinds of functional groups, it preferably has carbon atoms within a range of the above-described preferred carbon atoms of the solvent having any one of the functional groups.

Examples of the ether having 3 to 12 carbon atoms include diisopropyl ether, dimethoxymethane, dimethoxyethane, 1,4-dioxane, 1,3-dioxolan, tetrahydrofuran, anisole and phenetole.

Examples of the ketone having 3 to 12 carbon atoms include acetone, methyl ethyl ketone, diethyl ketone, diisobutyl ketone, cyclohexanone and methylcyclohexanone.

Examples of the ester having 3 to 12 carbon atoms include ethyl formate, propyl formate, pentyl formate, methyl acetate, ethyl acetate and pentyl acetate.

Examples of the organic solvent having two or more kinds of functional groups include 2-ethoxyethyl acetate, 2-methoxyethanol and 2-butoxy ethanol.

It is preferable that the halogenated hydrocarbon having 1 to 6 carbon atoms is one having 1 or 2 carbon atoms and more preferably 1 carbon atom. It is preferable that the halogen in the halogenated hydrocarbon is chlorine. In the halogenated hydrocarbon, the ratio of halogen-substituted hydrogen atoms is preferably 25 to 75% by mol, more preferably 30 to 70% by mol, more preferably 35 to 65% by mol, and most preferably 40 to 60% by mol. Methylene chloride may be cited as a typical halogenated hydrocarbon.

Moreover, use may be made of a mixture of two or more kinds of organic solvents.

The cellulose acylate solution (dope) can be prepared by a common method which comprises, for example, treating at a temperature of 0° C. or higher (room temperature or a high temperature). The preparation of the cellulose acylate solution can be carried out with the use of a method and apparatus commonly employed for preparing a dope by the solvent casting method. In a common method, it is preferable to use a halogenated hydrocarbon (especially methylene chloride) as an organic solvent.

The amount of cellulose acylate in the cellulose acylate solution is controlled so as to adjust the content thereof in the resultant solution to 10 to 40% by mass. It is more preferable that the cellulose acylate content is 10 to 30% by mass. In the organic solvent (main solvent), any of the additives as will be described hereinafter may be added.

The cellulose acylate solution can be prepared by, for example, stirring cellulose acylate and an organic solvent at room temperature (0 to 40° C.). A solution having a high concentration may be stirred under pressurized and heated conditions. More particularly speaking, cellulose acylate and an organic solvent are put and sealed in a pressurizable container and then stirred under elevated pressure while heating within a temperature range from the boiling point of the solvent under elevated pressure at room temperature to a temperature at which the solvent would not boil. The heating temperature is usually 40° C. or higher, preferably 60 to 200° C., and more preferably 80 to 110° C.

The individual components may be preliminarily mixed roughly and then put into the container. Alternatively, they may be sequentially put into the container. The container must be constituted in such a manner that the components can be stirred. The container can be pressurized by injecting an inert gas such as nitrogen gas. Further, use may be made of an increase in the vapor pressure of the solvent caused by heating. Alternatively, after sealing the container, the individual components may be added under pressurization.

In the case of heating, it is preferable to heat from the outside of the container. For example, a heating unit of the jacket type can be used. Alternatively, the whole container can be heated by locating a plate heater outside the container and providing a pipe through which a liquid is circulated.

It is preferable that the stirring is carried out by providing stirring blades inside the container and use the same to stir. As the stirring blades, use is preferably made of those having such a length as attaining close the wall of the container. It is also preferable that the stirring blades are equipped with a scraping blade at the end of the stirring blades in order to renew a liquid film on the wall of the container.

The container may be appropriately equipped with measuring unit(s) such as a pressure gauge and a thermometer.

The individual components are dissolved in the solvent within the container. The dope thus prepared is taken out of the container after cooling, or is cooled by using a heat exchanger or the like after being taken out of the container.

The cellulose acylate solution can be also prepared by the cooling dissolution method. In the cooling dissolution method, cellulose acylate can be dissolved even in an organic solvent in which the cellulose acylate is hardly soluble by using a conventional dissolution method. Further, it is expected that a homogeneous solution can be rapidly obtained by the cooling dissolution method in the case of using a solvent in which cellulose acylate can be easily dissolved by a conventional dissolution method.

In the cooling dissolution method, cellulose acylate is first gradually added into an organic solvent under stirring at room temperature. It is preferable to control the amount of the cellulose acylate so as to give a concentration of 10 to 40% by mass in the mixture. It is more preferable that the content of the cellulose acylate is from 10 to 30% by mass. Further, arbitrary additive(s) as will be described hereinafter may be preliminarily added to the mixture.

Next, the mixture is cooled to, for example, −100 to −10° C. (preferably −80 to −10° C., more preferably −50 to −20° C., and most preferably −50 to −30° C.). The cooling can be carried out in, for example, a dry ice/methanol bath (−75° C.) or a cooled diethylene glycol solution (−30 to −20° C.). Due to the cooling, the mixture of the cellulose acylate and the organic solvent solidifies.

It is preferable that the cooling speed is 4° C./min or higher, more preferably 8° C./min or higher, and more preferably 12° C./min or higher. Although a higher cooling speed is more preferred, 10000° C./sec is the theoretical upper limit, 1000° C./sec is the technical upper limit, and 100° C./sec is the practical upper limit. The cooling speed is a value determined by dividing the difference between the initial cooling temperature and the final cooling temperature by the time period from the beginning of the cooling to the achievement of a final cooling temperature.

When the thus cooled mixture is heated to, for example, 0 to 200° C. (preferably 0 to 150° C., more preferably 0 to 120° C., and most preferably 0 to 50° C.), the cellulose acylate dissolves in the organic solvent. To rise the temperature, the mixture may be just allowed to stand at room temperature or heated in a warm bath. The temperature rising speed is preferably 4° C./min or higher, morer preferably 8° C./min or higher, and most preferably 12° C./min or higher. Although a higher temperature rising speed is more preferred, 10000° C./sec is the theoretical upper limit, 1000° C./sec is the technical upper limit, and 100° C./sec is the practical upper limit. The temperature rising speed is a value obtained by dividing the difference between the initial rising temperature and the final temperature rising temperature by the time period from the beginning of temperature rising to the achievement of the final rising temperature.

As discussed above, a homogeneous cellulose acylate solution is obtained. In the case where dissolution still remains insufficient, the cooling and heating procedures may be repeated. Whether or not the dissolution is sufficient can be determined merely by observing the appearance of the solution with naked eye.

In the cooling dissolution method, it is preferable to use a sealable container to thereby avoid the invasion of moisture caused by dew condensation in the course of the cooling. By elevating pressure in the course of the cooling and reducing pressure in the course of heating, furthermore, the dissolution time can be shortened. To elevate and reduce the pressure, it is desirable to use a pressure-resistant containers.

When measured with a differential scanning calorimeter (DSC), a 20% by mass solution prepared by dissolving cellulose acetate (acetylation degree: 60.9%, viscosity-average degree of polymerization: 299) in methyl acetate by the cooling dissolution method has a pseudo-phase transition point for a sol state and a gel state at around 33° C. Namely, it occurs in a homogeneous gel state at the temperature or lower. Accordingly, it is preferable that this solution is stored at the pseudo-phase transition point or higher, more preferably a temperature around a gel phase transition temperature +10° C. However, it should be noted that the pseudo-phase transition point varies depending on the acetylation degree or the viscosity average polymerization degree of the cellulose acetate, the concentration of the solution, and the organic solvent employed.

From the cellulose acylate solution (dope) thus prepared, a cellulose acylate film is produced by the solvent casting method. The dope is cast on a drum or a band and then the solvent is evaporated to form a film. Before the casting, it is preferable to control the concentration of the dope to thereby give a solid content of 18 to 35%. It is also preferable that the surface of the drum or the band has been specular-finished. It is preferable that the dope is cast on a drum or a band having a surface temperature of 10° C. or lower.

Drying procedures in the solvent casting method are disclosed in U.S. Pat. Nos. 2,336,310, 2,367,603, 2,492,078, 2,492,977, 2,492,978, 2,607,704, 2,739,069 and 2,739,070, GB Patent Nos. 640731 and 736892, JP-B-45-4554, JP-B-49-5614, JP-A-60-176834, JP-A-60-203430 and JP-A-62-1150.35. The drying on a band or a drum can be carried out by blowing air or an inert gas such as nitrogen.

It is also possible that the thus obtained film is peeled off from the drum or band and then further dried by using a high-temperature air stream with a gradual increase in temperature from 100 to 160° C. to thereby evaporate the residual solvent. This method is disclosed in JP-B-5-17844. According to this method, the time from the casting to the peeling off can be shortened. In order to carry out the method, it is necessary that the dope sets to gel at the surface temperature of the drum or band in the casting step.

The cellulose acylate solution (dope) thus prepared, may be subjected to casting in a plural number of layers to form a film. In this case, it is preferred to form a cellulose acylate film by a solvent casting method. The dope is cast on a drum or a band and then the solvent is evaporated to form a film. Before the casting, it is preferable to control the concentration of the dope to thereby give a solid content of 10 to 40%. It is also preferable that the surface of the drum or the band has been specular-finished.

In the case of casting a plural number of cellulose acylate solutions in two or more layers, these cellulose acylate solutions can be cast. That is, a film may be formed by casting and laminating respective solutions containing cellulose acylate from a plural number of casting ports that are placed in the traveling direction of a support at intervals. For this purpose, use may be made of methods disclosed in, for example, JP-A-61-158414, JP-A-1-122419 and JP-A-11-198285. Alternatively, a film may be formed by casting cellulose acylate solutions from two casting ports. For this purpose, use can be made of methods disclosed in, for example, JP-B-60-27562, JP-A-61-94724, JP-A-61-947245, JP-A-61-104813, JP-A-61-158413 and JP-A-6-134933. Further, use can be made of a casting method for the formation of a cellulose acylate film disclosed in JP-A-56-162617 which comprises enclosing a flow of a high-viscosity cellulose acylate solution within a low-viscosity cellulose acylate solution and simultaneously extruding these high-viscosity and low-viscosity cellulose acylate solutions.

Further, a film may be formed by using two casting ports wherein a film is formed on a support and then peeled off via a first casting port and a second casting is conducted on the side of the film being in contact with the support face. For this purpose, use may be made of, for example, a method disclosed in JP-B-44-20235.

As the cellulose acylate solutions to be cast, use may be made of either the same type solutions or two or more different types of cellulose acylate solutions. To impart functions to a plural number of cellulose acylate layers, the cellulose acylate solutions for the respective functions may be extruded from the respective casting ports. Furthermore, the cellulose acylate solution in the invention can be cast simultaneously with other functional layers (for example, an adhesive layer, a dye layer, an antistatic layer, an antihalation layer, a UV absorbing layer, a polarizer layer and so on).

To achieve a desired thickness film with the use of a conventional solution for forming a single layer, it is required to extrude a cellulose acylate solution having a high concentration and a high viscosity. In this case, however, solid matters are formed due to the poor stability of the cellulose acylate solution, which brings about problems such as fisheye failure or worsening in surface planarity. These problems can be solved by casting a plural number of cellulose acylate solutions from casting ports so that high-viscosity solutions are simultaneously extruded on a support. Thus, it is possible not only to form a film having an improved surface planarity and excellent surface conditions but also to reduce the drying load owing to the use of the concentrated cellulose acylate solutions, thereby elevating the production speed of the film.

The cellulose acylate film may further contain a degradation inhibitor (for example, an antioxidant, a peroxide decomposition agent, a radical inhibitor, a metal inactivator, an acid trapping agent, an amine, etc.). Such degradation inhibitors are disclosed in JP-A-3-199201, JP-A-5-1907073, JP-A-5-194789, JP-A-5-271471 and JP-A-6-107854. The addition amount of the degradation inhibitor is preferably 0.01 to 1% by mass of the solution (dope) to be prepared, and more preferably 0.01 to 0.2% by mass. It is preferable that the addition amount is 0.01% by mass or more, since the degradation inhibitor can fully exert its effect in this case. It is also preferable that the amount is 1% by mass or less, since there scarcely arises the bleeding out (weep) of the degradation inhibitor to the film surface in this case. Examples of the particularly preferred examples of the degradation inhibitor include butylated hydroxytoluene (BHT) and tribenzylamine (TBA).

These steps of from the casting to the post-drying may be carried out either in the air atmosphere or an inert gas (for example, nitrogen gas) atmosphere. In the production of the cellulose acylate film according to the invention, use may be made of a winding machine that has been commonly employed in the art. Namely, the film can be wound by using a winding method such as the constant tension method, the constant torque method, the tapered tension method or the programmed tension controlling method wherein the internal stress is maintained constant.

[Thickness of Polymer Film]

The thickness of the polymer film of the invention is preferably 10 μm to 200 μm, more preferably 20 μm to 150 μm, and more preferably 30 μm to 100 μm.

[Light-Fastness of Polymer Film]

The light-fastness of a polymer film can be evaluated based on change in the retardation and coloration in the film after irradiating the film with a high-illuminance light source such as xenone. It is preferable that the cellulose acylate film of the invention shows a change in the retardation represented by the following formula (A) of 10% or less and more preferably 5% or less, when irradiated with a super xenon weathermeter SX75 (manufactured by Suga Test Instruments, conditions of 60° C. and 50% RH) for 200 hours.

$$\text{Change in retardation}(\%) = (R_{th} \text{ before irradiation} - R_{th} \text{ after irradiation})/R_{th} \text{ before irradiation} \times 100 \quad \text{Formula (A)}$$

[Saponification Treatment]

The polymer film of the invention may be subjected to an alkali saponification treatment, thereby improving the adhesion to a polarizer material such as a polyvinyl alcohol and enabling the utilization thereof as the polarizing plate protective films.

It is preferable that the alkali saponification treatment of the polymer film according to the invention is carried out by in cycles each comprising soaking the film surface in an alkali solution, neutralizing with an acidic solution, washing with water, and then drying. As the alkali solution, use may be preferably made of a potassium hydroxide solution or a sodium hydroxide solution, and the hydroxide ion concentration thereof is preferably 0.1 to 5.0 mol/L, and more preferably 0.5 to 4.0 mol/L. The temperature of the alkali solution is preferably within a range of room temperature to 90° C., more preferably within a range of 40 to 70° C.

<Production of Polarizing Plate>

(Polarizing Plate)

A polarizing plate comprises a polarizer and two transparent protective films which are provided in both sides of the polarizer. The cellulose acylate film of the invention can be used as one of the protective films. As the other protective film, a common cellulose acetate film may be used.

The polarizing plate according to the invention comprises a polarizer and a protective film that is provided in at least one side of the polarizer, wherein the protective film is the polarizing plate protective film according to the invention.

The polarizer includes an iodine-containing polarizer, a dye-containing polarizer using a dichroic dye, and a polyene-based polarizer. The iodine-containing polarizer and the dye-containing polarizer are generally produced by using a polyvinyl alcohol-based film. In the case of using the cellulose acylate film of the invention as a protective film for the polarizing plate, the method for producing the polarizing plate is not particularly limited, and the polarizing plate may be produced by a commonly employed method. There has been known a method which comprises subjecting the resultant cellulose acylate film to an alkali treatment and bonding the film on both sides of a polarizer that has been prepared by stretching a polyvinyl alcohol film in an iodine solution, using an aqueous solution of a completely saponified polyvinyl alcohol aqueous solution. As a substitute for the alkali treatment, an easily adhesive processing may be conducted, as disclosed in JP-A-6-94915 and JP-A-6-118232. Examples of the adhesive to be used for bonding the treated surface of the protective film to the polarizer include polyvinyl alcohol-based adhesives such as a polyvinyl alcohol-based adhesive and a polyvinyl butyral-based adhesive and vinyl-based latexes such as a butyl acrylate-based latex. The polarizing plate is constituted by the polarizer and the protective films for protecting both sides of the polarizer and, further, a protection film provided on one side of the polarizing plate and a separable film provided on the opposite side thereof. The protection film and the separable film are used for the purpose of protecting the polarizing plate upon shipping, checking the product and so on. In this case, the protection film is bonded for the purpose of protecting the surface of the polarizing plate and is used on the side opposite to the side which is to be bonded onto a liquid crystal plate. On the other hand, the separable film is used for the purpose of covering the adhesive layer to be laminated onto the liquid crystal plate and is used on the side which is to be bonded onto the liquid crystal plate.

It is preferable that the cellulose acylate film of the invention is bonded onto the polarizer so that the transmission axis of the polarizer coincides with the slow axis of the cellulose acylate film of the invention. It has been found by the evaluation of the polarizing plate having been produced under cross-Nicol position of the polarizing plate that, when the rectangular accuracy between the slow axis of the cellulose acylate film of the invention and the absorption axis (an axis crossing at right angles with the transmission axis) is more than 1°, polarizing performance under cross-Nicol position of the polarizing plate is deteriorated and thus there arises filtering of light. In this case, a sufficient black level or a sufficient contrast can not be obtained when such a polarizing plate is combined with a liquid crystal cell. Therefore, it is preferred that deviation between the direction of the main refractive index (nx) of the cellulose acylate film of the invention and the direction of the transmission axis of the polarizing plate is preferably within 1°, more preferably within 0.5°.

It is preferable that the polarizing plate according to the invention satisfies at least one of the following formulae (a) to (d), wherein TT represents a single plate transmittance, PT represents a parallel transmittance, CT represents a cross transmittance, and P represents a polarization degree, each at 25° C. and 60% RH:

$$40.0 \leq TT \leq 45.0 \tag{a}$$

$$30.0 \leq PT \leq 40.0 \tag{b}$$

$$CT \leq 2.0 \tag{c}$$

$$95.0 \leq P \tag{d}$$

It is still preferable that single plate transmittance TT, the parallel transmittance PT, the cross transmittance CT respectively satisfy the following relationships in this order: $40.5 \leq TT \leq 45$, $32 \leq PT \leq 39.5$ and $CT \leq 1.5$, and more preferably $41.0 \leq TT \leq 44.5$, $34 \leq PT \leq 39.0$ and $CT \leq 1.3$. The polarization degree P is preferably 95.0% or more, more preferably 96.0% or more and still more preferably 97.0% or more.

It is preferable that the polarizing plate according to the invention satisfies at least one of the following formulae (e) to (g), wherein CT(λ) represents a cross transmittance at a wavelength of λ nm:

$$CT(380) \leq 2.0 \tag{e}$$

$$CT(410) \leq 1.0 \tag{f}$$

$$CT(700) \leq 0.5 \tag{g}$$

It is more preferable that the polarizing plate according to the invention satisfies at least one of the following requirements, i.e., $CT(380) \leq 1.95$, $CT(410) \leq 0.9$ and $CT(700) \leq 0.49$, and more preferably $CT(380) \leq 1.90$, $CT(410) \leq 0.8$ and $CT(700) \leq 0.48$.

It is preferable that the polarizing plate of the present invention satisfies at least one of the following formulae (j) and (k), wherein ΔCT and ΔP represent change in cross transmittance and polarization degree, respectively, in the case where the polarizing plate is allowed to stand at 60° C. and 95% RH for 500 hours:

$$-6.0 \leq \Delta CT \leq 6.0 \tag{j}$$

$$-10.0 \leq \Delta P \leq 0.0 \tag{k}$$

wherein the change means a value calculated by subtracting a measurement value before the test from a measurement value after the test.

It is more preferable that the polarizing plate according to the invention satisfies at least one of the following requirements, i.e., $-5.8 \leq \Delta CT \leq 5.8$ and $-9.5 \leq \Delta P \leq 0.0$, and more preferably $-5.6 \leq \Delta CT \leq 5.6$ and $-9.0 \leq \Delta P \leq 0.0$.

It is preferable that the polarizing plate of the invention satisfies at least one of formulae (h) and (i), wherein ΔCT and ΔP represent change in cross transmittance and polarization degree, respectively, in the case where the polarizing plate is allowed to stand at 60° C. and 90% RH for 500 hours:

$$-3.0 \leq \Delta CT \leq 3.0 \tag{h}$$

$$-5.0 \leq \Delta P \leq 0.0 \tag{i}$$

It is preferable that the polarizing plate of the present invention satisfies least one of formulae (l) and (m), wherein ΔCT and ΔP represents change in cross transmittance and polarization degree, respectively, in the case where the polarizing plate is allowed to stand at 80° C. for 500 hours:

$$-3.0 \leq \Delta CT \leq 3.0 \tag{l}$$

$$-2.0 \leq \Delta P \leq 0.0 \tag{m}$$

The single plate transmittance TT, the parallel transmittance PT and the cross transmittance CT of the polarizing plate are measured by using UV3100PC (manufactured by SHIMADZU CORPORATION) within a range of 380 nm to 780 nm. In each of TT, PT and CT, the mean of values measured 10 times (mean within a range of 400 nm to 700 mm) is adopted. The polarization degree P can be obtained by the equation: polarization degree (%)=100×[(parallel transmittance−cross transmittance)]/(parallel transmittance+cross transmittance)]$^{1/2}$. The polarizing plate durability test is carried out in two modes including (1) the polarizing plate alone and (2) the polarizing plate bonded to a glass plate via a pressure-sensitive adhesive. To measure the polarizing plate alone, two samples each having the cellulose acylate film according to the invention inserted between two polarizers are prepared and located orthogonally followed by the measurement. In the mode of bonding the polarizing plate to a glass plate, two samples (about 5 cm×5 cm) each having the polarizing plate bonded to the glass plate in such a manner that the cellulose acylate film according to the invention is in the glass plate side are prepared. The single plate transmittance is measured by setting the film side of the samples toward a light source. Two samples are measured respectively and the mean is referred to as the transmittance of single plate.

<Functionalization of Polarizing Plate>

The polarizing plate according to the invention may be preferably used as a functionalized polarizing plate by combining with an antireflection film for improving visibility of the display, a brightness increasing film, or an optical film having a functional layer such as a hard coating layer, a forward scattering layer, or an antiglare (antidazzle) layer (Antireflection Film)

The polarizing plate according to the invention can be used in combination with an antireflection film. As the antireflection film, use may be made of a film having a reflectivity of about 1.5% which is composed of a single layer of a low refractive material such as a fluoropolymer, or a film having a reflectivity of about 1% with the use of the interference of thin layers. It is preferable in the invention that a low refractive layer and at least one more layer having a higher refractive index higher than the low refractive layer (i.e., a high refractive layer or an middle refractive layer) are laminated on a transparent support. In the invention, moreover, use can be also preferably made of antireflection films described in Nitto Giho, Vol. 38, No. 1, May 2000, p. 26 to 28, JP-A-2002-301783 and so on.

The refractive indexes of the layers respectively satisfy the following relations.

Refractive index of high refractive layer>Refractive index of middle refractive layer>Refractive index of transparent support>Refractive index of low refractive layer.

As the transparent support to be used in the antireflection film, use may be preferably made of the above mentioned transparent polymer films for the protective film of the polarizer.

The refractive index of the low refractive layer is preferably from 1.20 to 1.55, and more preferably from 1.30 to 1.50. It is preferred that the low refractive layer is used as the outermost layer having a scratch resistance and antifouling properties. It is also preferred to use a silicone-containing compound or a fluorine-containing compound, etc, for imparting slipperiness to the surface to thereby improve the scratch resistance.

As the fluorine-containing compound, use can be preferably made of, for example, compounds disclosed in JP-A-9-222503, paragraphs [0018] to [0026]; JP-A-11-38202, paragraphs [0019] to [0030]; JP-A-2001-40284, paragraph [0027] to [0028]; JP-A-2000-284102, etc.

As the silicone-containing compound, a compound having a polysiloxane structure is preferred. It is also possible to use reactive silicones such as SILAPLANE (manufactured by Chisso Corporation) and polysiloxanes having silanol end groups disclosed in JP-A-11-258403, etc. therefor. Also, use can be made of a compound prepared by hardening an organic metal compound such as a silane coupling agent and a silane coupling agent having a particular fluorohydrocarbon group by a condensation reaction in the presence of a catalyst (i.e., compounds disclosed in JP-A-58-142958, JP-A-58-147483, JP-A-58-147484, JP-A-9-157582, JP-A-11-106704, JP-A-2000-117902, JP-A-2001-48590, JP-A-2002-53804, etch).

The low refractive layer may preferably contain another additive such as a filler (for example, a low refractive inorganic compound having an average primary particle size of 1 to 150 nm composed such as silicon dioxide (silica) or a fluorine-containing compound (magnesium fluoride, calcium fluoride, barium fluoride, etch), organic microparticles disclosed in JP-A-11-3820, paragraphs [0020] to [0038], and so on), a silane coupling agent, a slipping agent, or a surfactant.

The low refractive layer may be formed by the gas phase method (for example, the vacuum deposition method, the sputtering method, the ion plating method, the plasma CVD method, etc.). However, it is preferable from the viewpoint of inexpensiveness to form the low refractive layer by the coating method. Preferred examples of the coating methods include the dip coating method, the air-knife coating method, the curtain coating method, the roller coating method, the wire bar coating method, the gravure coating method, and the microgravure coating method.

The thickness of the low refractive layer is preferably from 30 to 200 nm, more preferably from 50 to 150 nm, and most preferably from 60 to 120 nm.

It is preferable that the middle refractive layer and the high refractive layer have a constitutions wherein ultramicroparticles of a high refractive inorganic compound having an average particle size of 100 nm or less are dispersed in a matrix material. As the ultramicroparticles of a high refractive inorganic compound, use can be preferably made of an inorganic compound having a refractive index of 1.65 or more such as an oxide of Ti, Zn, Sb, Sn, Zr, Ce, Ta, La, In, etc, or a composite oxide containing such a metal atom.

These ultramicroparticles may be used in the state of, for example, having been surface-treated with a surface treatment agent (for example, silane coupling agents disclosed in JP-A-11-295503, JP-A-11-153703, JP-A-2000-9908, etc.; or anionic compounds or organic metal coupling agents disclosed in JP-A-2001-310432, etc.), having a core-shell structure carrying high refractive particles as cores (JP-A-2001-166104, etch), or using together a particular dispersant (for example, JP-A-11-153703, U.S. Pat. No. 6,210,858B1, JP-A-2002-2776069, etc.) and so on.

As the matrix material, use may be made of a known thermoplastic resin, a hardening resin coating, etc. Also, use can be made of a polyfunctional material disclosed in JP-A-2000-47004, JP-A-2001-315242, JP-A-2001-31871, JP-A-2001-296401, etc. or a hardening film obtained from a metal alkoxide composition as disclosed in JP-A-2001-293818, etc.

The refractive index of the high refractive layer is preferably from 1.70 to 2.20. The thickness of the high refractive layer is preferably from 5 nm to 10 μm, and more preferably from 10 nm to 1 μm.

The refractive index of the middle refractive layer is controlled at a value between those of the low refractive layer and the high refractive layer. The refractive index of the middle refractive layer is preferably from 1.50 to 1.70.

It is preferable that the haze of the antireflection film is 5% or less, and more preferably 3% or less. The strength of the film is preferably H or more, more preferably 2H or more, and most preferably 3H or more, in a pencil hardness test in accordance with JIS K5400.

(Brightness Increasing Film)

In the invention, the polarizing plate may be used in combination with a brightness increasing film. The brightness increasing film, which has a function of separating a circular polarized light or a linearly polarized light, is placed between the polarizing plate and a backlight and reflects or scatters one circular polarized light or linearly polarized light backward to the backlight. The light re-reflected by the backlight undergoes a partial change in the polarization state and is partly transmitted through the brightness increasing film and the polarizing plate upon the injection thereinto. By repeating this process, the light utilization ratio is increased and thus the front brightness is elevated by about 1.4 times. As such a brightness increasing film, there have been known an anisotropy reflection type film and an anisotropy scattering type film both of which can be combined with the polarizing plate according to the invention.

In the anisotropy reflection type, there has been known a brightness increasing film in which a uniaxially stretched films and unstretched films are laminated to enlarge the refractive index difference in the stretch direction, thereby achieving a reflectivity and a transmittance anisotropy. Known examples of such brightness increasing films include multilayer films using the theory of dielectric mirror (disclosed in WO 95/17691, WO 95/17692 and WO 95/17699) and cholesteric liquid crystal films (disclosed in EP No. 606940A2 and JP-A-8-271731). In the invention, use is preferably made of DBEF-E, DBEF-D and DBEF-M (each manufactured by 3M) as the multilayer brightness increasing film using the theory of dielectric mirror principle, while NIPOCS (manufactured by Nitto Denko Corporation) is preferably used as the cholesteric liquid crystal brightness increasing film. Concerning NIPOCS, reference may be made to Nitto Giho, Vol. 38, No. 1, May 200, p. 19 to 21, etc.

In the invention, it is also preferable to use an anisotropy scattering type brightness increasing film, which is prepared by blending a positive intrinsic birefringence polymer and a negative intrinsic birefringence polymer and by uniaxial stretching as disclosed in WO 97/32223, WO 97/32224, WO 97/32225, WO 97/32226, JP-A-9-274108, and JP-A-11-174231, in combination. As the anisotropy scattering type brightness increasing film, DRPF-H (manufactured by 3M) is preferred.

(Other Functional Optical Films)

It is preferable that the polarizing plate according to the invention is used in combination with a functional optical film having a hard coating layer, a forward scattering layer, an antiglare (antidazzle) layer, a gas barrier layer, a slipping layer, an antistatic layer, an undercoat layer, a protective layer, etc. It is also preferred that these functional layers are combined with the antireflection layer of the antireflection film or the optically anisotropic layer within a single layer. These functional layers may be provided on either or both of the polarizer side and the opposite side (i.e., close to the air interface).

[Hard Coating Layer]

In the invention, it is a preferable practice to combine the polarizing plate with a functional optical film provided with a hard coating layer on a transparent support to thereby improve the mechanical strength such as scratch resistance. In the case of applying the hard coating layer to the above-described antireflection film, in particular, it is preferable that the hard coating layer is formed between the transparent support and the high refractive layer.

It is preferable to form the hard coating layer by a crosslinking reaction of a hardening compound by light and/or heat, or a polymerization reaction. A photopolymerizable group is preferable as a hardening functional group, while an organic alkoxysilyl compound is preferable as a hydrolyzable functional group-containing organic metal compound. Concerning the specific composition of the hard coating layer, use can be preferably made of those disclosed in JP-A-2002-144913, JP-A-2000-9908 and WO 00/46617, etc.

The thickness of the hard coating layer is preferably from 0.2 to 100 μm.

The strength of the hard coating layer is preferably H or more, more preferably 2H or more, and most preferably 3H or more, by a pencil hardness test in accordance with JIS K5400. Further, it is more preferable that the hard coating layer shows a smaller abrasion in a test piece before and after a taber test according to JIS K5400.

As the material for forming the hard coating layer, use can be made of a compound having an unsaturated ethylenic group and a compound having a ring opening polymerizable group. Either a single compound or a combination of such compounds may be used. Preferable examples of the compound having an unsaturated ethylenic group include polyol polyacrylates such as ethyleneglycol diacrylate, trimethylolpropane triacrylate, ditrimethylolpropane tetraacrylate, pentaerythritol triacrylate, pentaerythritol tetraacrylate, dipentaerythritol pentaacrylate and dipentaerythritol hexaacrylate; epoxy acrylates such as diacrylate of bisphenol A diglycidyl ether and diacrylate of hexanediol diglycidyl ether; and urethane acrylates obtained by a reaction of a polyisocyanate and a hydroxyl-containing acrylate such as hydroxyethyl acrylate. Examples of commercially available compounds include EB-600, EB-40, EB-140, EB-1150, EB-12901K, IRR214, EB-2220, TMPTA and TMPTMA (each manufactured by Daicel ucb), and UV-6300 and UV-1700B (each manufactured by Nippon Synthetic Chemical Industry Co., Ltd).

Preferable examples of the compound having a ring opening polymerizable group include glycidyl ethers such as ethylene glycol diglycidyl ether, bisphenol A diglycidyl ether, trimethylolethane triglycidyl ether, trimethylolpropane triglycidyl ether, glycerol triglycidyl ether, triglycidyl trishydroxyethyl isocyanurate, sorbitol tetraglycidyl ether, pentaerythritol tetraglycidyl ether, polyglycidyl ethers of cresol novolac resins and polyglycidyl ethers of phenol novolac resins; alicyclic epoxys such as CELOXIDE 2021P, CELOXIDE 2081, EPOLEAD GT-301, EPOLEAD GT-401, and EHPE3150CE (each manufactured by Daicel Chemical Industries, Ltd.), and polycyclohexyl epoxymethyl ether of phenol novolac resins; oxetanes such as OXT-121, OXT-221, OX-SQ, and PNOX-1009 (each manufactured by Toagosei Co., Ltd.). Further, polymers of glycidyl(meth)acrylate, and copolymers of glycidyl(meth)acrylate with a monomer copolymerizable therewith may be used for the hard coating layer.

In the hard coating layer, it is a preferable practice to employ microparticles of oxides of silicon, titanium, zirconium, aluminum, etc., crosslinked particles of polyethylene, polystyrene, poly(meth)acrylates, polydimethylsiloxane, etc., and crosslinked microparticles such as organic microparticles of crosslinked rubber, e.g., SBR, NBR, etc. to reduce hardening shrinkage of the hard coating layer, increase the adhesion thereof to the substrate, and reduce curling of the hard-coated article. The average particle size of these crosslinked microparticles is preferably from 1 to 20,000 nm. The shape of the crosslinked microparticles may be a spherical shape, rod-shaped shape, needle-like shape, tabular shape, etc without specific restriction. It is preferable that the microparticles are added in such an amount that the microparticle content of the hardened hard coating layer is 60% by volume or less, and more preferably 40% by volume or less.

The above described inorganic microparticles are generally poor in affinity for binder polymers. In the case of adding these inorganic microparticles, therefore, it is preferable to conduct a surface treatment by using a surface treatment agent having a metal such as silicon, aluminum or titanium, and a functional group such as an alkoxide group, a carboxylic acid group, a sulfonic acid group, or a phosphonic acid group.

It is preferable that the hard coating layer is hardened by using heat or an activation energy ray. It is more preferable to use an activation energy ray such as a radioactive ray, a gamma ray, an alpha ray, an electron ray, or a ultraviolet ray therefor, and particularly preferably by an electron ray or a ultraviolet ray in view of safety and productivity. In the case of the heat hardening, the heating temperature is preferably 140° C. or lower, and more preferably 100° C. or lower, in view of the heat resistance of the plastic per se.

[Forward Scattering Layer]

The forward scattering layer is used for improving the viewing angle properties (the hue and brightness distribution) in the directions of up/down, and right/left, of the liquid crystal display device to which the polarizing plate according to the invention is mounted. In the invention, it is preferable that the forward scattering layer is composed of microparticles with different refractive indexes dispersed in a binder. For example, use can be made of the forward scattering layer having a structure wherein the forward scattering coefficient is particularly specified as described in JP-A-11-38208, the relative refractive index between a transparent resin and microparticles is controlled within a specific range as described in JP-A-2000-199809, or the haze is controlled to 40% or more as described in JP-A-2002-107512. It is also preferable that the polarizing plate of the invention is used in combination with LUMISTY (described in Sumitomo Chemical Con, Ltd., Technical Report, *Ko-kinosei Firumu (Optical functional film)*, p. 31 to 39) to thereby control the haze viewing angle properties.

[Antiglare Layer]

The antiglare (antidazzle) layer is used for scattering a reflected light to thereby prevent external light reflection. The antiglare function is achieved by forming peaks and valleys on the outermost surface of the liquid crystal display device. The haze of the optical film having the antiglare function is preferably 3 to 30%, more preferably 5 to 20%, and most preferably 7 to 20%.

To form the peaks and valleys on the film surface, use may be preferably made of, for example, a method of adding microparticles (see, for example, JP-A-2000-271878, etc.), a method of adding a small amount (0.1 to 50% by mass) of relatively large particles having a size of 0.05 to 2 μm to thereby form a film having peaks and valleys on the surface (JP-A-2000-281410, JP-A-2000-95893, JP-A-2001-100004, JP-A-2001-281407, etc.), or a method of physically transferring the peaks and valleys to the film surface (see, for example, an embossing method disclosed in JP-A-63-278839, JP-A-11-183710, JP-A-2000-275401, etc.).

<Liquid Crystal Display Device>

Next, the liquid crystal display device according to the invention will be described.

The liquid crystal display device according to the invention has the polarizing plate according to the invention.

FIG. 1 is a schematic view showing an example of the liquid crystal display device according to the invention. In FIG. 1, a liquid crystal display device 10 comprises a liquid crystal cell containing a liquid crystal layer 7 and an upper electrode substrate 5 and a lower electrode substrate 8 respectively provided thereabove and therebelow, and an upper polarizing plate 1 and a lower polarizing plate 12 provided on the both sides of the liquid crystal cells. Optionally, a color filter may be provided between the liquid crystal cell and each of the polarizing plates. In the case where the liquid crystal display device 10 is employed as a transmission type device, it is equipped with a backlight using a light source such as a cold or hot cathode fluorescent tube, a light emitting diode, a field emission device or an electroluminescent device on the back side.

Each of the upper polarizing plate 1 and the lower polarizing plate 12 has a laminated structure wherein a polarizer is interposed between two protective films. In the liquid crystal display device 10 of the invention, the protective film on the liquid crystal cell side of one of the polarizing plates satisfies the characteristics of the formulae (1) to (3) as described above.

The liquid crystal display device 10 includes an image direct-view type, an image projection type and a light modulation type. The invention can be applied effectively to an active matrix liquid crystal display device using a 3-terminal or 2-terminal semiconductor element such as a TFT or an MIM. Needless to say, it is also effectively applicable to a passive matrix liquid crystal display device represented by an STN mode called time division driving.

In FIG. 1, 2 represents the direction of the upper polarizing plate absorption axis, 6 represents the alignment control direction of the upper substrate, 9 represents the alignment control direction of the lower substrate, and 13 represents the direction of the lower polarizing plate absorption axis.

In addition, the liquid crystal display device 10 of the invention has preferably an optically compensatory film that satisfies the following formulae (4) and (5) for the protective film having the characteristics of the above-described formulae (1) to (3) on the opposite side to the liquid crystal cell.

$$20 \text{ nm} \leq Re(548) \leq 150 \text{ nm} \qquad \text{Formula (4)}$$

$$100 \text{ nm} \leq Rth(548) \leq 400 \text{ nm} \qquad \text{Formula (5)}$$

In the formula (4), Re(548) is further preferably from 30 nm to 150 nm, and most preferably from 40 nm to 150 nm. In the formula (5), Rth(548) is further preferably from 100 nm to 300 nm, and most preferably from 100 nm to 250 nm.

Optically Compensatory Film

Next, an optically compensatory film that satisfies the formulae (4) and (5) will described in detail. It is preferable that the optically compensatory film of the invention is one that comprises at least one of a cellulose acylate-based resin, a polycarbonate-based resin, a polyimide-based resin, a polyetherketone-based resin, a polycycloolefin-based resin and a polyvinyl acetal-based resin. More specifically, use can be preferably made of one having a non-liquid crystalline polymer such as polyimide or polyaryletherketone on a substrate as described in JP-A-2003-344856, a stretched cellulose acylate film, a stretched film of a cycloolefin-based polymer and so on. As the cycloolefin-based polymer film, use can be preferably made of a polymer film using ZEONOR by ZEON, ARTON by JSR, APPEAR3000 by PROMERUS, etc. Among these polymer films, a stretched cellulose acylate film is especially preferred because of being excellent in processing suitability for a polarizing plate and inexpensive. Next, such a stretched cellulose acylate film preferably usable in the liquid crystal display device of the invention will be described in detail Cellulose Acylate The cellulose acylate that is contained mainly in the stretched cellulose acylate film has an acetyl substitution degree of preferably 2.50 to 3.00, and more preferably 2.70 to 2.95.

Another cellulose acylate that is preferable in the invention is a mixed aliphatic acid ester having the total acyl substitution degree of 2.00 to 2.90 and an acyl group having 3 to 4 carbon atoms. The substitution degree of the acyl group having 3 to 4 carbon atoms is preferably 0.1 to 2.0, and more preferably 0.3 to 1.5.

It is preferable that the cellulose acylate usable in the polymer film of the invention has an average polymerization degree of 250 to 800, and more preferably 280 to 600. It is also preferable that the cellulose acylate usable in the polymer film of the invention has a number average molecular weight of preferably 70,000 to 230,000, more preferably 75,000 to 230,000, and more preferably 78,000 to 120,000.

The cellulose acylate to be used in the stretched cellulose acylate film of the invention can be synthesized in the same method as in the production of the cellulose acylate to be used in the normal wavelength dispersion cellulose acylate film as described above.

In the invention, the cellulose acylate film may contain one or more kinds of retardation developing agents. The adding one or more kinds of retardation developing agents contributes to the satisfaction of the relationships represented by the formulae (4) and (5). As the retardation developing agent, use may be preferably made of a compound represented by the following formula (III) and/or a compound represented by the following formula (IV) and the addition of a compound represented by the following formula (IV) is still preferred.

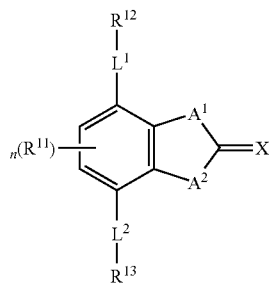

Formula (III)

In the formula (III), $L^1$ and $L^2$ each independently represents a single bond or a divalent linking group. $A^1$ and $A^2$ each independently represents a group that is selected from the group consisting of —O—, —NR— (wherein R represents a hydrogen atom or a substituent), —S— and —CO—, $R^{11}$, $R^{12}$ and $R^{13}$ each independently represents a substituent. X represents a nonmetal atom of 14 to 16 groups (provided that X may be a nonmetal atom of 14 to 16 group that is bonded with a hydrogen atom or a substituent). n represents 0 or an integer of 1 to 2.

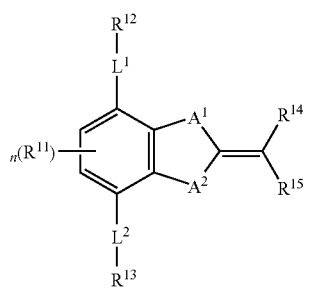

Formula (IV)

In the formula (IV), $L^1$, $L^2$, $A^1$, $A^2$, $R^{11}$, $R^{12}$ and $R^{13}$ are each as defined in the formula (III) $R^{14}$ and $R^{15}$ each independently represents a substituent n represents 0 or an integer of 1 to 2.

In the formula (III) or (IV), preferable examples of the divalent linking groups represented by $L^1$ and $L^2$ are as follows.

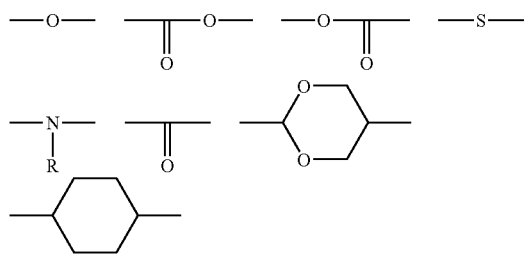

Further preferred are —O—, —COO— and —OCO—.

In the formula (III) or (IV), $R^{11}$ represents a substituent, and, in case where plural $R^{11}$s exist, they may be the same or different from each other, or form a ring. Examples of the substituent are as follows:

a halogen atom (for example, a fluorine atom, a chlorine atom, a bromine atom, an iodine atom), an alkyl group (preferably an alkyl group having 1 to 30 carbon atoms such as a methyl group, an ethyl group, an n-propyl group, an isopropyl group, a tert-butyl group, an n-octyl group, a 2-ethylhexyl group), a cycloalkyl group (preferably a substituted or unsubstituted cycloalkyl group having 3 to 30 carbon atoms such as a cyclohexyl group, a cyclopentyl group, a 4-n-dodecylcyclohexyl group), a bicycloalkyl group (preferably a substituted or unsubstituted bicycloalkyl group having 5 to 30 carbon atoms, i.e., a monovalent group that is formed by removing one hydrogen atom from a bicycloalkane having 5 to 30 carbon atoms, such as a bicyclo[1,2,2]heptane-2-yl group, a bicyclo[2,2,2]octane-3-yl group), an alkenyl group (preferably a substituted or unsubstituted alkenyl group having 2 to 30 carbon atoms such as a vinyl group, an allyl group), a cycloalkenyl group (preferably a substituted or unsubstituted cycloalkenyl group having 3 to 30 carbon atoms, i.e., a monovalent group that is formed by removing one hydrogen atom from a cycloalkene having 3 to 30 carbon atoms, such as a 2-cyclopentene-1-yl group, a 2-cyclohexene-1-yl group), a bicycloalkenyl group (a substituted or unsubstituted bicycloalkenyl group, preferably a substituted or unsubstituted bicycloalkenyl group having 5 to 30 carbon atoms, i.e., a monovalent group that is formed by removing one hydrogen atom from a bicycloalkene having one double bond, such as a bicyclo [2,2,1]hept-2-ene-1-yl group, a bicyclo[2,2,2]oct-2-ene-4-yl group), an alkynyl group (preferably a substituted or unsubstituted alkynyl group having 2 to 30 carbon atoms such as an ethynyl group, propargyl group), an aryl group (preferably a substituted or unsubstituted aryl group having 6 to 30 carbon atoms such as a phenyl group, a p-tolyl group, a naphthyl group), a heterocyclic group (preferably a monovalent group that is formed by removing one hydrogen atom from a 5-membered or 6-membered, substituted or unsubstituted, aromatic or nonaromatic heterocyclic compound or a combination thereof (including a condensed ring), more preferably a monovalent group that is formed by removing one hydrogen atom from a 5-membered or 6-membered heterocyclic compound having 3 to 30 carbon atoms or a combination thereof (including a condensed ring), such as a 2-furyl group, a 2-thienyl group, a 2-pyrimidinyl group, a 2-benzothiazolyl group), a cyano group, a hydroxyl group, a nitro group, a carboxyl group, an alkoxy group (preferably a substituted or unsubstituted alkoxy group having 1 to 30 carbon atoms such as a methoxy group, an ethoxy group, an isopropoxy group, a tert-butoxy group, an n-octyloxy group, a 2-methoxyethoxy group), an aryloxy group (preferably a substituted or unsubstituted aryloxy group having 6 to 30 carbon atoms such as a phenoxy group, a 2-methylphenoxy group, a 4-tert-butylphenoxy group, a 3-nitrophenoxy group, a 2-tetradecanoylaminophenoxy group), a silyloxy group (preferably a silyloxy group having 3 to 20 carbon atoms such as a trimethylsilyloxy group, a tert-butyldimethylsilyloxy group), a heterocyclicoxy group (preferably a substituted or unsubstituted heterocyclicoxy group having 2 to 30 carbon atoms such as a 1-phenyltetrazole-5-oxy group, a 2-tetrahydropyranyloxy group), an acyloxy group (preferably a formyloxy group, a substituted or unsubstituted alkylcarbonyloxy group having 2 to 30 carbon atoms, a substituted or unsubstituted arylcarbonyloxy group having 6 to 30 carbon atoms such as a formyloxy group, an acetyloxy group, a pivaloyloxy group, a stearoyloxy group, a benzoyloxy group, a p-methoxyphenylcarbonyloxy group), a carbamoyloxy group (preferably a substituted or unsubstituted carbamoyloxy group having 1 to 30 carbon atoms such as an N,N-dimethylcarbamoyloxy group, an N,N-diethylcarbamoyloxy group, a morpholinocarbonyloxy group, an N,N-di-n-octylaminocarbonyloxy group, an N-n-octylcarbamoyloxy group), an alkoxycarbonyloxy group (preferably a substituted or unsubstituted alkoxycarbonyloxy group having 2 to 30 carbon atoms such as a methoxycarbonyloxy group, an ethoxycarbonyloxy group, a tert-butoxycarbonyloxy group, an n-octylcarbonyloxy group), an aryloxycarbonyloxy group (preferably a substituted or unsubstituted aryloxycarbonyloxy group having 7 to 30 carbon atoms such as a phenoxycarbonyloxy group, a p-methoxyphenoxycarbonyloxy group, a p-n-hexadecyloxyphenoxycarbonyloxy group), an amino group (preferably an amino group, a substituted or unsubstituted alkylamino group having 1 to 30 carbon atoms, a substituted or unsubstituted anilino group having 6 to 30 carbon atoms such as an amino group, a methylamino group, a dimethylamino group, an anilino group, an N-methylanilino group, a diphenylamino group), an acylamino group (preferably a formylamino group, a substituted or unsubstituted alkylcarbonylamino group having 1 to 30 carbon atoms, a substituted or unsubstituted arylcarbonylamino group having 6 to 30 carbon atoms such as a formylamino group, an acetylamino group, a pivaloylamino group, a lauroylamino group, a benzoylamino group), an aminocarbonylamino group (preferably a substituted or unsubstituted aminocarbonylamino group having 1 to 30 carbon atoms such as a carbamoylamino group, an N,N-dimethylaminocarbonylamino group, an N,N-diethylaminocarbonylamino group, a morpholinocarbonylamino group), an alkoxy carbonylamino group (preferably a substituted or unsubstituted alkoxycarbonylamino group having 2 to 30 carbon atoms such as a methoxycarbonylamino group, an ethoxycarbonylamino group, a tert-butoxycarbonylamino group, an n-octadecyloxycarbonylamino group, an N-methylmethoxycarbonylamino group), an aryloxycarbonylamino group (preferably a substituted or unsubstituted aryloxycarbonylamino group having 7 to 30 carbon atoms such as a phenoxycarbonylamino group, a p-chlorophenoxycarbonylamino group, an m-n-octyloxyphenoxycarbonylamino group), a sulfamoylamino group (preferably a substituted or unsubstituted sulfamoylamino group having 0 to 30 carbon atoms such as a sulfamoylamino group, an N,N-dimethylaminosulfonylamino group, an N-n-octylaminosulfonylamino group), an alkylsulfonylamino group/arylsulfonylamino group (preferably a substituted or unsubstituted alkylsulfonylamino group having 1 to 30 carbon atoms/a substituted or unsubstituted arylsulfonylamino group having 6 to 30 carbon atoms such as a methylsulfonylamino group, a butlysulfonylamino group, a phenylsulfonylamino group, a 2,3,5-trichlorophenylsulfonylamino group, a p-methylphenylsulfonylamino group), a mercapto group, an alkylthio group (preferably a substituted or unsubstituted alkylthio group having 1 to 30 carbon atoms such as a methylthio group, an ethylthio group, an n-hexadecylthio group), an arylthio group (preferably a substituted or unsubstituted arylthio group having 6 to 30 carbon atoms such as a phenylthio group, a p-chlorophenylthio group, an m-methoxyphenylthio group), a heterocyclicthio group (preferably a substituted or unsubstituted heterocyclicthio group having 2 to 30 carbon atoms such as a 2-benzothiazolylthio group, a 1-phenyltetrazole-5-ylthio group), a sulfamoyl group (preferably a substituted or unsubstituted sulfamoyl group having 0 to 30 carbon atoms such as an N-ethylsulfamoyl group, an N-(3-dodecyloxypropyl)sulfamoyl group, an N,N-dimethylsulfamoyl group, an N-acetylsulfamoyl group, an N-benzoylsulfamoyl group, an N—(N'-phenylcarbamoyl)sulfamoyl group), a sulfo group, an alkylsulfinyl group/arylsulfinyl group (preferably a substituted or unsubstituted alkylsulfinyl group having 1 to 30 carbon atoms/a substituted or unsubstituted arylsulfinyl group having 6 to 30 carbon atoms such as a methylsulfinyl group, an ethylsulfinyl group, a phenylsulfinyl group, a p-methylphenylsulfinyl group), an alkylsulfonyl group/arylsulfonyl group (preferably a substituted or unsubstituted alkylsulfonyl group having 1 to 30 carbon atoms/a substituted or unsubstituted arylsulfonyl group having 6 to 30 carbon atoms such as a methylsulfonyl group, an ethylsulfonyl group, phenylsulfonyl group, a p-methylphenylsulfonyl group), an acyl group (preferably a formyl group, a substituted or unsubstituted alkylcarbonyl group having 2 to 30 carbon atoms, a substituted or unsubstituted arylcarbonyl group having 7 to 30 carbon atoms such as an acetyl group, a pivaloylbenzoyl group), an aryloxycarbonyl group (preferably a substituted or unsubstituted aryloxycarbonyl group having 7 to 30 carbon atoms such as a phenoxycarbonyl group, an o-chlorophenoxycarbonyl group, an m-nitrophenoxycarbonyl group, a p-tert-butylphenoxycarbonyl group), an alkoxycarbonyl group (preferably a substituted or unsubstituted alkoxycarbonyl group having 2 to 30 carbon atoms such as a methoxycarbonyl group, an ethoxycarbonyl group, a tert-butoxycarbonyl group, an n-octadecyloxycarbonyl group), a carbamoyl group (preferably a substituted or unsubstituted carbamoyl group having 1 to 30 carbon atoms such as a carbamoyl group, an N-methylcarbamoyl group, an N,N-dimethylcarbamoyl group, an N,N-di-n-octylcarbamoyl group, an N-(methylsulfonyl) carbamoyl group), an aryl and heterocyclic azo group (preferably a substituted or unsubstituted arylazo group having 6 to 30 carbon atoms, a substituted or unsubstituted heterocyclic azo group having 3 to 30 carbon atoms such as a phenylazo group, a p-chlorophenylazo group, a 5-ethylthio-1,3,4-thiadiazole-2-ylazo group), an imido group (preferably an N-succinimido group, an N-phthalimido group), a phosphino group (preferably a substituted or unsubstituted phosphino group having 2 to 30 carbon atoms such as a dimethylphosphino group, a diphenylphosphino group, a methylphenoxyphosphino group), a phosphinyl group (preferably a substituted or unsubstituted phosphinyl group having 2 to 30 carbon atoms such as a phosphinyl group, a dioctyloxyphosphinyl group, a diethoxyphosphinyl group), a phosphinyloxy group (preferably a substituted or unsubstituted phosphinyloxy group having 2 to 30 carbon atoms such as a diphenoxyphosphinyloxy group, a dioctyloxyphosphinyloxy group), a phosphinylamino group (preferably a substituted or unsubstituted phosphinylamino group having 2 to 30 carbon atoms such as a dimethoxyphosphinylamino group, a dimethylaminophosphinylamino group), and a silyl group (preferably a substituted or unsubstituted silyl group having 3 to 30 carbon atoms such as a trimethylsilyl group, a tert-butyldimethylsilyl group, a phenyldimethylsilyl group).

In a hydrogen atom-containing substituent among the above-described ones, the hydrogen atom may be removed and substituted further with one of the above-described groups. Examples of such functional groups include an alkylcarbonylaminosulfonyl group, an arylcarbonylaminosulfonyl group, an alkylsulfonylaminocarbonyl group and an arylsulfonylaminocarbonyl group. Examples of these groups include a methylsulfonylaminocarbonyl group, a p-methylphenylsulfonylaminocarbonyl group, an acetylaminosulfonyl group, and a benzoylaminosulfonyl group.

$R^{11}$ is preferably a halogen atom, an alkyl group, an alkenyl group, an aryl group, a heterocyclic group, a hydroxyl group, a carboxyl group, an alkoxy group, an aryloxy group, an acyloxy group, a cyano group, or an amino group, and more preferably a halogen atom, an alkyl group, a cyano group or an alkoxy group.

$R^{12}$ and $R^{13}$ each independently represents a substituent. Examples of the substituent include those described for $R^{11}$. It is preferably an alkyl group, an alkenyl group, an aryl group, a heterocyclic group or an aryloxy group, more preferably a substituted or unsubstituted benzene ring or a substituted or unsubstituted cyclohexane ring, further preferably a benzene ring having a substituent or a cyclohexane ring having a substituent, and furthermore preferably a benzene ring having a substituent at the 4-position or a cyclohexane ring having a substituent at the 4-position. Especially preferred is a benzene ring having a benzoyloxy group, which has substituent at the 4-position, at the 4-position having; a benzene ring having a cyclohexyl group, which has substituent at the 4-position, at the 4-position; a cyclohexane ring having a benzene ring, which has substituent at the 4-position, at the 4-position; or a cyclohexane ring having a cyclohexyl group, which has substituent at the 4-position, at the 4-position. As the substituent, an alkyl group is preferred.

Although a cyclohexane ring having a substituent at the 4-position occurs as stereoisomers of cis from and trans form, the invention is not restricted to either of these stereoisomers. Also, a mixture thereof may be used. A trans-cyclohexane ring is preferred.

$R^{14}$ and $R^{15}$ each independently represents a substituent. The examples of the substituent are the same as those described for $R^{11}$. Among the substituents cited by way of example of $R^{11}$, an electron-withdrawing substituent having a Hammett's substituent constant σp value larger than 0 is preferable and an electron-withdrawing substituent having a Hammett's substituent constant σp value of 0 to 1.5 is more preferable. Examples of such substituents include a trifluoromethyl group, a cyano group, a carbonyl group, a nitro group and so on. $R^{14}$ and $R^{15}$ may be bonded to form a ring. Hammett's substituent constant σp and σm values are described in detail by, for example, Inamoto Naoki, *Hametto Soku—Kozo to Hannosei* (*Hammett's Rule—Structure and Reactivity*—), Maruzen; The Chemical Society of Japan Ed., *Shin Jikkenkagaku Koza* 14, *Yukikagobutsu no Gosei to Hannou V* (*New Course of Experimental Chemistry* 14, *Synthesis and Reaction of Organic Compound V*), p. 2605, Maruzen; Nakaya Tadao, *Riron Yukikagaku Kaisetsu* (*Interpretation of Theoretical Organic Chemistry*), p. 217, TOKYO KAGAKU DOJIN; and Chemical Review vol. 91, p., 165 to 195 (1991).

$A^1$ and $A^2$ each independently represents a group selected from the group consisting of —O—, —NR— (wherein R is a hydrogen atom or a substituent), —S— or —CO—. Among them, —O—, —NR— (wherein R represents a substituent examples of which include those cited above as examples of $R^{11}$) or —S— is preferable. It is preferable that at least one of $A^1$ and $A^2$ is —S—, and more preferably both $A^1$ and $A^2$ are —S—.

X is preferably O, S, NR or C(R)R (wherein R represents a substituent examples of which include those cited above as examples of $R^{11}$).

n is preferably 0 or 1.

Next, specific examples of the compounds represented by formula (III) or (IV) will be shown. However, it is to be understood that the invention is not limited by the following specific examples in any way. Unless otherwise noted, these compounds are shown as the "exemplified compound (X)" wherein X means the numeral in the parentheses ( ).

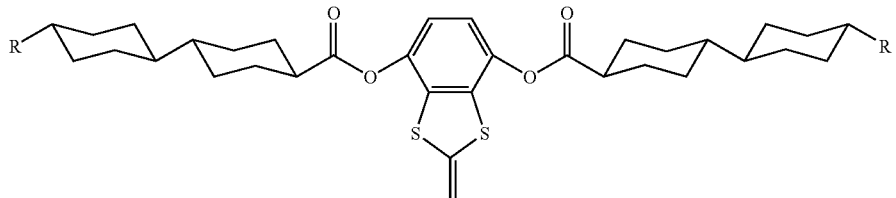

R = —$C_5H_{11}$
(1)
—$C_4H_9$
(2)
—$C_3H_7$
(3)
—$C_2H_5$
(4)

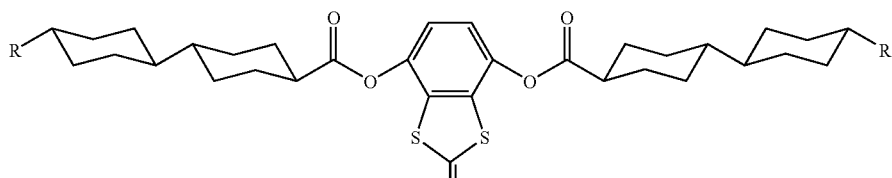

R = —$C_5H_{11}$
(5)
—$C_4H_9$
(6)
—$C_3H_7$
(7)
—$C_2H_5$
(8)

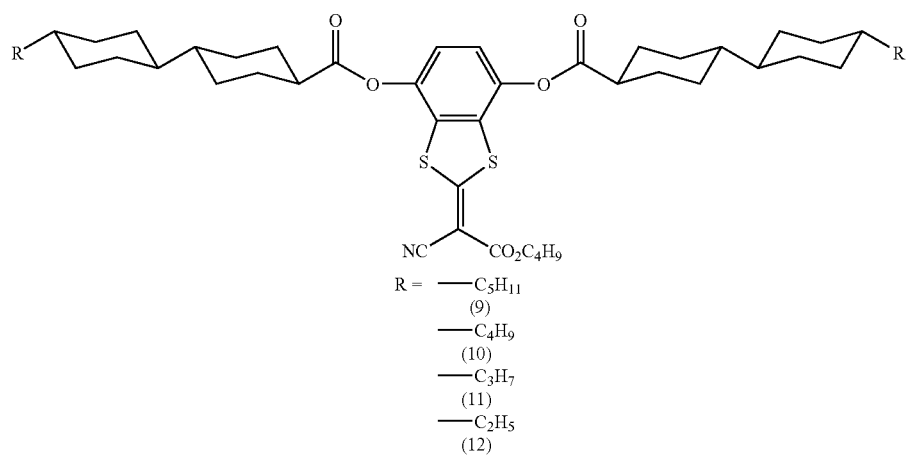
R = —C$_5$H$_{11}$ (9)
—C$_4$H$_9$ (10)
—C$_3$H$_7$ (11)
—C$_2$H$_5$ (12)
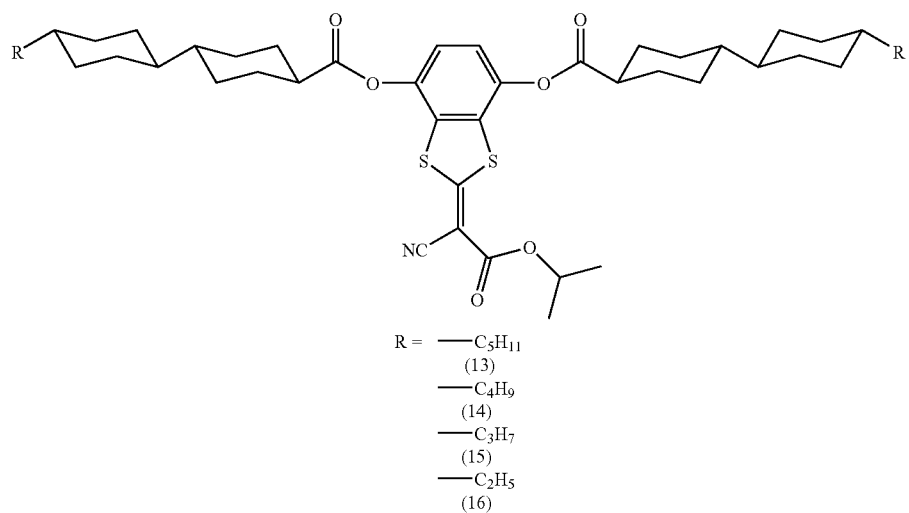
R = —C$_5$H$_{11}$ (13)
—C$_4$H$_9$ (14)
—C$_3$H$_7$ (15)
—C$_2$H$_5$ (16)
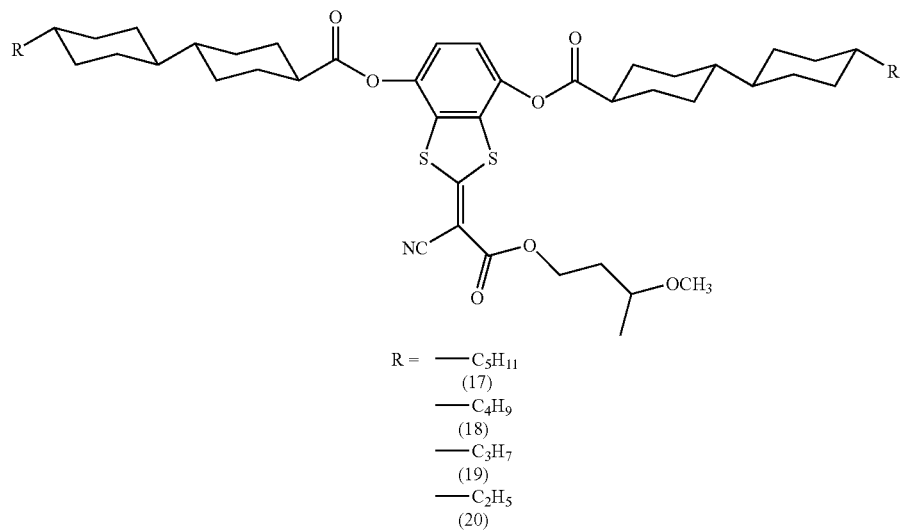
R = —C$_5$H$_{11}$ (17)
—C$_4$H$_9$ (18)
—C$_3$H$_7$ (19)
—C$_2$H$_5$ (20)

-continued
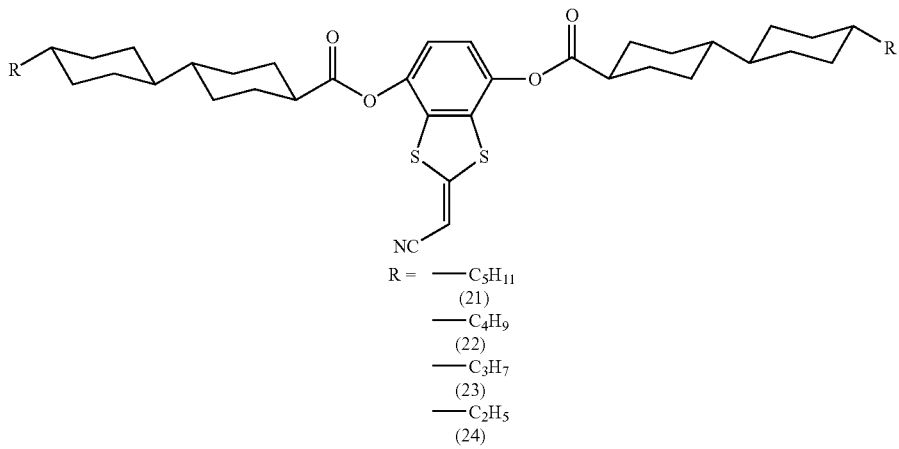
R = —C₅H₁₁ (21)
—C₄H₉ (22)
—C₃H₇ (23)
—C₂H₅ (24)
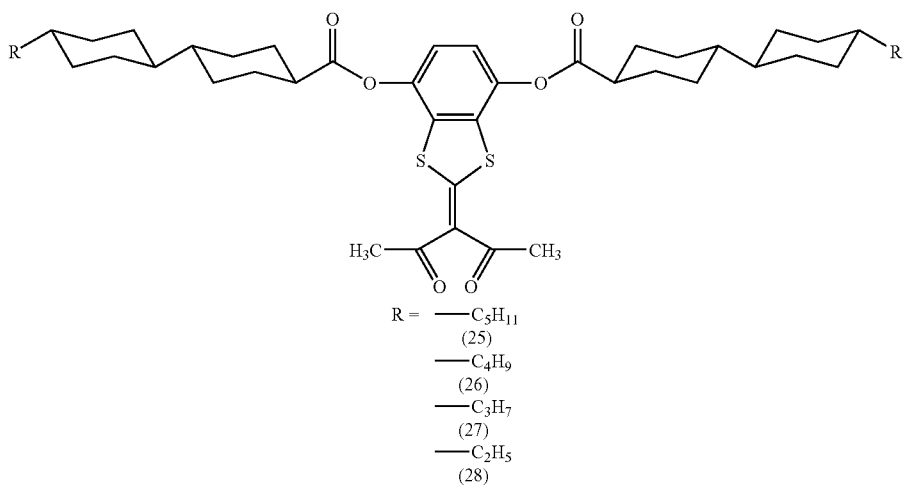
R = —C₅H₁₁ (25)
—C₄H₉ (26)
—C₃H₇ (27)
—C₂H₅ (28)
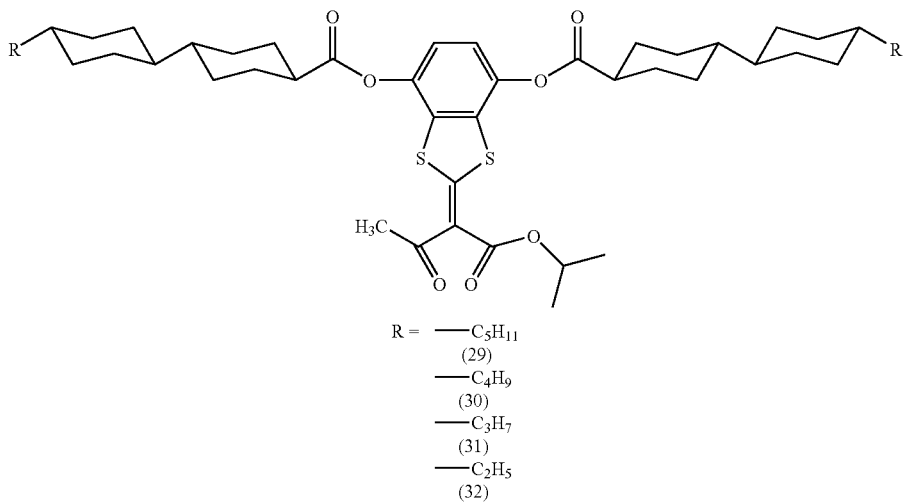
R = —C₅H₁₁ (29)
—C₄H₉ (30)
—C₃H₇ (31)
—C₂H₅ (32)

-continued
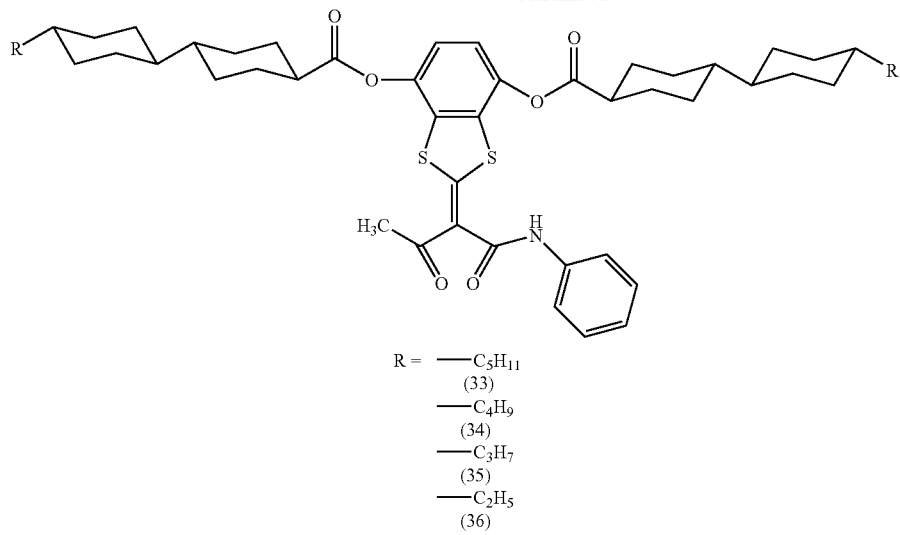
R = —C$_5$H$_{11}$ (33)
—C$_4$H$_9$ (34)
—C$_3$H$_7$ (35)
—C$_2$H$_5$ (36)
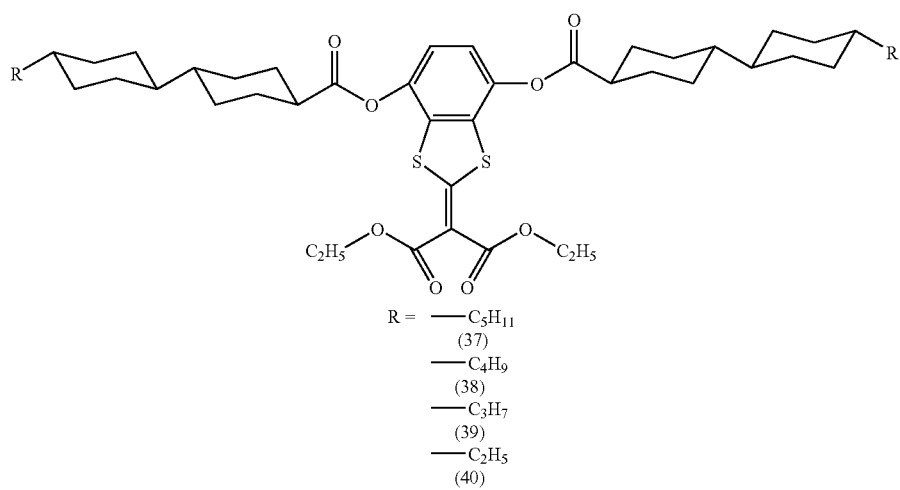
R = —C$_5$H$_{11}$ (37)
—C$_4$H$_9$ (38)
—C$_3$H$_7$ (39)
—C$_2$H$_5$ (40)
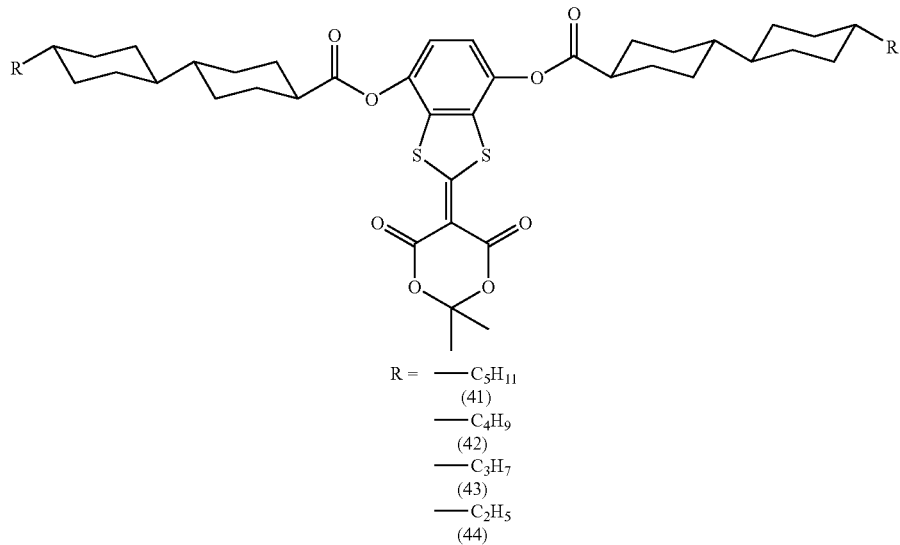
R = —C$_5$H$_{11}$ (41)
—C$_4$H$_9$ (42)
—C$_3$H$_7$ (43)
—C$_2$H$_5$ (44)

-continued
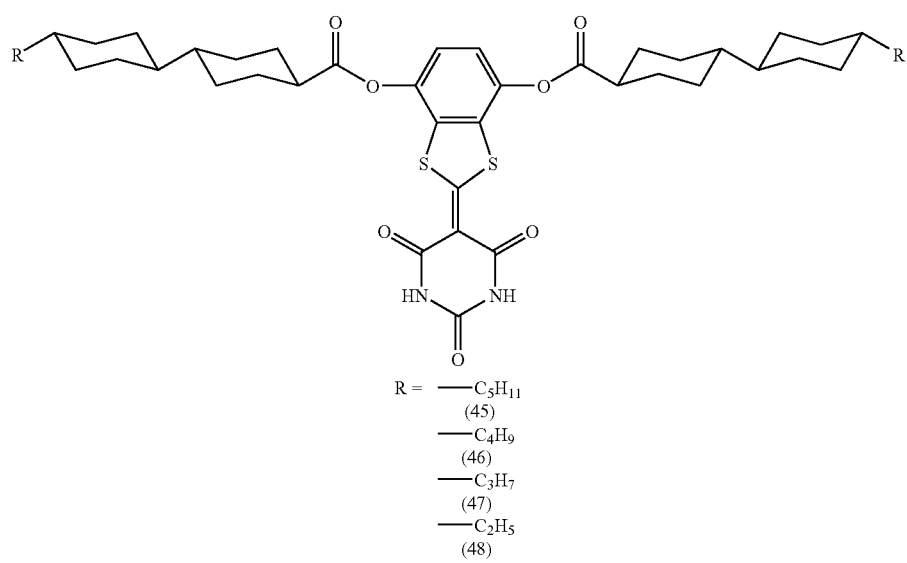
R = —C₅H₁₁ (45)
—C₄H₉ (46)
—C₃H₇ (47)
—C₂H₅ (48)
(49)
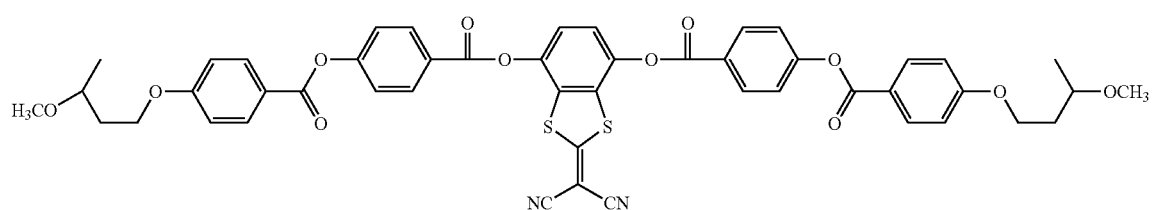
(50)
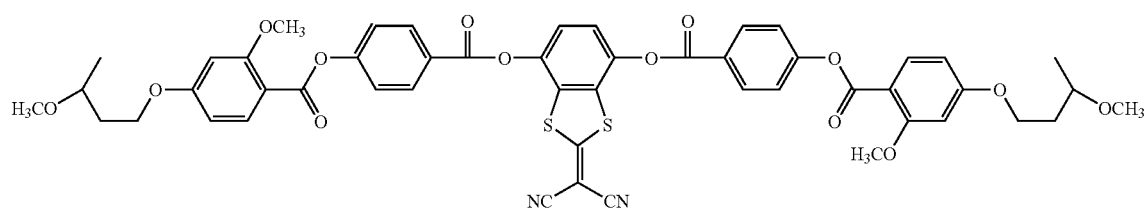
(51)
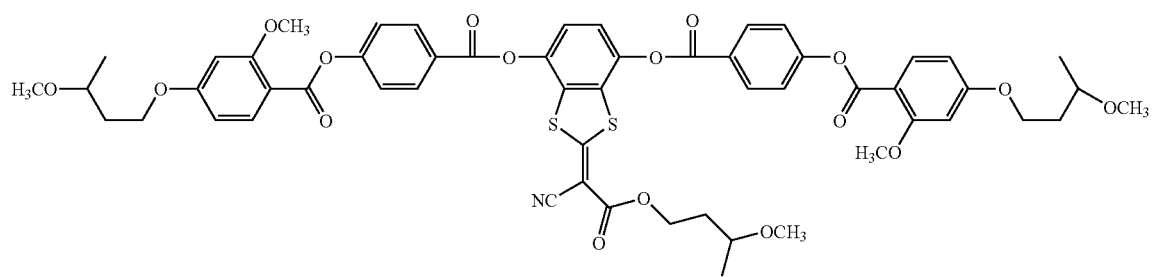
(52)
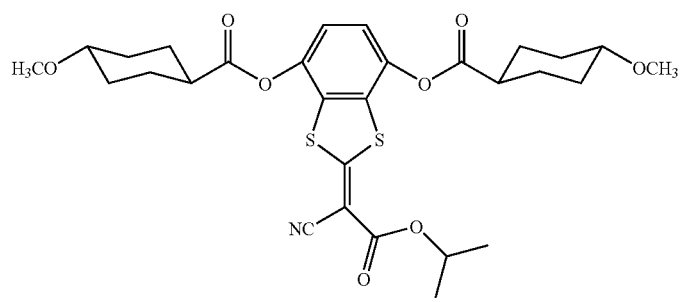

-continued
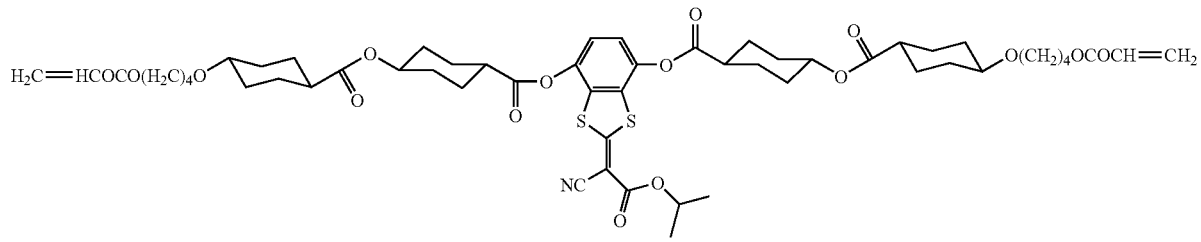
(53)
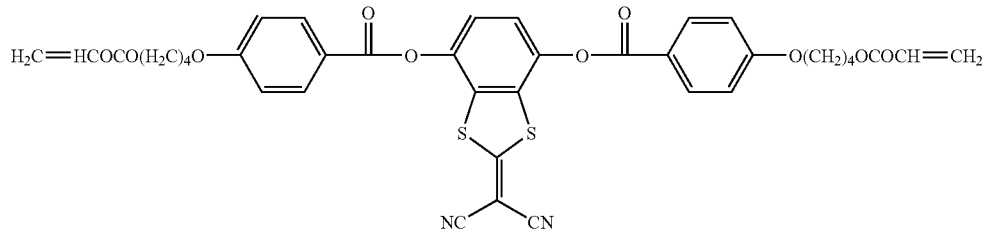
(54)
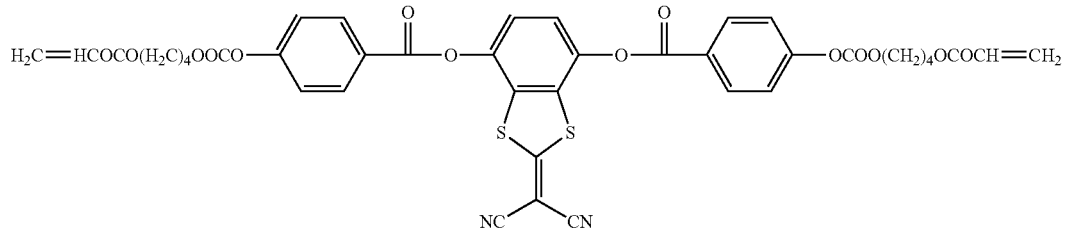
(55)
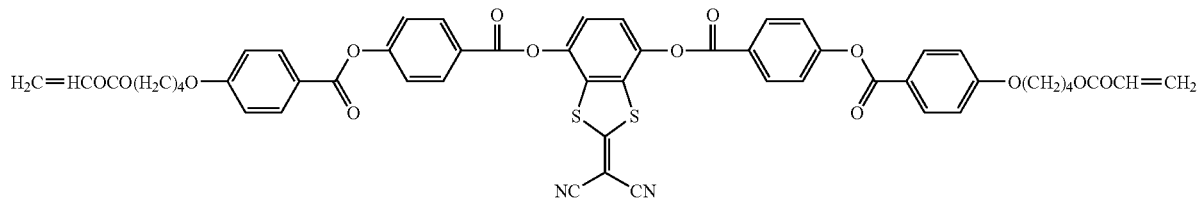
(56)
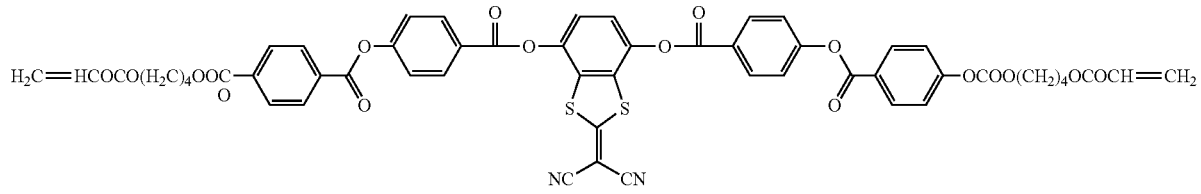
(57)
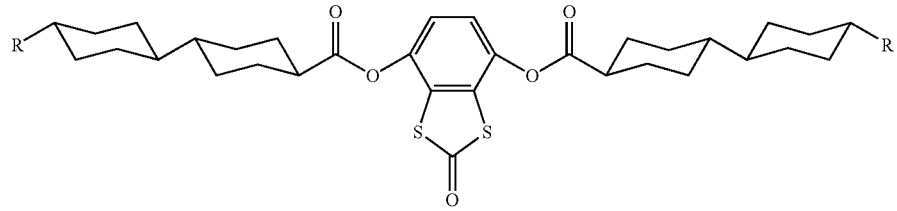
R = —$C_5H_{11}$
(58)
—$C_4H_9$
(59)
—$C_3H_7$
(60)
—$C_2H_5$
(61)

-continued
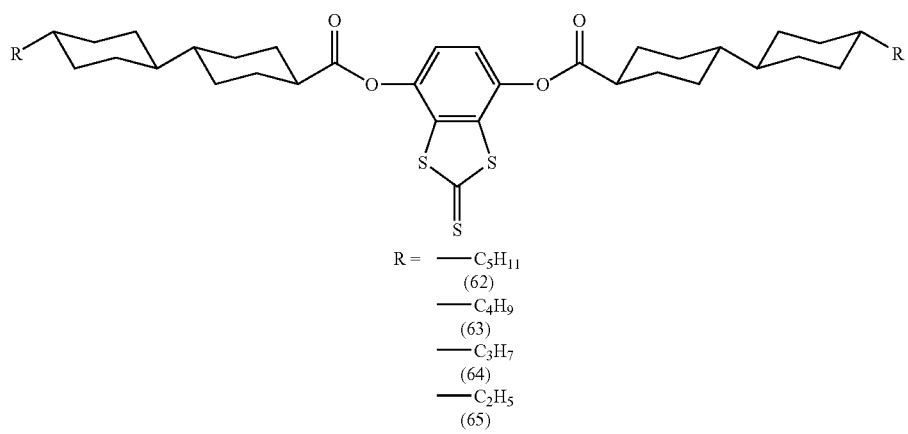
R = —C₅H₁₁ (62)
—C₄H₉ (63)
—C₃H₇ (64)
—C₂H₅ (65)
(66)
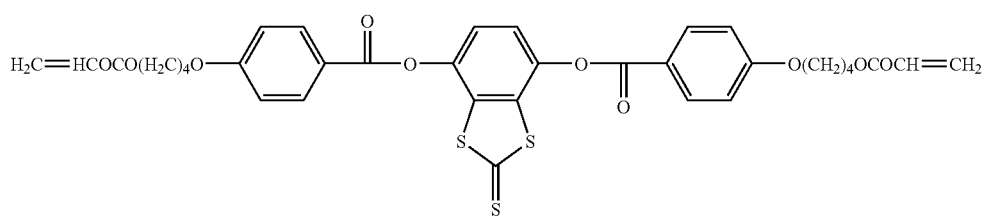
(67)
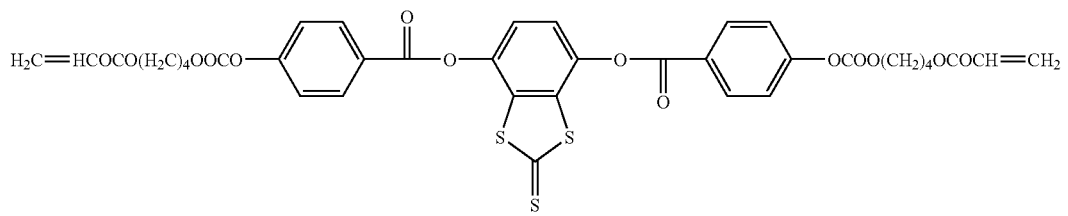
(68)
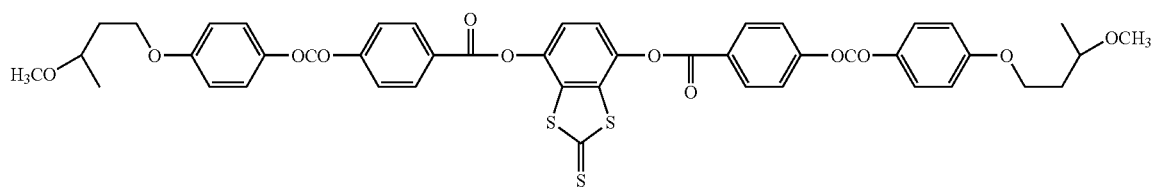
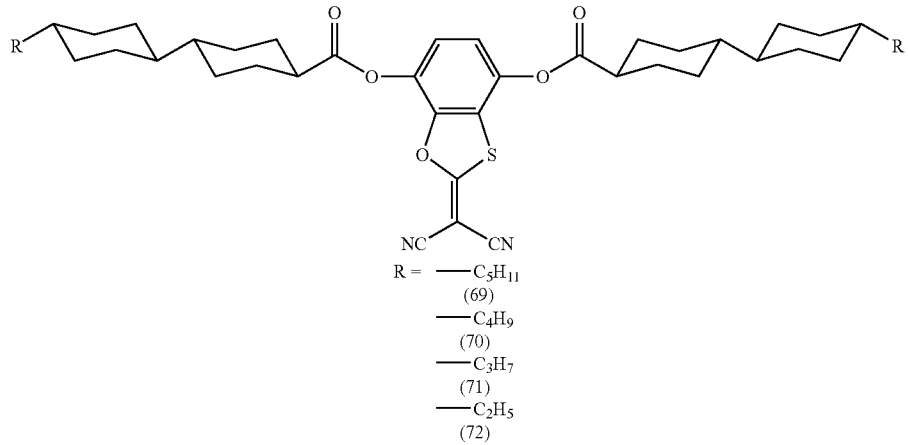
R = —C₅H₁₁ (69)
—C₄H₉ (70)
—C₃H₇ (71)
—C₂H₅ (72)

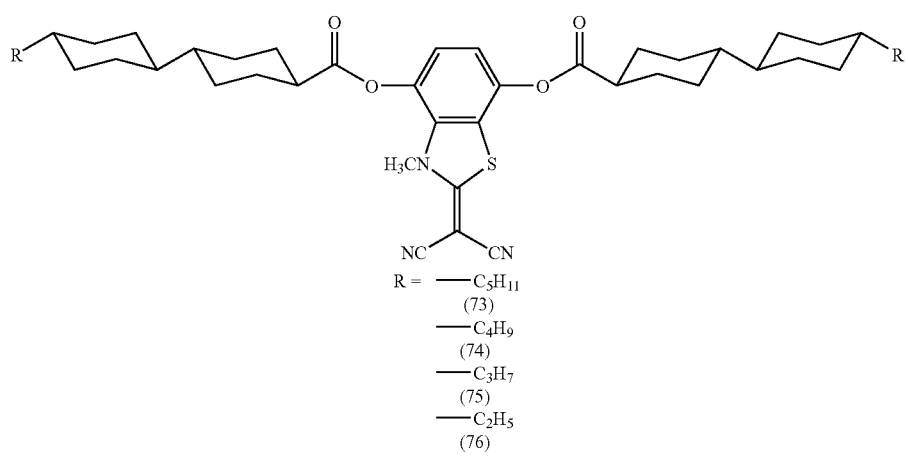
R = —C₅H₁₁ (73)
—C₄H₉ (74)
—C₃H₇ (75)
—C₂H₅ (76)
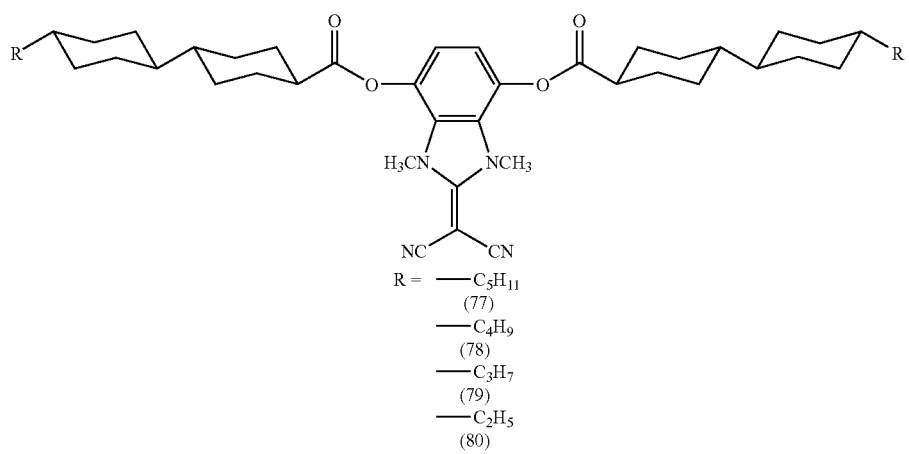
R = —C₅H₁₁ (77)
—C₄H₉ (78)
—C₃H₇ (79)
—C₂H₅ (80)
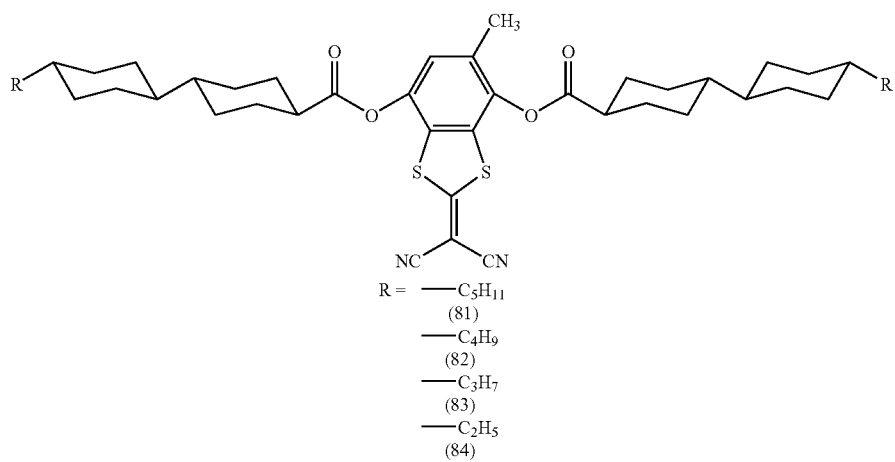
R = —C₅H₁₁ (81)
—C₄H₉ (82)
—C₃H₇ (83)
—C₂H₅ (84)

-continued
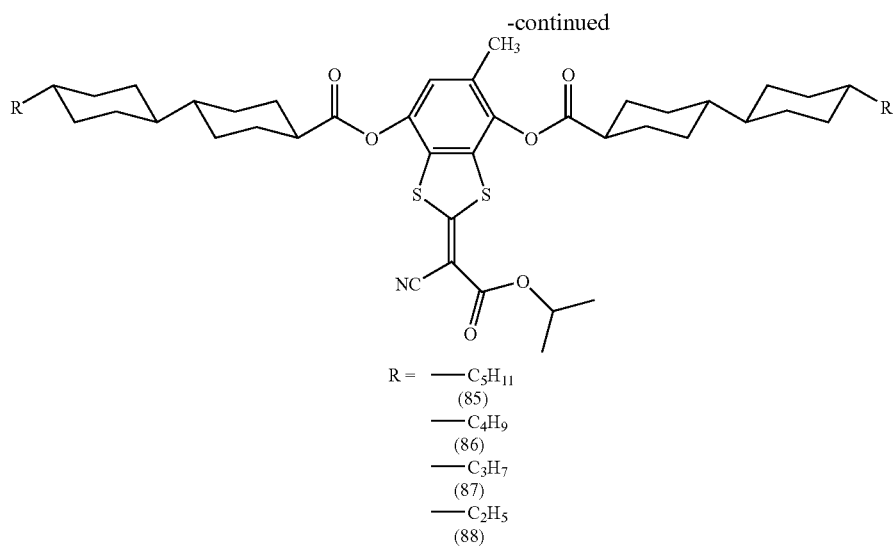
R = —C₅H₁₁ (85)
—C₄H₉ (86)
—C₃H₇ (87)
—C₂H₅ (88)
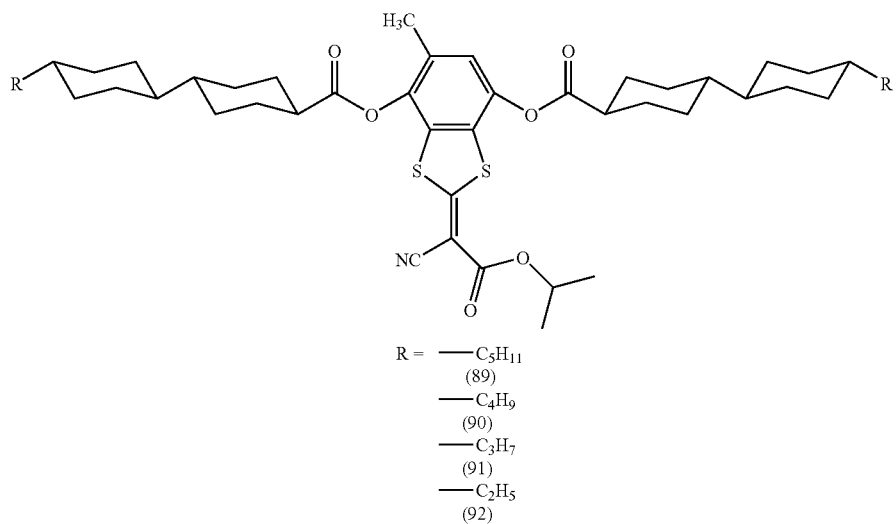
R = —C₅H₁₁ (89)
—C₄H₉ (90)
—C₃H₇ (91)
—C₂H₅ (92)
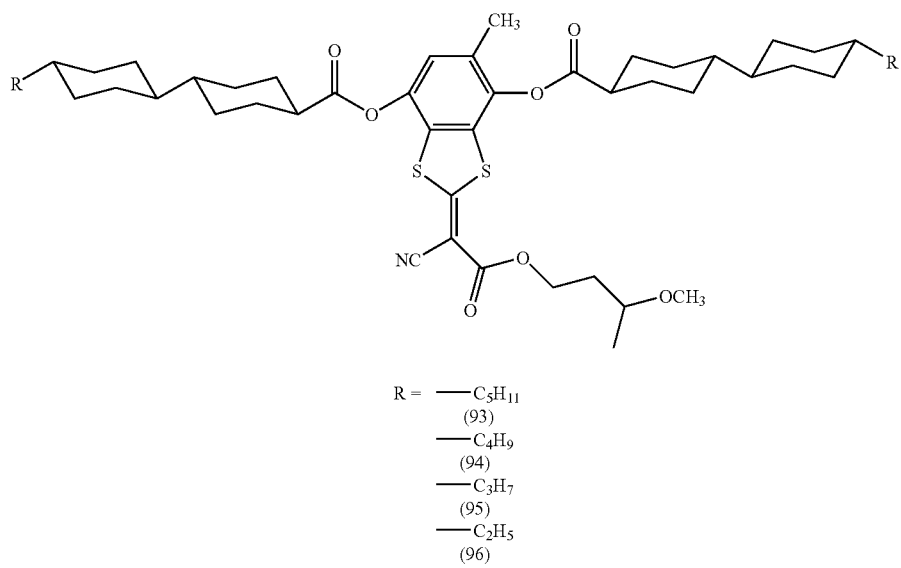
R = —C₅H₁₁ (93)
—C₄H₉ (94)
—C₃H₇ (95)
—C₂H₅ (96)

-continued
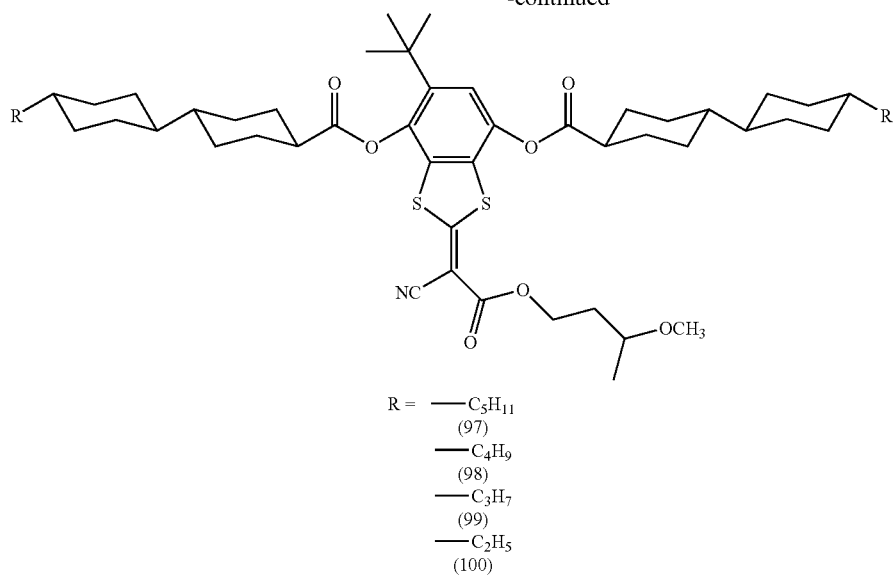
R = —C$_5$H$_{11}$
(97)
—C$_4$H$_9$
(98)
—C$_3$H$_7$
(99)
—C$_2$H$_5$
(100)
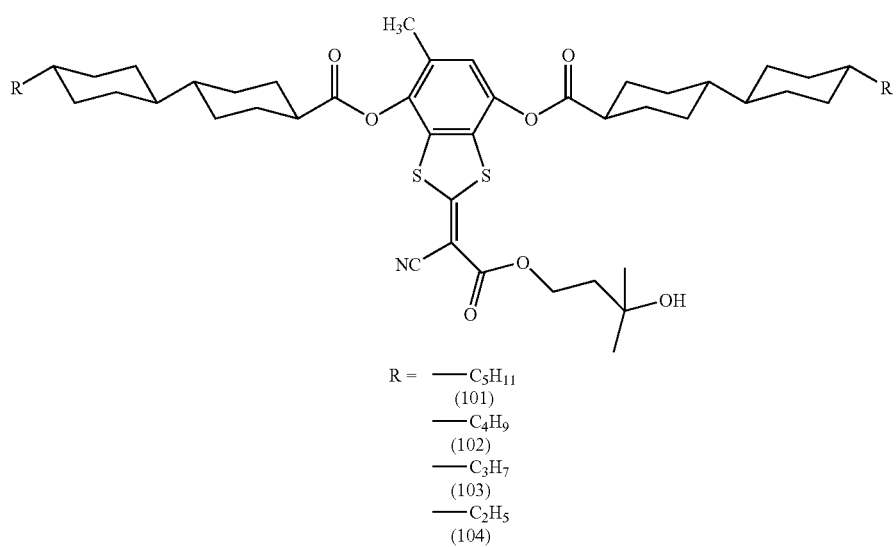
R = —C$_5$H$_{11}$
(101)
—C$_4$H$_9$
(102)
—C$_3$H$_7$
(103)
—C$_2$H$_5$
(104)
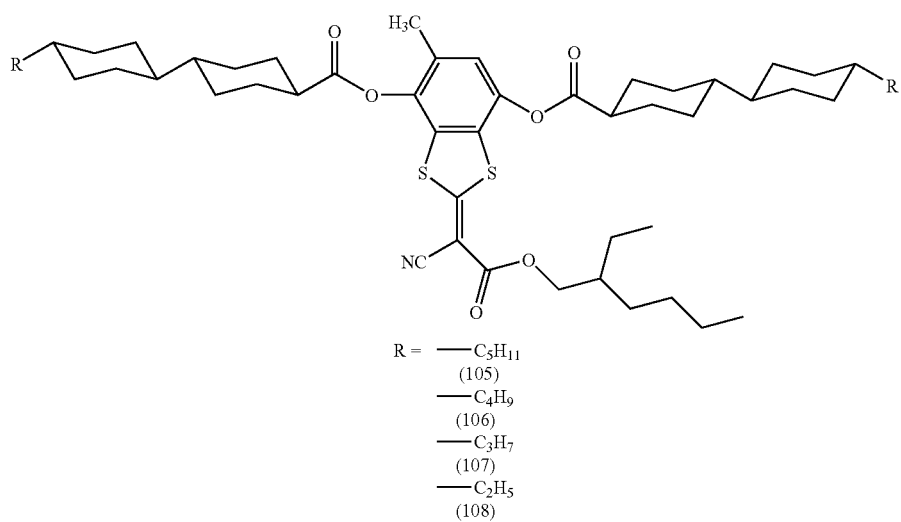
R = —C$_5$H$_{11}$
(105)
—C$_4$H$_9$
(106)
—C$_3$H$_7$
(107)
—C$_2$H$_5$
(108)

-continued
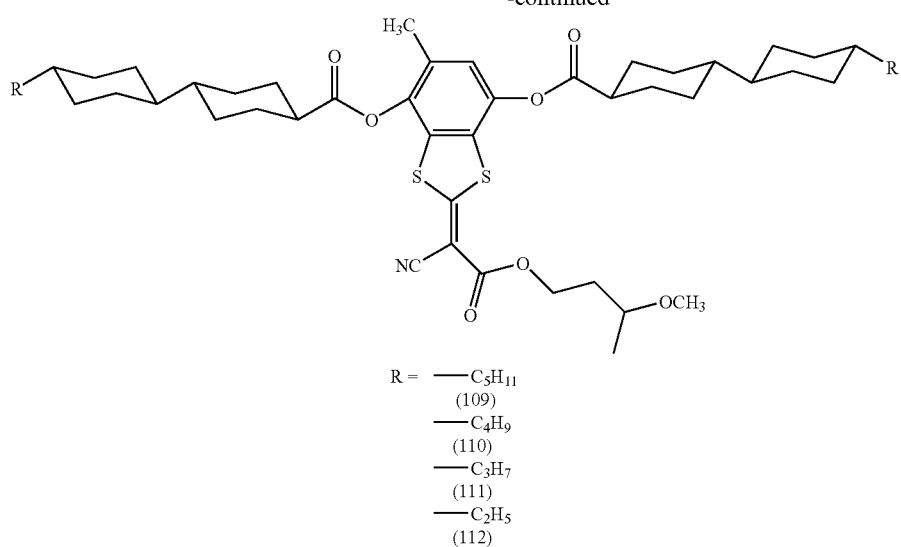
R = —C$_5$H$_{11}$
(109)
—C$_4$H$_9$
(110)
—C$_3$H$_7$
(111)
—C$_2$H$_5$
(112)
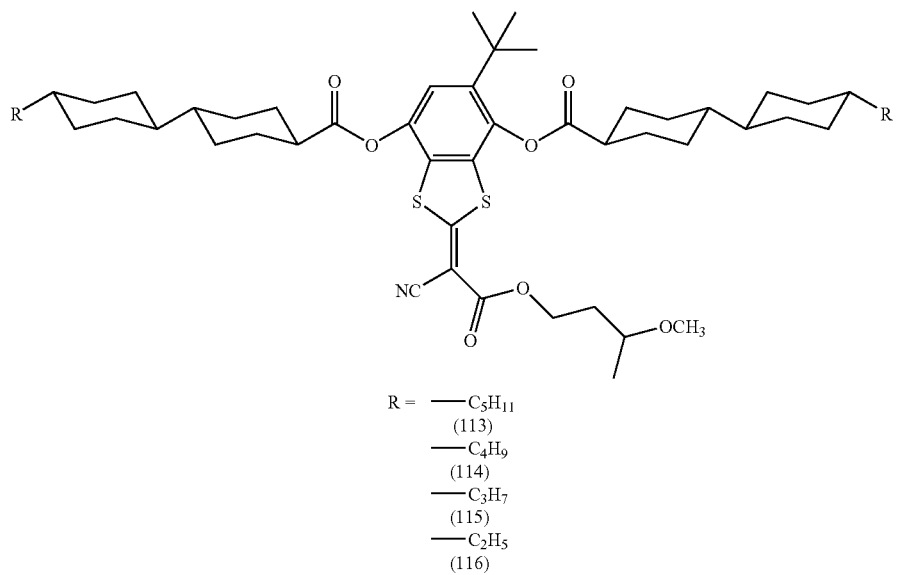
R = —C$_5$H$_{11}$
(113)
—C$_4$H$_9$
(114)
—C$_3$H$_7$
(115)
—C$_2$H$_5$
(116)
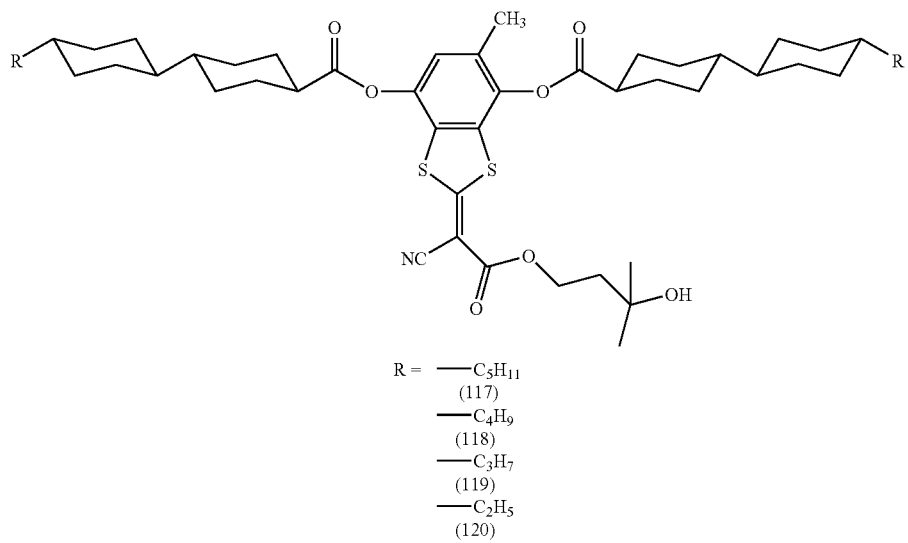
R = —C$_5$H$_{11}$
(117)
—C$_4$H$_9$
(118)
—C$_3$H$_7$
(119)
—C$_2$H$_5$
(120)

-continued
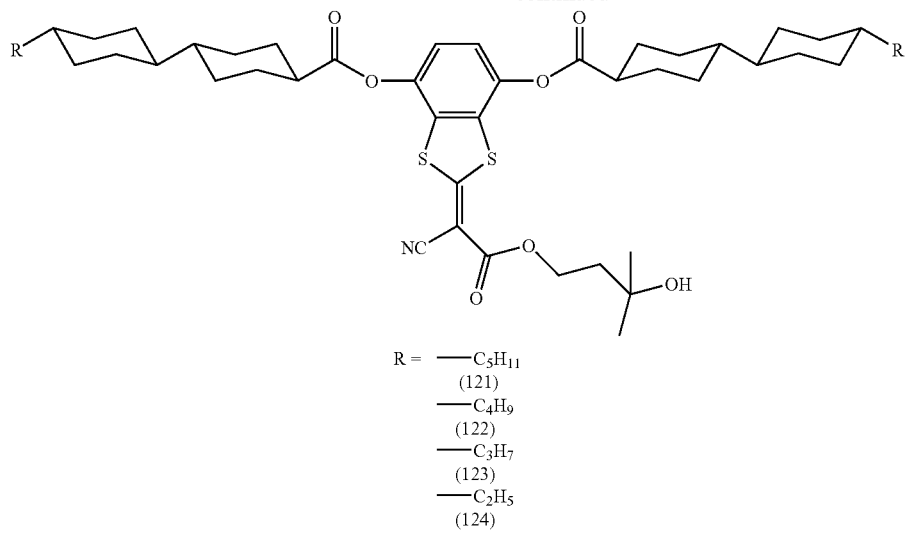
R = —C₅H₁₁ (121)
—C₄H₉ (122)
—C₃H₇ (123)
—C₂H₅ (124)
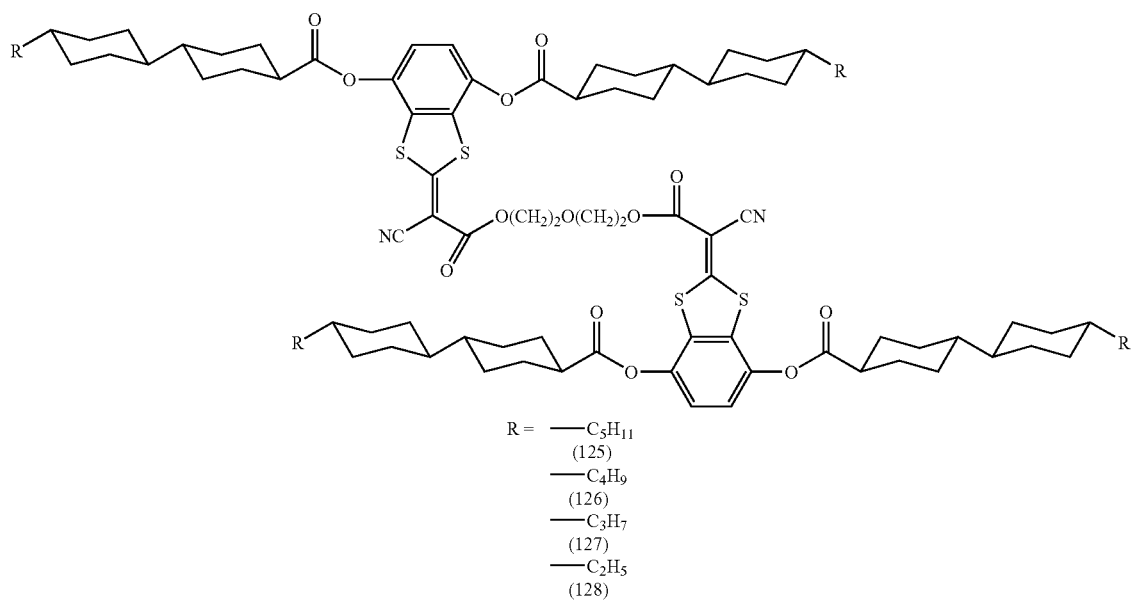
R = —C₅H₁₁ (125)
—C₄H₉ (126)
—C₃H₇ (127)
—C₂H₅ (128)
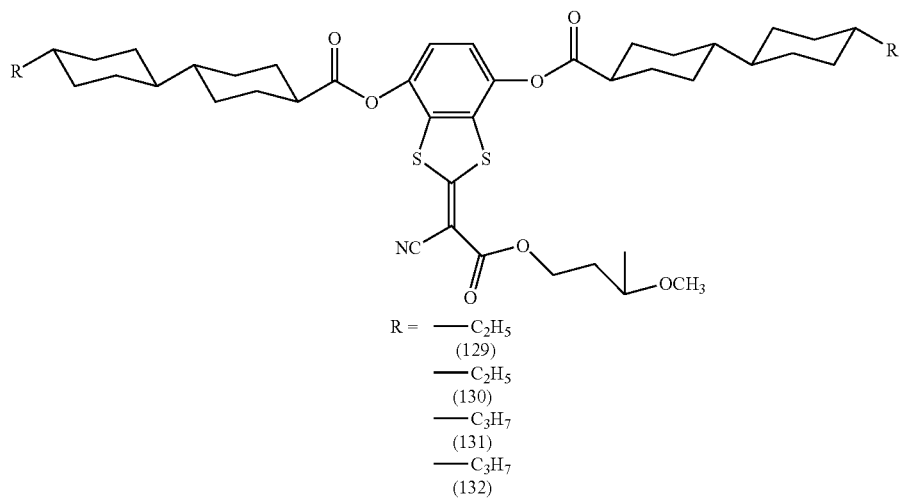
R = —C₂H₅ (129)
—C₂H₅ (130)
—C₃H₇ (131)
—C₃H₇ (132)

-continued
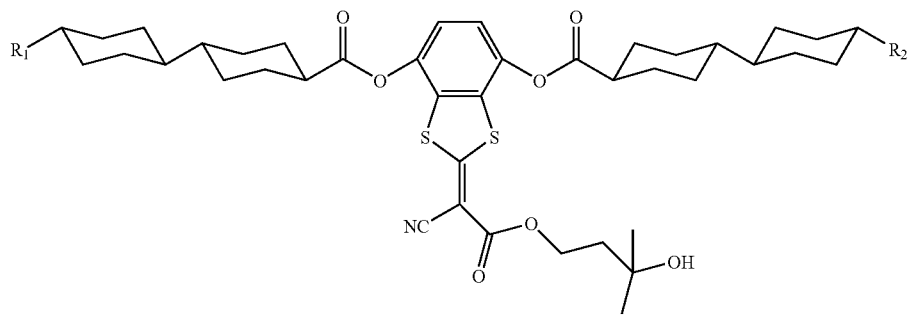
R₁ = —C₂H₅   R₂ = —C₄H₉
       (133)
      —C₂H₅        —C₃H₇
       (134)
      —C₃H₇        —C₄H₉
       (135)
      —C₃H₇        —C₅H₁₁
       (136)
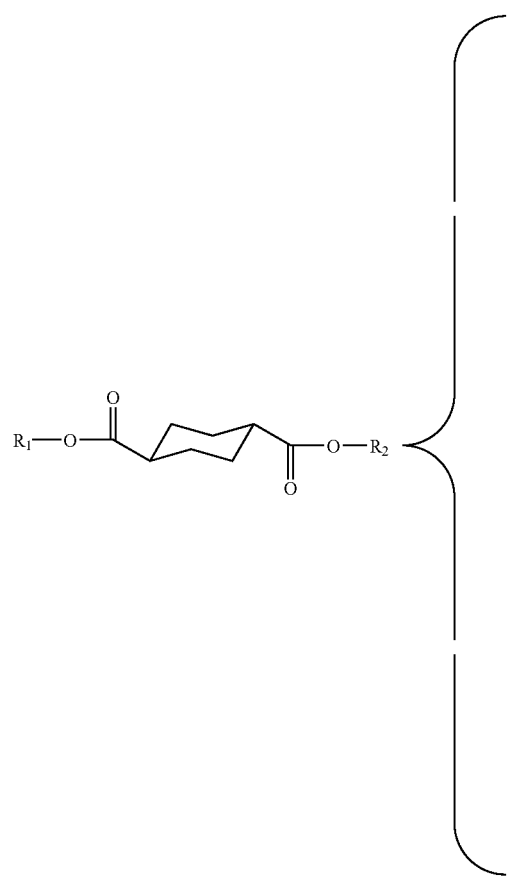
(137)
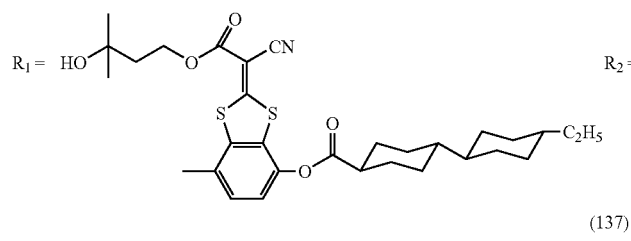

-continued
79
R₁ = 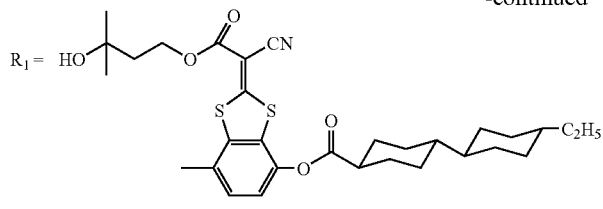
(138)
R₁ = 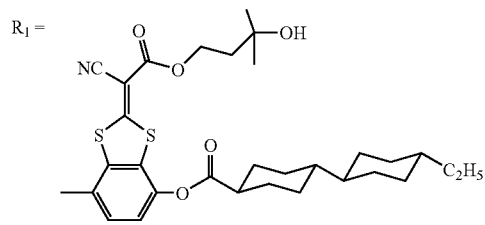
(139)
80
R₂ = 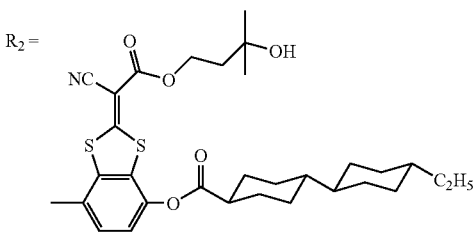
R₂ = 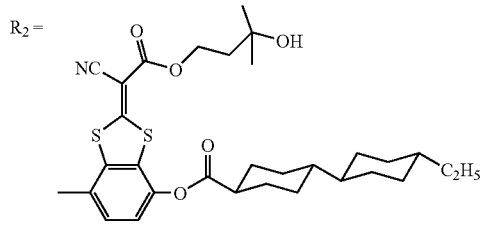
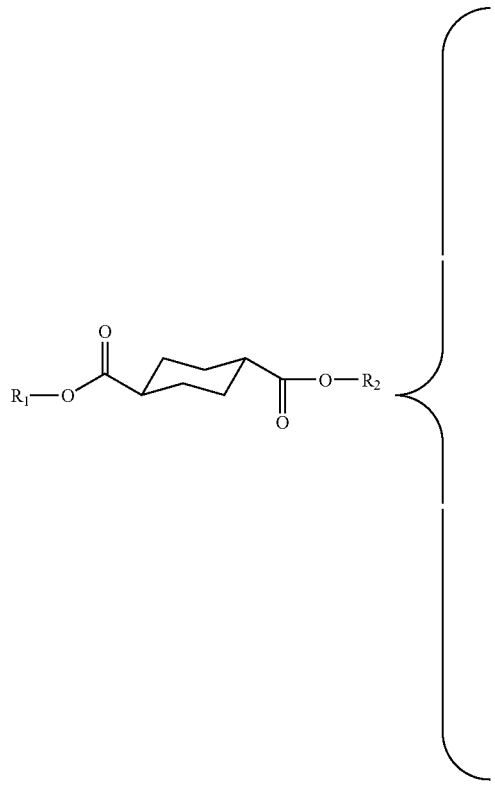
R₁ = 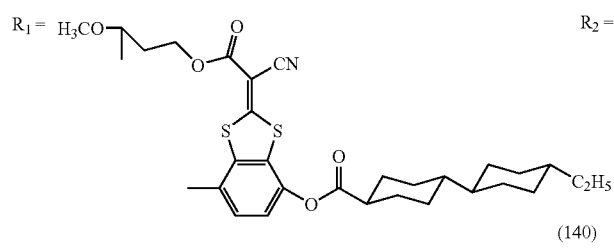
(140)
R₂ =

-continued
81
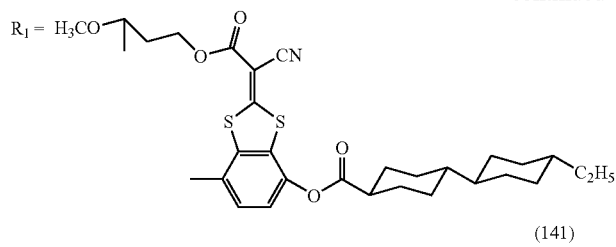
(141)
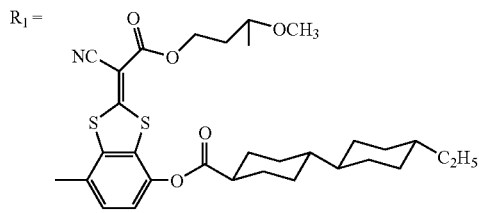
(142)
82
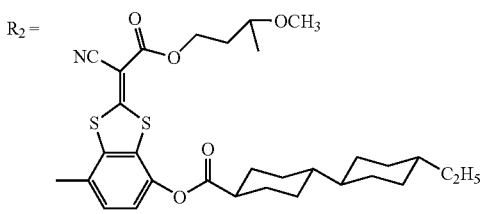
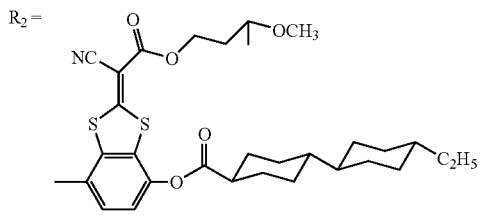
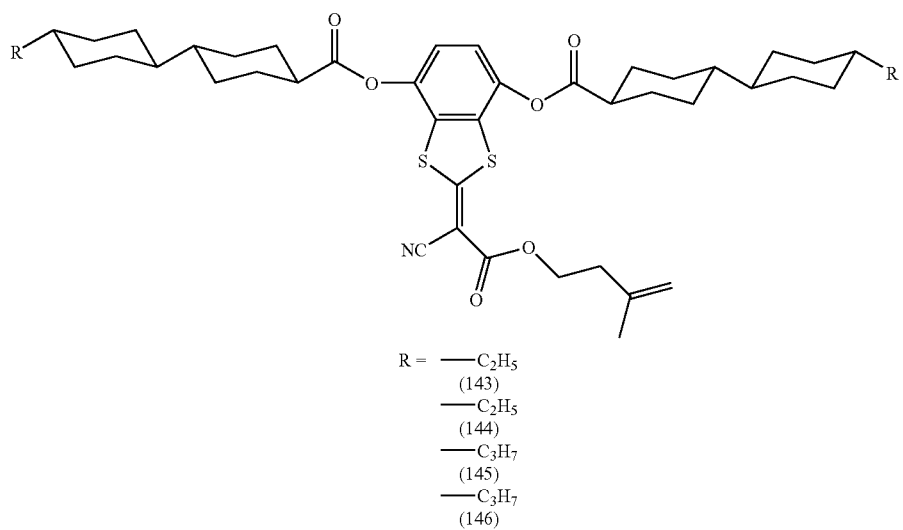
R = —C$_2$H$_5$
(143)
—C$_2$H$_5$
(144)
—C$_3$H$_7$
(145)
—C$_3$H$_7$
(146)
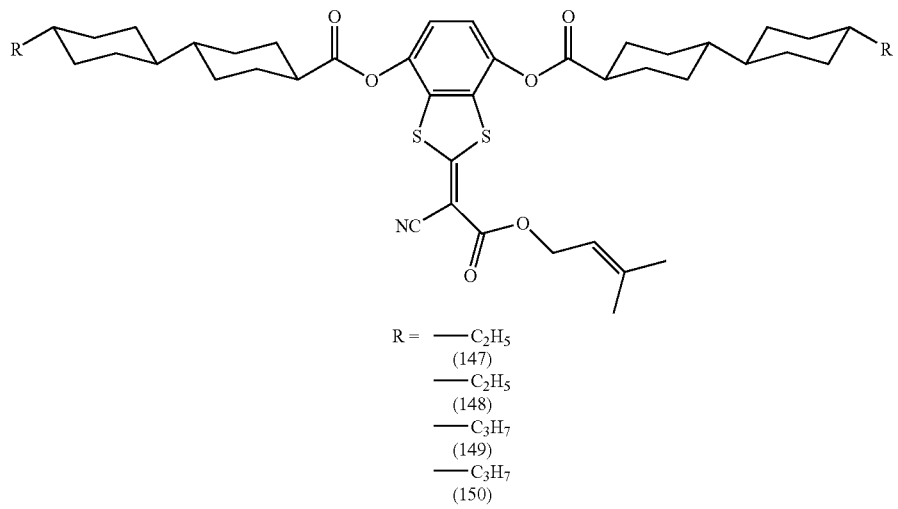
R = —C$_2$H$_5$
(147)
—C$_2$H$_5$
(148)
—C$_3$H$_7$
(149)
—C$_3$H$_7$
(150)

83
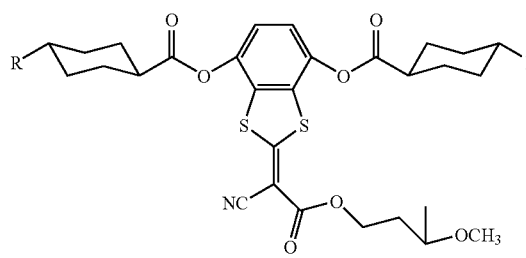
R = —H (151)
—C$_4$H$_9$ (152)
—C$_5$H$_{11}$ (153)
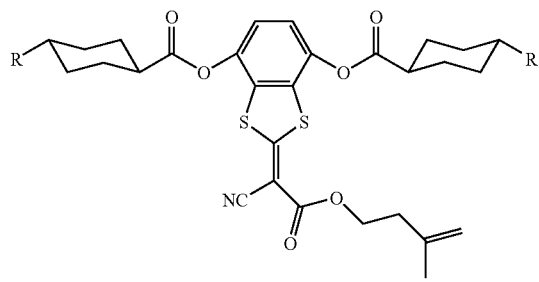
R = —H (157)
—C$_4$H$_9$ (158)
—C$_5$H$_{11}$ (159)
84
-continued
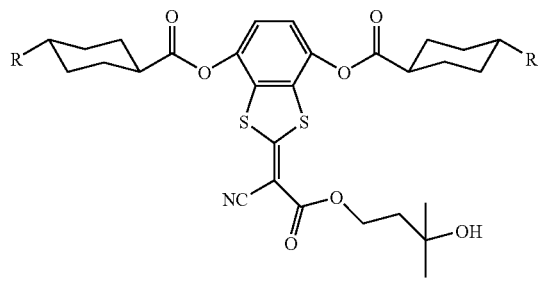
R = —H (154)
—C$_4$H$_9$ (155)
—C$_5$H$_{11}$ (156)
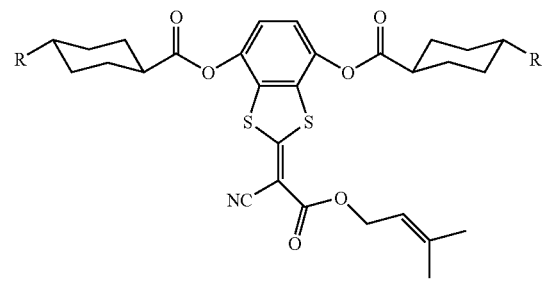
R = —H (160)
—C$_4$H$_9$ (161)
—C$_5$H$_{11}$ (162)
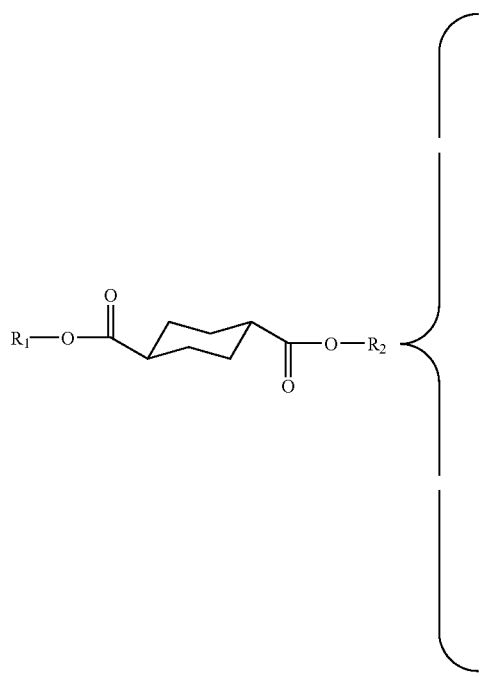

R₁ = 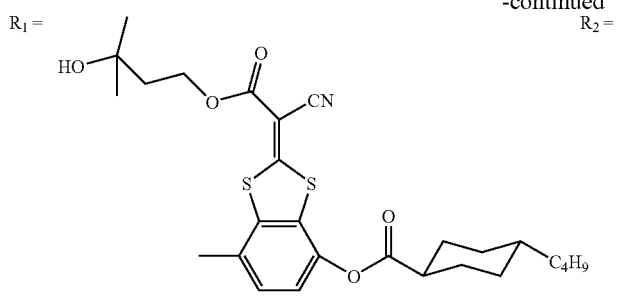
R₂ = 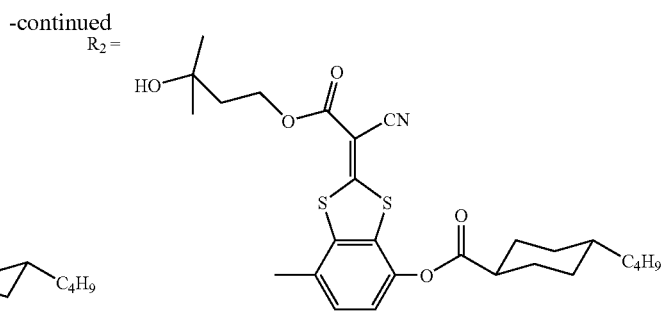

(163)

R₁ = 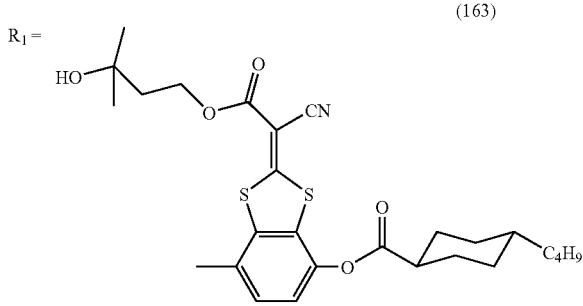
R₂ = 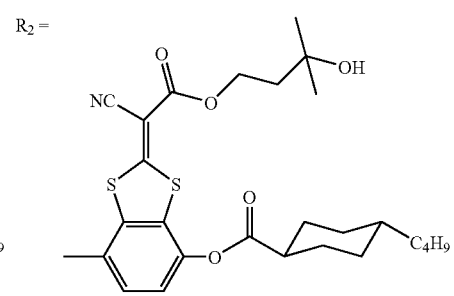

(164)

R₁ = 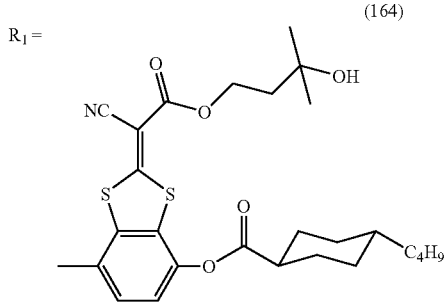
R₂ = 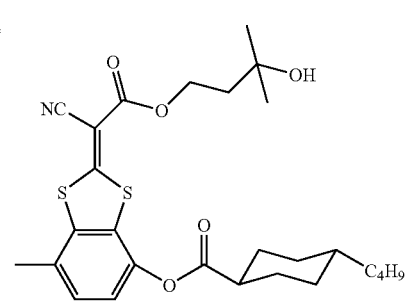

(165)

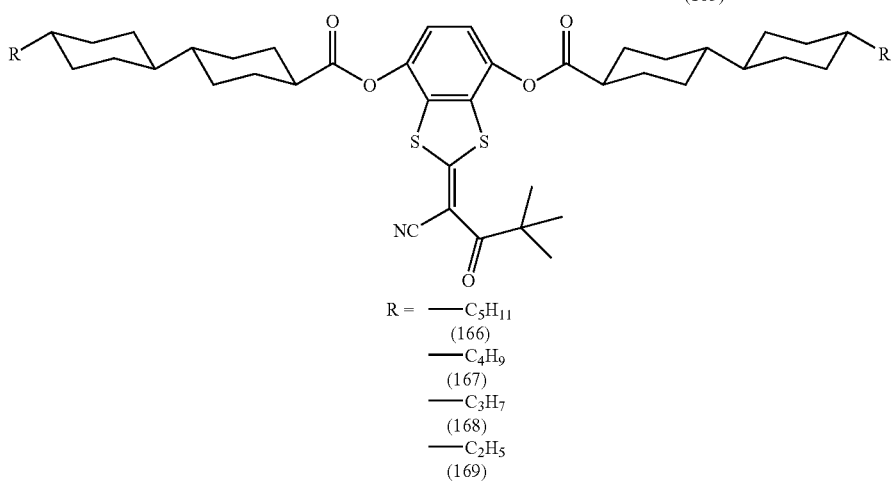

R = —C₅H₁₁ (166)
—C₄H₉ (167)
—C₃H₇ (168)
—C₂H₅ (169)

In the invention, the compound represented by the formula (III) or (VI) is added in an amount of preferably 0.1 to 20% by mass based on the cellulose acylate, more preferably 1 to 15% by mass, more preferably 2 to 12% by mass, and most preferably 3 to 10% by mass.

The compound represented by the formula (III) or (IV) can be synthesized with reference to known methods. For example, the exemplified compound (I) can be synthesized according to the following scheme.

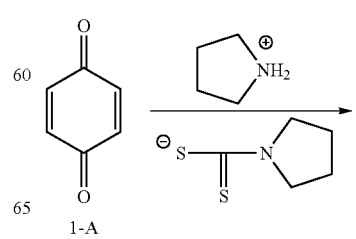

1-A

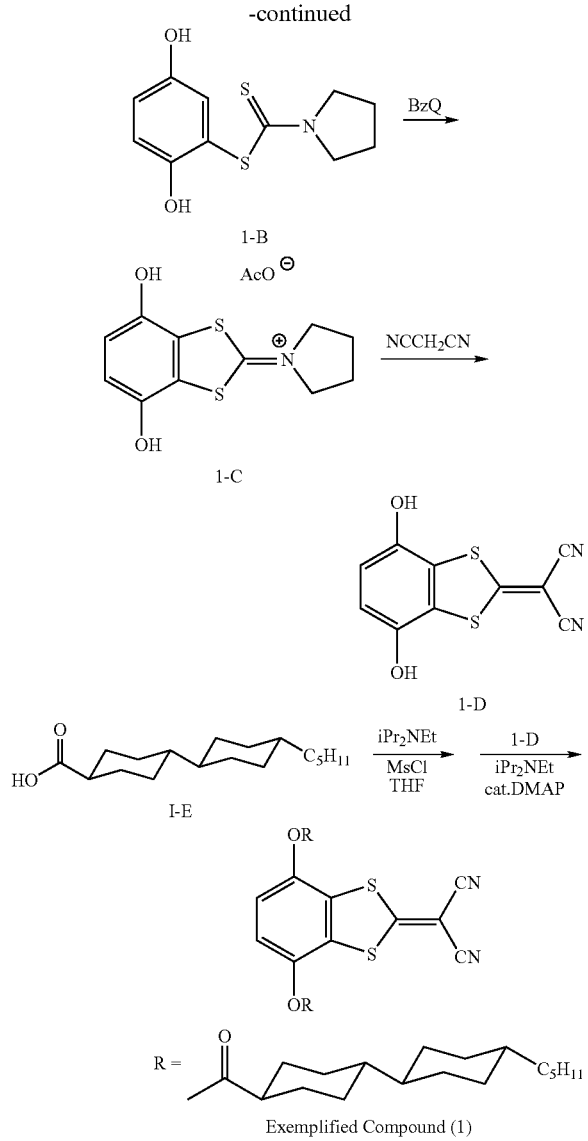

Exemplified Compound (1)

In the above scheme, the synthesis from the compound (1-A) to the compound (1-D) can be conducted by referring to the method described in *Journal of Chemical Crystallography*, (1997); 27(9); p. 515-526.

As shown in the above scheme, furthermore, methane sulfonic acid chloride is added to a tetrahydrofuran solution of compound (1-E), and N,N-diisopropylethylamine is further dropped thereinto. After stirring, N,N-diisopropylethylamine is added and a tetrahydrofuran solution of the compound (1-D) is dropped. Next, a tetrahydrofuran solution of N,N-dimethylaminopyridine (DMAP) is dropped. Thus, the exemplified compound (I) can be obtained.

The compound represented by the formula (III) or (IV) plays the role as a retardation-controlling agent (especially, a retardation-raising and wavelength dispersion-regulating agent) of an optical film. In particular, it acts favorably as a retardation-controlling agent for obtaining a film that is excellent in Re-developing property and wavelength dispersion by stretching.

It is preferable that the cellulose acrylate film satisfying the relationship defined by the formulae (4) and (5), which is favorably employed in the invention, contains, in addition to the compounds represented by the above formulae (III) and (IV), a rod-shaped Re developing agent as will be described hereinafter.

(Rod-Shaped Re Developing Agent)

In the invention "a rod-shaped compound" means a compound having a linear molecular structure. The terms "linear molecular structure" as referred to herein mean that the molecular structure of the rod-shaped compound is linear in the most thermodynamically stable structure. The most thermodynamically stable structure can be determined by the crystal structure analysis or molecular orbital calculation. Namely, it is possible to determine the molecular structure such that the heat of formation of the compound is the smallest by, for example, performing the molecular orbital calculation with the use of a molecular orbital calculation software (for example, WinMOPAC2000, manufactured by Fujitsu Inc.). The molecular structure being linear means that in the most thermodynamically stable structure, an angle constituted by the principal chain in the molecular structure is 140 degrees or more.

As the rod-shaped compound, a compound represented by the following formula (V) is particularly preferable.

$$Ar^1-L^2-X-L^3-Ar^2 \qquad \text{Formula (V)}$$

In the above formula (V), $Ar^1$ and $Ar^2$ each independently represents an aromatic group.

An aromatic group as mentioned herein includes an aryl group (an aromatic hydrocarbon group), a substituted aryl group, an aromatic heterocyclic group and a substituted aromatic heterocyclic group.

The aryl group and the substituted aryl group are preferred to the aromatic heterocyclic group and the substituted aromatic heterocyclic group. The heterocycle of the aromatic heterocyclic group is generally unsaturated. The aromatic heterocycle is preferably a 5-membered ring, a 6-membered ring or a 7-membered ring, and more preferably a 5-membered ring or a 6-membered ring. The aromatic heterocycle generally has the largest number of double bonds. As the hetero atom, a nitrogen atom, an oxygen atom or a sulfur atom is preferable, and a nitrogen atom or, a sulfur atom is more preferable.

Preferable examples of the aromatic ring of the aromatic group include a benzene ring, a furan ring, a thiophene ring, a pyrrole ring, an oxazole ring, a thiazole ring, an imidazole ring, a triazole ring, a pyridine ring, a pyrimidine ring and a pyrazine ring, and a benzene ring is particularly preferable.

Examples of the substituent of the substituted aryl group and the substituted aromatic heterocyclic group include a halogen atom (F, Cl, Br, I); a hydroxyl group; a carboxyl group; a cyano group; an amino group; an alkylamino group (for example, a methylamino group, an ethylamino group, a butylamino group, a dimethylamino group); a nitro group; a sulfo group; a carbamoyl group; an alkylcarbamoyl group (for example, an N-methylcarbamoyl group, an N-ethylcarbamoyl group, an N,N-dimethylcarbamoyl group); a sulfamoyl group; an alkylsulfamoyl group (for example, an N-methylsulfamoyl group, an N-ethylsulfamoyl group, an N,N-dimethylsulfamoyl group); a ureido group; an alkylureido group (for, example, an N-methylureido group, an N,N-dimethylureido group, an N,N,N'-trimethylureido group); an alkyl group (for example, a methyl group, an ethyl group, a propyl group, a butyl group, a pentyl group, a heptyl group, an octyl group, an isopropyl group, an s-butyl group, a t-amyl group, a cyclohexyl group, a cyclopentyl group); an alkenyl group (for example, a vinyl group, an allyl group, a hexenyl group); an alkynyl group (for example, an ethynyl group, a butynyl group); an acyl group (for example, a formyl group, an acetyl group, a butyryl group, a hexanoyl group, a lauryl group); an acyloxy group (for example, an acetoxy group, a butyryloxy group, a hexanoyloxy group, a lauryloxy group); an alkoxy group (for example, a methoxy group, an ethoxy group, a propoxy group, a butoxy group, a pentyloxy group, a heptyloxy group, an octyloxy group); an aryloxy group (for example, a phenoxy group); an alkoxycarbonyl group (for example, a methoxycarbonyl group, an ethoxycarbonyl group, a propoxycarbonyl group, a butoxycarbonyl group, a pentyloxycarbonyl group, a heptyloxycarbonyl group); an aryloxycarbonyl group (for example, a phenoxycarbonyl group); an alkoxycarbonylamino group (for example, a butoxycarbonylamino group, a hexyloxycarbonylamino group); an alkylthio group (for example, a methylthio group, an ethylthio group, a propylthio group, a butylthio group, a pentylthio group, a heptylthio group, an octylthio group); an arylthio group (for example, a phenylthio group); an alkylsulfonyl group (for example, a methylsulfonyl group, an ethylsulfonyl group, a propylsulfonyl group, a butylsulfonyl group, a pentylsulfonyl group, a heptylsulfonyl group, an octylsulfonyl group); an amide group (for example, an acetamide group, a butylamide group, a hexylamide group, a laurylamide group); and a non-aromatic heterocyclic group (for example, a morpholino group, a pyrazinyl group).

Preferable examples of the substituents of the substituted aryl group and the substituted aromatic heterocyclic group include a halogen atom, a cyano group, a carboxyl group, a hydroxyl group, an amino group, an alkyl-substituted amino group, an acyl group, an acyloxy group, an amide group, an alkoxycarbonyl group, an alkoxy group, an alkylthio group and an alkyl group.

The alkyl moiety and the alkyl group of the alkylamino group, the alkoxycarbonyl group, the alkoxy group and the alkylthio group may further have a substituent. Examples of the substituent of the alkyl moiety and the alkyl group include a halogen atom, a hydroxyl group, a carboxyl group, a cyano group, an amino group, an alkylamino group, a nitro group, a sulfo group, a carbamoyl group, an alkylcarbamoyl group, a sulfamoyl group, an alkylsulfamoyl group, a ureido group, an alkylureido group, an alkenyl group, an alkynyl group, an acyl group, an acyloxy group, an acylamino group, an alkoxy group, an aryloxy group, an alkoxycarbonyl group, an aryloxycarbonyl group, an alkoxycarbonylamino group, an alkylthio group, an arylthio group, an alkylsulfonyl group, an amide group and a non-aromatic heterocyclic group. As the substituent of the alkyl moiety and the alkyl group, a halogen atom, a hydroxyl group, an amino group, an alkylamino group, an acyl group, an acyloxy group, an acylamino group, an alkoxycarbonyl group and an alkoxy group are preferable.

In the formula (V), $L^2$ and $L^3$ each independently represents a divalent linking group selected from —O—, —CO—, —CO—O— and a combination thereof.

In the formula (V), X represents 1,4-cyclohexylene, vinylene or ethynylene.

Next, specific examples of the compound represented by the formula (V) will be presented.

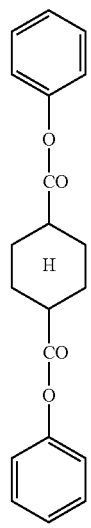

(1)

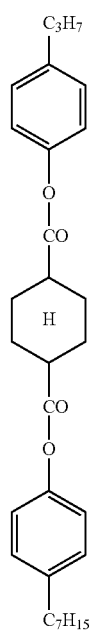

(2)

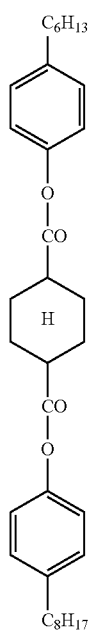
(3)
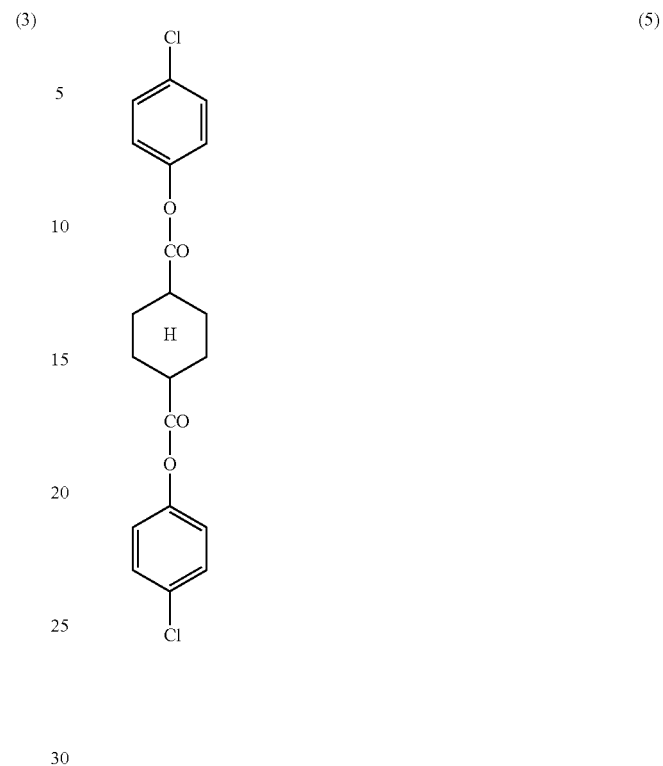
(5)
(4)
(6)
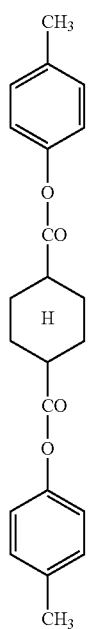
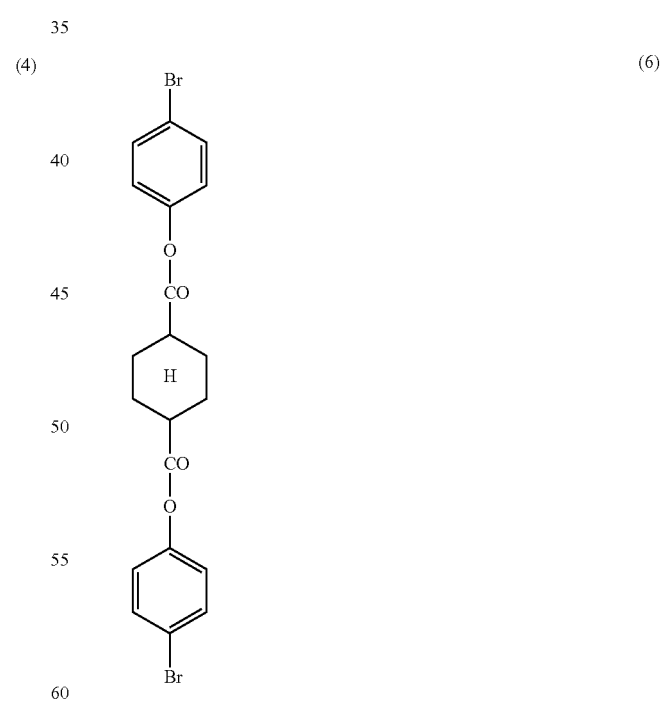

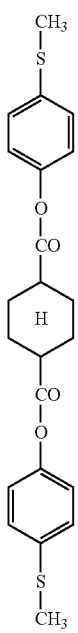 (7)
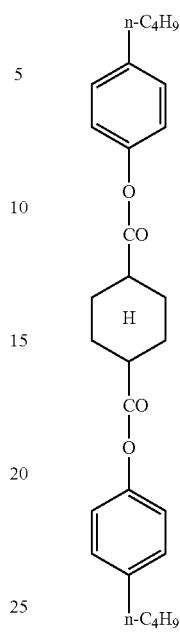 (9)
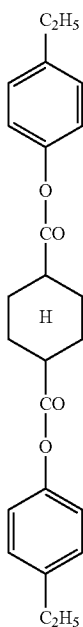 (8)
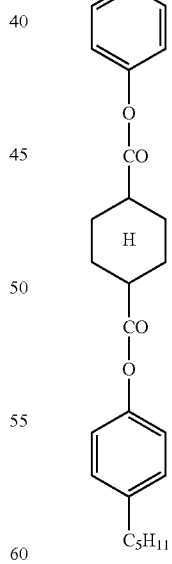 (10)

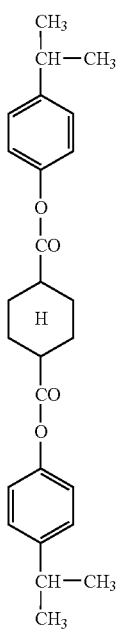 (11)
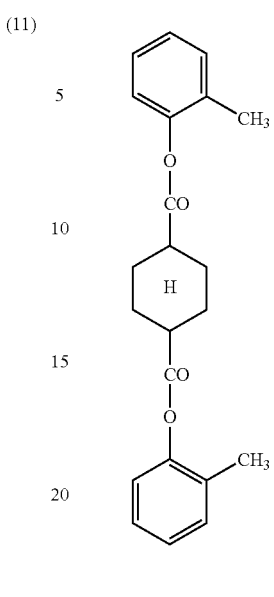 (13)
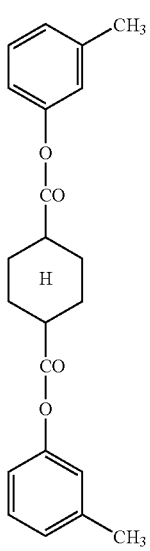 (12)
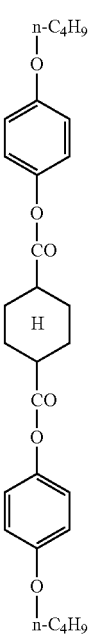 (14)

(15)
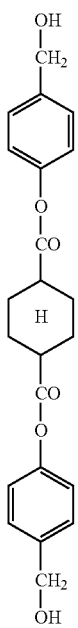
(17)
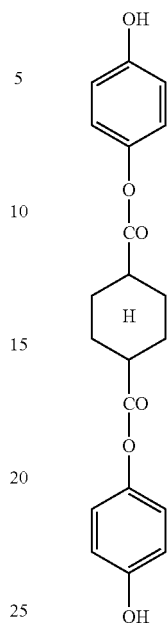
(16)
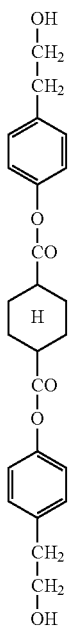
(18)
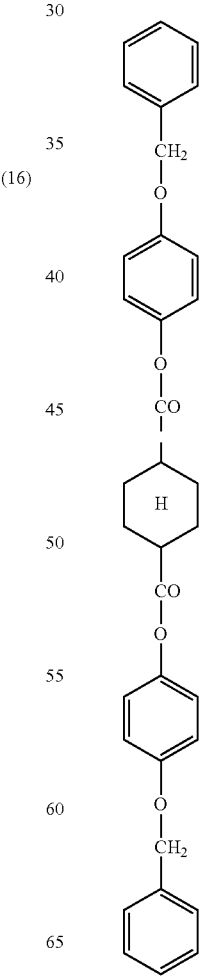

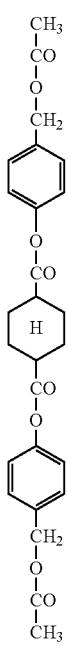
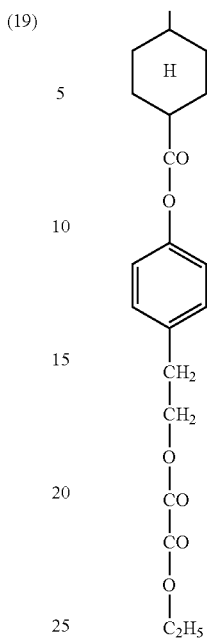

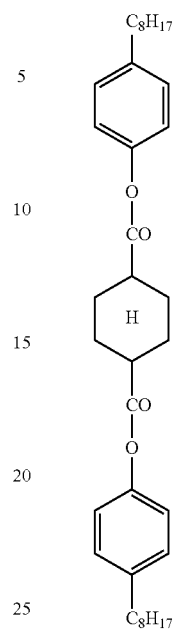
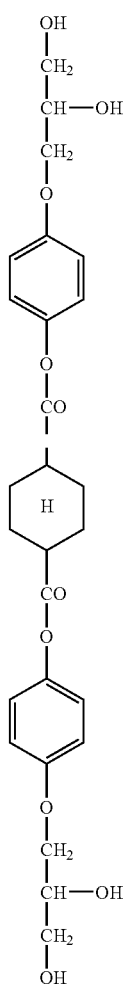
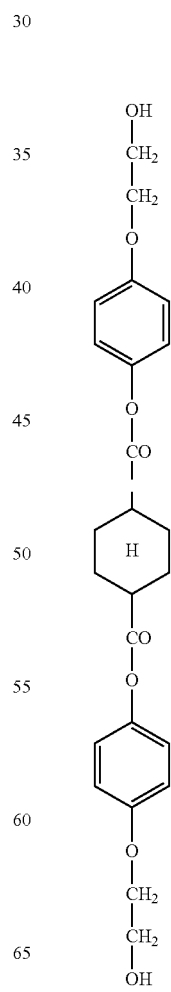

(25) 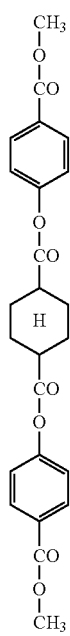 (27) 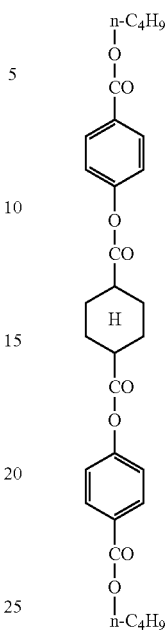
(26) 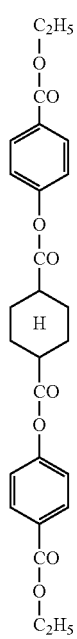 (28) 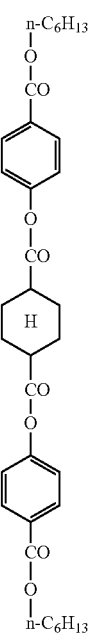

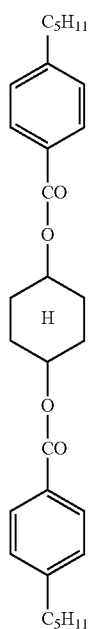 (29)
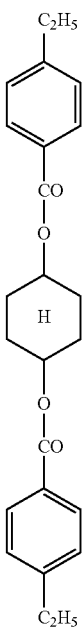 (31)
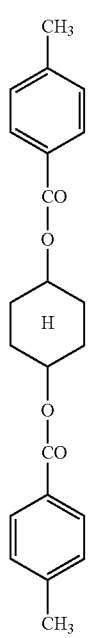 (30)
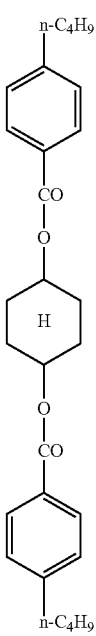 (32)

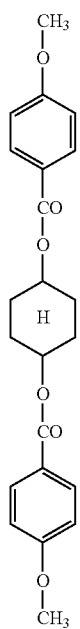
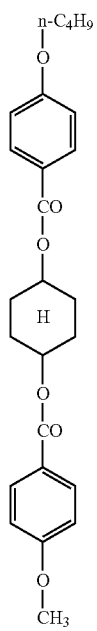
(33)
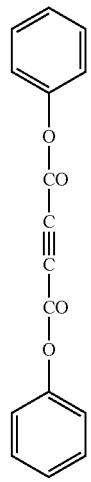
(34)
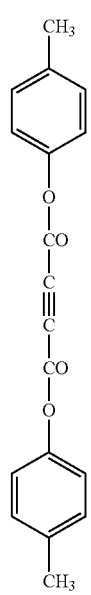
(35)
(36)
(37)
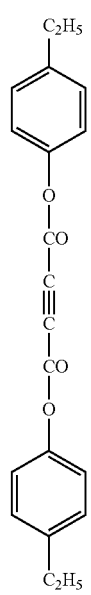

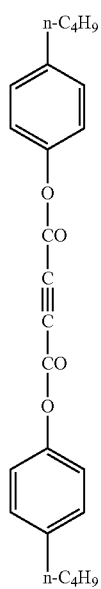
(38)
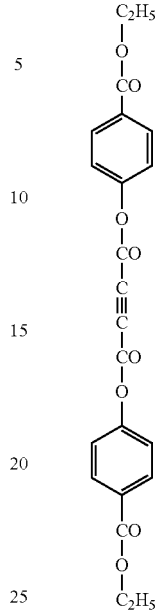
(40)
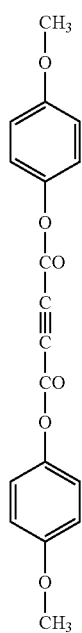
(39)
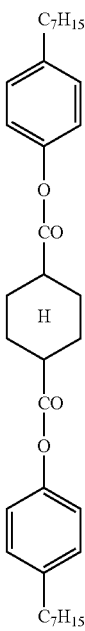
(41)

(42)
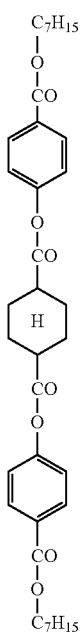

(44)
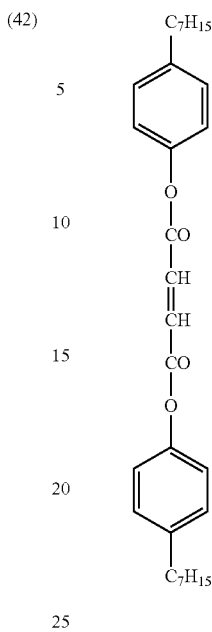

(43)
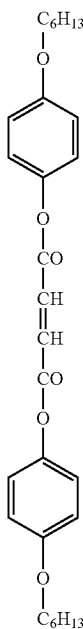

(45)
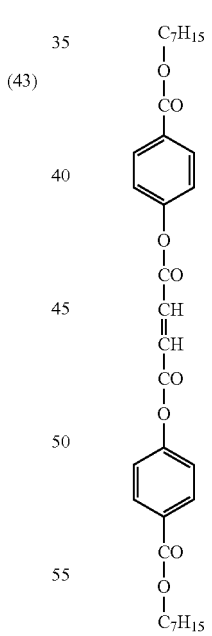

The compounds of the specific examples (1) to (34), (41) and (42) each has two asymmetric carbon atoms at the 1- and 4-positions of the cyclohexane ring. Because of having a symmetrical meso-type molecular structure, the compounds of the specific examples (1), (4) to (34), (41) and (42) have no optical isomer (optical activity) but occur merely as geometric isomers (trans- and cis-types). Next, the trans (1-trans) and cis (1-cis) isomers of the compound of the specific example (1) will be presented.

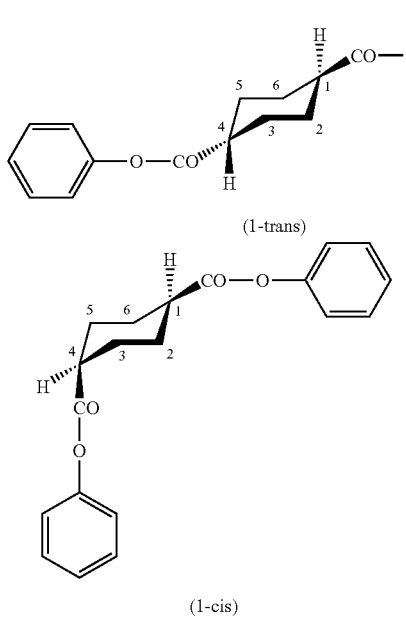

(1-trans)

(1-cis)

As described above, it is preferable that a rod-shaped compound has a linear molecular structure. Thus, a trans compound is preferred to a cis compound.

The compounds of the specific examples (2) and (3) occur as optical isomers in addition to geometric isomers (i.e., four isomers in total for each). Concerning the geometric isomers, a trans compound is preferred to a cis compound too. Concerning the optical isomers, there is no particular preference for one over the other Namely, either a D-compound, an L-compound or a racemate may be used.

In the compounds of the specific examples (43) to (45), the vinylene bond at the center occurs as trans- and cis-forms. For the same reason as the one described above, a trans-bond is preferred for a cis-bond.

It is also possible to use a combination of two kinds or more rod-shaped compounds each having the maximum absorption wavelength ($\lambda$max) in an ultraviolet ray absorption spectrum of a solution thereof of shorter than 250 nm.

The rod-shaped compound can be synthesized by referring to a method described in a document. Examples of the document include *Mol. Cryst. Liq. Cryst.*, Vol. 53, p. 229 (1979); ibid., Vol. 89., p. 93 (1982); ibid., Vol. 145, p. 111 (1987); ibid., Vol. 170, p. 43 (1989); *J Am. Chem. Soc.*, Vol. 113, p. 1349 (1991); ibid., Vol. 118, p. 5346 (1996); ibid., Vol. 92, p. 1582 (1970); *J. Org. Chem.*, Vol. 40, p. 420 (1975); and *Tetrahedron*, Vol. 48, No. 16, p. 3437 (1992).

The molecular weight of the retardation-developing agent in the invention is preferably from 200 to 1,000, and more preferably from 300 to 850. So long as the molecular weight falls within this range, both the solubility in a solvent and retention during film forming are satisfied. The boiling point of the compound in the invention is preferably 260° C. or higher. The boiling point can be measured with a commercially available measuring apparatus (for example, TG/DTA100 manufactured by Seiko Instruments).

The compound represented by the formula (V) may be used either singly or as a mixture of two or more types. It is also preferable in the invention to use the compounds represented by formulae (III) to (V) in combination. In the invention, the retardation-developing agent is added in an amount of 2 to 30% by mass based on 100 parts by mass of the cellulose acylate, preferably 3 to 25% by mass, and more preferably 5 to 20% by mass.

The retardation-developing agent in the invention may be added to the cellulose acylate solution (dope) after having been dissolved in an organic solvent such as an alcohol, methylene chloride or dioxolan, or it may be added directly to the dope composition

[Production of Stretched Cellulose Acylate Film]

The stretched cellulose acylate film of the invention can be film-formed in the same method as in the film-formation of the normal wavelength dispersion cellulose acylate film as described above.

[Stretching Treatment]

The stretching of the cellulose acylate film is carried out preferably in both width and length directions.

The method of stretching a film in the width direction is disclosed in, for example, JP-A-62-115035, JP-A-4-152125, JP-A-4-284211, JP-A-4-298310 and JP-A-11-48271 and so on.

A film is stretched at room temperature or under heating. It is preferable that the heating temperature is not hither than the glass transition temperature of the film. The film can be stretched by a treatment during drying, which is particularly effective in the case where a solvent remains therein. In the case of stretching in the length direction, for example, a film is stretched while setting the winding rate of the film to higher than the peeling rate of the film by controlling the rate of transfer rolls for the film. In the case of the width direction stretching, a film can be stretched by transferring the film while keeping the width of the film with tenters, and gradually broadening the width between the tenters. It is also possible to stretch a film with the use of a stretching machine (preferably a uniaxial stretching with a Long stretching machine) after drying a film.

The stretching ratio (stretched percentage based on the unstretched film) is preferably from 1% to 200%, and more preferably from 5% to 150%. In particular, it is preferable that the stretching ratio in the width direction is from 1% to 200%, and more preferably from 5% to 150%. The stretching speed is preferably from 1%/min to 100%/min, more preferably from 5%/min to 80%/min, and most preferably from 10%/min to 60%/min.

It is preferable that the stretched cellulose acylate film of the invention is produced by, after stretching to the maximum stretching ratio, conducting the step of holding at a lower stretching ratio than the maximum stretching ratio for a certain period of time (hereinafter referred to as the relaxation step). The stretching ratio in the relaxation step is preferably from 50% to 99% of the maximum stretching ratio, more preferably from 70% to 97%, and most preferably from 90% to 95%. The relaxation step is conducted preferably for 1 sec to 120 sec, and more preferably for 5 sec to 100 sec.

By controlling the stretching ratio and the period in the relaxation step within the above-described ranges respectively, it is possible to elevate the alignment degree of the retardation developing agent, thereby giving a cellulose acylate film which has a high retardation and shows a small retardation variation in the front and thickness direction.

[Saponification Treatment]

The polarizing plate protective film according to the invention comprises the polymer film according to the invention.

It is preferable that the cellulose acylate film of the invention is subjected to a saponification treatment in the same way as in the normal wavelength dispersion cellulose acylate film as described above and then used as a polarizing plate protective film.

It is preferable that the optically compensatory film, which satisfies the above-described formulae (4) and (5) and is preferably used in the liquid crystal display device of the invention, satisfies the relation of the following formulae (6) and (7).

$$0.5 < Re(446)/Re(548) < 1.0 \quad \text{Formula (6)}$$

$$1.0 < Re(628)/Re(548) < 2.0 \quad \text{Formula (7)}$$

In the formula (6), it is more preferable that Re(446)/Re(548) is 0.55 or more but not more than 0.95, and most preferably from 0.6 to 0.90.

In the formula (7), it is more preferable that Re(628)/Re(548) is preferably from 1.01 to 1.5, and most preferably from 1.02 to 1.3.

As the optically compensatory film that satisfies the formulae (4) to (7), use can be preferably made of a stretched film made of a polycarbonate resin as disclosed in WO 2003/232060, a stretched film made of a cycloolefin-based resin as disclosed in JP-A-2006-188671, a stretched film made of a polyvinyl acetal-based resin as disclosed in JP-A-2006-234878, a polyimido film and a stretched cellulose acylate film as disclosed in JP-A-2006-3715 and so on.

Because of being excellent in processability as a polarizing plate, a cellulose acylate film containing the retardation developing agent represented by the formula (II) can be used especially preferably as the optically compensatory film satisfying the relation of the formulae (4) to (7).

(VA Mode)

It is preferable that the liquid crystal cell of the liquid crystal display device of the invention is a VA mode liquid crystal cell. Next, a VA mode liquid crystal display device will be described by referring to FIG. 1.

In a VA mode, liquid crystals having negative dielectric anisotropy and roughly satisfying $\Delta n = 0.0813$ and $\Delta \epsilon = -4.6$ are injected between upper and lower substrates so as to form about 89° of director showing the alignment direction of liquid crystal molecules (i.e., a so-called tilt angle) by rubbing alignment. In FIG. 1, the thickness d of the liquid crystal layer 7 is set to 3.5 μm. Depending on the product $\Delta n d$ ((thickness d)×(refraction index anisotropy $\Delta n$)), the brightness at the time of white level varies. To attain the maximum brightness, therefore, the thickness of the liquid crystal layer is set to a range of 0.2 μM to 0.5 μm.

The upper polarizing plate 1 and the lower polarizing plate 12 of the liquid crystal cell are laminated in such a manner that the respective absorption axis 2 and absorption axis 13 cross with each other approximately perpendicularly. Inside the respective alignment films of the liquid crystal cell upper electrode substrate 5 and the liquid crystal cell lower electrode substrate 8, transparent electrodes (not shown) are formed. In an undriven state where a driving voltage is not applied to electrodes, however, liquid crystal molecules in the liquid crystal layer 7 are aligned approximately vertically to the substrate face. As a result, the polarization state of light passing through the liquid crystal panel is scarcely changed. In this liquid crystal display device, the ideal black level can be achieved at the undriven state. In a driven state, on the contrary, the liquid crystal molecules are inclined in parallel to the substrate face, and light passing through the liquid crystal panel undergoes a change in the polarization state due to these thus inclined liquid crystal molecules. In the liquid crystal display device, in other words, white level is achieved in the driven state. In FIG. 1, numerical symbols 6 and 9 represent the alignment controlling direction.

Since an electric field is applied between the upper and lower substrates, use is made herein of a liquid crystal material having a negative dielectric anisotropy that allows the liquid crystal molecules to respond in the direction perpendicular to the electric field. In the case where the electrodes are provided on one of substrates and an electric field is applied in the lateral direction parallel to the substrate, a material having a positive dielectric anisotropy is used as the liquid crystals.

In a VA mode liquid crystal display device, a chiral agent, which is used generally in TN mode liquid crystal display devices, is not so frequently used because it would degrade the dynamic response properties. However, it is added in some cases for reducing alignment failure.

The VA mode is characterized by showing a high-speed response and a high contrast. However, it suffers from a problem that the contrast is high when viewed from the front but lowered when viewed from an oblique direction. At the time of black level, liquid crystal molecules are aligned perpendicularly to the substrate face. When observed from the front, the liquid crystal molecules show almost no birefringence and thus the transmittance is low and a high contrast can be obtained. When observed from an oblique direction, however, the liquid crystal molecules show birefringence. Moreover, the crossing angle between the absorption axes of the upper and lower polarizing plates, which is orthogonal (i.e., 90°) when viewed from the front, exceeds 90° when viewed from an oblique direction. Due to these two reasons, there arises light leakage in an oblique direction and thus the contrast is lowered. In order to solve this problem, an optical compensatory sheet is provided.

In the white level where liquid crystal molecules are inclined, the birefringence of liquid crystal molecules varies between the incline direction and the inverse direction, when observed from an oblique direction, which results in the difference in the brightness and hue. To solve this problem, a structure called multidomain, in which a single pixel of a liquid crystal display device is divided into plural domains, is adopted.

[Multidomain]

In the VA system, for example, liquid crystal molecules are inclined in different multiple domains in a single pixel upon the application of the electric field, thereby averaging viewing angle properties. To divide the alignment in a single pixel, a slit or a peak is formed in the electrode to change the electric field direction or make bias in the electric field density. To obtain even viewing angles in all directions, the number of the divisions is increased. Namely, almost even viewing angles can be achieved by the division into 4, 8 or more domains. It is particularly preferable to divide into 8 domains, since the polarizing plate absorption axis can be set at an arbitrary angle in this case.

In boundary portions among divided alignment domains, liquid crystal molecules can not respond easily. Thus, black level is maintained in normally black display, which results in a problem of lowering in brightness. To solve the problem, the boundary portions can be reduced by adding a chiral agent to the liquid crystal material.

EXAMPLES

Next, the invention will be described in greater detail by referring to the following Examples. The materials employed, the amounts thereof percentages, treatment ways, treatment procedures and so on used in the following Examples may be arbitrarily changed without departing from the scope of the invention. That is to say, it is to be understood that the scope of the invention is not restricted to these specific examples. The polymer film according to the invention will be some-times simply called "film", "normal wavelength dispersion film", "cellulose acylate film" and so on.

Example 1

Production of Normal Wavelength Dispersion Film
101

<Preparation of Cellulose Acylate Solution>
The following composition was fed into a mixing tank and stirred to dissolve the individual components, thereby preparing a cellulose acylate solution A.
[Composition of Cellulose Acylate Solution A]

| | |
|---|---|
| Cellulose acetate (acetyl substitution degree: 2.93, average degree of polymerization: 310) | 100.0 parts by mass |
| Triphenyl phosphate | 4.3 parts by mass |
| Biphenyl diphenyl phosphate | 3.0 parts by mass |
| Methylene chloride (first solvent) | 402.0 parts by mass |
| Methanol (second solvent) | 60.0 parts by mass |

<Preparation of Matting Agent Solution>
The following composition was fed into a dispersing machine and stirred to dissolve the individual components, thereby preparing a matting agent solution
[Composition of Matting Agent Solution]

| | |
|---|---|
| Silica particles (average particulate size: 20 nm, AEROSIL R972 manufactured by AEROSIL) | 2.0 parts by mass |
| Methylene chloride (first solvent) | 75.0 parts by mass |
| Methanol (second solvent) | 12.7 parts by mass |
| Cellulose acylate solution A | 10.3 parts by mass |

<Preparation of Wavelength Dispersion Regulator Solution>
The following composition was fed into a mixing tank and stirred with heating to dissolve the individual components, thereby preparing a wavelength dispersion regulator solution.
[Composition of Wavelength Dispersion Regulator Solution]

| | |
|---|---|
| Wavelength dispersion regulator (16) | 5.7 parts by mass |
| Light-fastness improving agent (I-(2)) | 14.3 parts by mass |
| Methylene chloride (first solvent) | 58.4 parts by mass |
| Methanol (second solvent) | 8.7 parts by mass |
| Cellulose acylate solution A | 12.8 parts by mass |

93.9 parts by mass of the cellulose acylate solution A, 1.3 parts by mass of the matting agent solution and 4.8 parts by mass of the wavelength dispersion regulator solution were filtered and mixed. Next, the mixture was cast to give a width of 1600 mm by using a band casting machine. When the residual solvent content attained 50% by mass, the film was peeled off from the band. Then, the film was held with tenter clips and laterally stretched at the stretching ratio of 4% at 100° C., and dried until the residual solvent content became 5% by mass. Subsequently, the film was held at 100° C. for 30 seconds while keeping the width after the stretching. Then, the film was released from the tenter clips. After cutting off each 5% of the film from both ends in the width direction, the film was passed through a drying zone at 135° C. over 20 minutes in a free state (not held) in the width direction and then wound into a roll. The obtained cellulose acylate film (normal wavelength dispersion film 101) had a residual solvent content of 0.1% by mass and a thickness of 55 μm.

Example 2

Production of Normal Wavelength Dispersion Films
102 to 105

Normal wavelength dispersion films 102 to 105 were produced in the same way as described above but changing the type of cellulose acylate, the type and addition amount of the additives, and the film thickness as listed in Table 1.

Example 3

Production of Normal Wavelength Dispersion Film
106

<Preparation of Cellulose Acylate Solution>
The following composition was fed into a mixing tank and stirred to dissolve the individual components, thereby preparing a cellulose acylate solution B.
[Composition of Cellulose Acylate Solution B]

| | |
|---|---|
| Cellulose acetate propionate(acetyl substitution degree: 2.00, propionyl substitution degree 0.50, average degree of polymerization: 330) | 100.0 parts by mass |
| Triphenyl phosphate | 4.3 parts by mass |
| Biphenyl diphenyl phosphate | 3.0 parts by mass |
| Methylene chloride (first solvent) | 370.0 parts by mass |
| Ethanol (second solvent) | 92.0 parts by mass |

<Preparation of Matting Agent Solution>
The following composition was fed into a dispersing machine and stirred to dissolve the individual components, thereby preparing a matting agent solution.
[Composition of Matting Agent Solution]

| | |
|---|---|
| Silica particles (average particulate size: 20 nm, AEROSIL R972 manufactured by AEROSIL) | 2.0 parts by mass |
| Methylene chloride (first solvent) | 70.2 parts by mass |
| Ethanol (second solvent) | 17.5 parts by mass |
| Cellulose acylate solution B | 10.3 parts by mass |

<Preparation of Wavelength Dispersion Regulator Solution>
The following composition was fed into a mixing tank and stirred with heating to dissolve the individual components, thereby preparing a wavelength dispersion regulator solution.
[Composition of Wavelength Dispersion Regulator Solution]

| | |
|---|---|
| Wavelength dispersion regulator (15) | 10.0 parts by mass |
| Methylene chloride (first solvent) | 61.8 parts by mass |
| Ethanol (second solvent) | 15.4 parts by mass |
| Cellulose acylate solution B | 12.8 parts by mass |

90.5 parts by mass of the cellulose acylate solution B, 1.3 parts by mass of the matting agent solution and 8.2 parts by mass of the wavelength dispersion regulator solution were filtered and mixed. Next, the mixture was cast to give a width of 2000 mm by using a band casting machine. When the residual solvent content attained 50% by mass, the film was peeled off from the band. Then, the film was held with tenter clips and laterally stretched at the stretching ratio of 5% at 100° C., and dried until the residual solvent content became 5% by mass. Subsequently, the film was held at 100° C. for 30 seconds while keeping the width after the stretching. Then, the film was released from the tenter clips. After cutting off each 5% of the film from both ends in the width direction, the film was passed through a drying zone at 125° C. over 20 minutes in a free state (not held) in the width direction and then wound into a roll. The obtained cellulose acylate film (normal wavelength dispersion film 106) had a residual solvent content of 0.1% by mass and a thickness of 55 μm.

Example 4

Production of Normal Wavelength Dispersion Films 107 to 115

Normal wavelength dispersion films 107 to 115 were produced in the same way as in Example 3 but changing the type of cellulose acylate, the type and addition amount of the additives, and the film thickness as listed in Table 1.

Comparative Example 1

Production of Normal Wavelength Dispersion Films 201 and 202

Normal wavelength dispersion films 201 to 202 were produced in the same way as in Example 1 but changing the type of cellulose acylate, the type and addition amount of the additives, and the film thickness as listed in Table 1.

Comparative Example 2

Production of Normal Wavelength Dispersion Films 203 and 207

Normal wavelength dispersion films 203 to 207 were produced in the same way as in Example 3 but changing the type of cellulose acylate, the type and addition amount of the additives, and the film thickness as listed in Table 1.

The structure of the light-fastness improving agent A used in Comparative Example is as follows.

Light-Fastness Improving Agent A

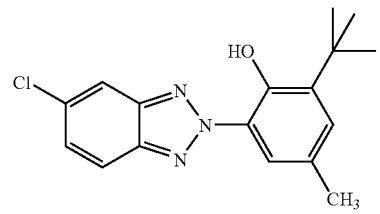

[Evaluation of Light-Fastness]

Measurement of Optical Characteristics Before Photo Irradiation

Using WR COBRA (manufactured by Oji Scientific Instruments), Re and Rth at 446 nm, 548 nm and 628 nm of the normal wavelength dispersion films 101 to 115 according to the invention and the normal wavelength dispersion films 201 to 207 of Comparative Examples were measured at 25° C. and 60% RH.

(Photo Irradiation)

The normal wavelength dispersion films 101 to 115 and 201 to 207 were cut into pieces (40 mm×60 mm) and photo irradiated, through a polarizing plate 5618 (manufactured by Sanritz Co.), by using a super xenon weathermeter SX75 (manufactured by Suga Test Instruments, conditions of 60° C. and 50% RH) for 200 hours.

Measurement of Optical Characteristics After Photo Irradiation

Using WR KOBRA (manufactured by Oji Scientific Instruments), Re and Rth at 446 nm, 548 nm and 628 nm of the normal wavelength dispersion films 101 to 115 according to the invention and the normal wavelength dispersion films

TABLE 1

| Film no. | Degree of substitution in cellulose acylate | | | Addition amount[a] of triphenyl phosphate | Addition amount[a] of biphenyl diphenyl phosphate | Wavelength dispersion regulator | | Light-fastness improving agent | | Film thickness | Remarks |
|---|---|---|---|---|---|---|---|---|---|---|---|
| | Acetyl group | Propionyl group | Total acyl substitution | | | Kind | Amount[a] | Kind | Amount[a] | | |
| 101 | 2.93 | 0.00 | 2.93 | 4.3 | 3.0 | (16) | 1.7 | I-2 | 4.1 | 55 | Invention |
| 102 | 2.93 | 0.00 | 2.93 | 6.6 | 4.7 | (16) | 3.0 | I-2 | 4.0 | 44 | Invention |
| 103 | 2.93 | 0.00 | 2.93 | 4.3 | 3.0 | (16) | 3.0 | I-2 | 4.0 | 48 | Invention |
| 104 | 2.81 | 0.00 | 2.81 | 3.0 | 1.5 | (14) | 4.0 | I-2 | 4.0 | 42 | Invention |
| 105 | 2.81 | 0.00 | 2.81 | 3.0 | 1.5 | (15) | 5.0 | IV-9 | 1.0 | 77 | Invention |
| 106 | 2.00 | 0.50 | 2.50 | 4.3 | 3.0 | (15) | 5.2 | No | 0.0 | 55 | Invention |
| 107 | 1.00 | 1.10 | 2.10 | 4.3 | 3.0 | (15) | 5.2 | No | 0.0 | 56 | Invention |
| 108 | 1.50 | 0.80 | 2.30 | 4.3 | 3.0 | (15) | 5.2 | No | 0.0 | 54 | Invention |
| 109 | 1.50 | 0.50 | 2.00 | 4.3 | 3.0 | (15) | 5.2 | No | 0.0 | 55 | Invention |
| 110 | 1.00 | 0.80 | 1.80 | 4.3 | 3.0 | (15) | 5.2 | No | 0.0 | 55 | Invention |
| 111 | 2.00 | 0.20 | 2.20 | 4.3 | 3.0 | (15) | 5.2 | No | 0.0 | 55 | Invention |
| 112 | 2.00 | 0.50 | 2.50 | 4.3 | 3.0 | (15) | 5.2 | I-2 | 4.0 | 55 | Invention |
| 113 | 2.00 | 0.50 | 2.50 | 4.3 | 3.0 | (8) | 6.4 | No | 0.0 | 55 | Invention |
| 114 | 2.00 | 0.50 | 2.50 | 4.3 | 3.0 | (10) | 7.0 | No | 0.0 | 55 | Invention |
| 115 | 2.00 | 0.50 | 2.50 | 4.3 | 3.0 | (11) | 8.0 | No | 0.0 | 55 | Invention |
| 201 | 2.93 | 0.00 | 2.93 | 4.3 | 3.0 | (16) | 3.0 | No | 0.0 | 47 | Comparison |
| 202 | 2.93 | 0.00 | 2.93 | 4.3 | 3.0 | (16) | 3.0 | A | 4.0 | 47 | Comparison |
| 203 | 2.00 | 0.50 | 2.50 | 4.3 | 3.0 | No | 0.0 | No | 0.0 | 55 | Comparison |
| 204 | 1.50 | 0.50 | 2.00 | 4.3 | 3.0 | (15) | 5.2 | I-2 | 4.0 | 65 | Comparison |
| 205 | 2.70 | 0.15 | 2.85 | 4.3 | 3.0 | (15) | 5.2 | No | 0.0 | 57 | Comparison |
| 206 | 1.50 | 1.30 | 2.80 | 4.3 | 3.0 | (15) | 5.2 | No | 0.0 | 53 | Comparison |
| 207 | 1.00 | 1.50 | 2.50 | 4.3 | 3.0 | (15) | 5.2 | No | 0.0 | 55 | Comparison |

[a]% by mass based on cellulose acetate 201 to 207 of Comparative Examples were measured at 25° C. and 60% RH. Then, change in the retardation was determined in accordance with the following formula (A):

Change in retardation(%)=(R*th*(548) before irradiation−R*th*(548) after irradiation)/R*th*(548) before irradiation×100      Formula (A)

Evaluation of Stain Formation Caused by Photo Irradiation

The films were observed with the naked eye so as to evaluate the presence or absence of film coloration caused by the photo irradiation

[Evaluation of Bleed-Out]

A piece (1 m×1 m) of each cellulose acylate film was cut out and bleed-out on the surface thereof was evaluated with the naked eye in accordance with the following criteria.
A: No bleed-out occurs.
B: Bleed-out occurs in an area less than 20%.
C: Bleed-out occurs in an area of 20% or more.
Table 2 summarizes the results.

TABLE 2

| Film no. | Rth (nm) | | | Bleed-out | Light-fastness | | Remarks |
| | Rth(446) | Rth(548) | Rth(628) | | Retardation change ratio | Stain | |
| --- | --- | --- | --- | --- | --- | --- | --- |
| 101 | 106 | 94 | 91 | A | 5% | No | Invention |
| 102 | 89 | 71 | 69 | A | 14% | No | Invention |
| 103 | 113 | 91 | 88 | A | 8% | No | Invention |
| 104 | 152 | 135 | 127 | A | 4% | No | Invention |
| 105 | 133 | 117 | 112 | A | 17% | No | Invention |
| 106 | 139 | 120 | 116 | A | 15% | No | Invention |
| 107 | 128 | 110 | 106 | A | 14% | No | Invention |
| 108 | 155 | 130 | 126 | A | 15% | No | Invention |
| 109 | 242 | 222 | 216 | B | 19% | No | Invention |
| 110 | 101 | 81 | 78 | B | 18% | No | Invention |
| 111 | 161 | 136 | 131 | B | 21% | No | Invention |
| 112 | 208 | 180 | 175 | A | 3% | No | Invention |
| 113 | 128 | 116 | 114 | B | 20% | No | Invention |
| 114 | 123 | 114 | 113 | B | 19% | No | Invention |
| 115 | 138 | 118 | 114 | B | 21% | No | Invention |
| 201 | 58 | 39 | 37 | A | 26% | No | Comparison |
| 202 | 63 | 44 | 40 | B | 16% | Yellow | Comparison |
| 203 | 98 | 105 | 110 | B | 1% | No | Comparison |
| 204 | 342 | 307 | 300 | A | 10% | No | Comparison |
| 205 | 45 | 30 | 28 | A | 15% | No | Comparison |
| 206 | 20 | 5 | 1 | A | 18% | No | Comparison |
| 207 | 70 | 55 | 53 | A | 14% | No | Comparison |

As Table 2 clearly shows, the films according to the invention showed Rth's satisfying the above formulae (1) and (2), small retardation changes and no coloration. In contrast thereto, the film 201 of Comparative Example showed a low Rth(548) and a large change in retardation. The film 202 showed not only a low Rth(548) but also yellowing in the film. The film 203 showed inverse dispersion (i.e., Rth(446)<Rth(548)<Rth(628)) and, therefore, failed to satisfy the formula (2). Moreover, the films 201, 202 and 204 to 207 showed retardation Rth(548)'s not satisfying the formula (1), which is unpreferable from the viewpoint of optical compensation.

Example 5

Production of Optically Compensatory Film 301

<Preparation of Cellulose Acylate Solution 21>

The following composition was fed into a mixing tank and stirred to dissolve the individual components, thereby preparing a cellulose acylate solution 21.

[Composition of Cellulose Acylate Solution 21]

| | |
| --- | --- |
| Cellulose acetate (acetyl substitution degree: 2.94, average degree of polymerization: 390) | 100.0 parts by mass |
| Triphenyl phosphate (plasticizer) | 8.0 parts by mass |
| Biphenyl phosphate (plasticizer) | 4.0 parts by mass |
| Methylene chloride (first solvent) | 402.0 parts by mass |
| Methanol (second solvent) | 60.0 parts by mass |

<Preparation of Matting Agent Solution 22>

The following composition was fed into a dispersing machine and stirred to dissolve the individual components, thereby preparing a matting agent solution 22.

[Composition of Matting Agent Solution 22]

| | |
| --- | --- |
| Silica particles (average particulate size: 20 nm, AEROSIL R972 manufactured by AEROSIL) | 2.0 parts by mass |
| Methylene chloride (first solvent) | 76.3 parts by mass |
| Methanol (second solvent) | 11.4 parts by mass |
| Cellulose acylate solution 21 | 10.3 parts by mass |

<Preparation of Retardation Developing Agent 23 Solution>

The following composition was fed into a mixing tank and stirred with heating to dissolve the individual components, thereby preparing a retardation developing agent solution 23.

[Composition of Retardation Developing Agent Solution 23]

| | |
| --- | --- |
| Retardation developing agent (C), see below | 9.0 parts by mass |
| Retardation developing agent (D), see below | 11.0 parts by mass |
| Methylene chloride (first solvent) | 67.2 parts by mass |

-continued

| Methanol (second solvent) | 10.0 parts by mass |
| Cellulose acylate solution 21 | 12.8 parts by mass |

Retardation developing agent (C)

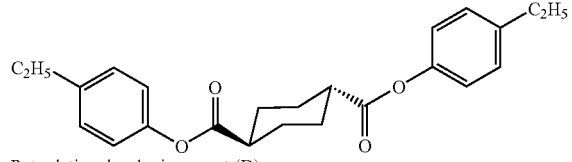

Retardation developing agent (D)

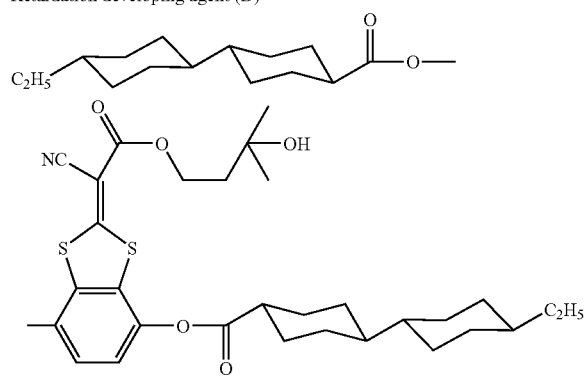

1.3 parts by mass of the matting agent solution 22 and 8.1 parts by mass of the retardation developing agent solution 23 were filtered and then mixed by using an in-line mixer. Further, 90.6 parts by mass of the cellulose acylate solution 21 was added thereto and mixed by using an in-line mixer. Next, the mixture was cast by using a band casting machine and dried. When the residual solvent content attained 35% by mass at 100° C., the film was peeled off from the band. Then, the film was held with tenter clips and laterally stretched at the stretching ratio of 22% at 150° C. Then, the clips were taken off and the film was dried at 130° C. for 40 minutes. Thus, an optionally compensatory film 301 was produced. The optionally compensatory film 301 thus produced had a residual solvent content of 0.1% by mass and a thickness of 80 μm. When measured with WR KOBRA, the retardation values thereof were as follows: Re(446)=88 nm, Re(548)=102 nm, Re(628) 107 nm, Rth(446)=106 nm, Rth(548)=122 nm and Rth(629) 131 nm.

Example 6

Saponification Treatment of Normal Wavelength Dispersion Film 101

The normal wavelength dispersion film 101 produced above was dipped in a 2.3 mol/L, aqueous solution of sodium hydroxide at 55° C. for 3 minutes, washed in a water washing bath at room temperature and then neutralized with 0.05 mol/L sulfuric acid at 30° C. Next, it was washed again in a water washing bath at room temperature and dried in a hot air stream at 100° C. Thus, the surface of the normal wavelength dispersion film 101 was saponified.

(Saponification Treatment of Optically Compensatory Film 301)

The surface of the optically compensatory film 301 was saponified in the same manner as in the saponification treatment of the normal wavelength dispersion film 101.

Example 7

Production of Polarizing Plate 101

(Saponification Treatment of Polarizing Plate Protective Film)

A commercially available cellulose acetate film (FUJITAC TD80, manufactured by Fuji Photo Film Co., Ltd.) was dipped in a 1.5 mol/L aqueous solution of sodium hydroxide at 55° C. for 1 minute, washed in a water washing bath at room temperature and then neutralized with 0.05 mol/L sulfuric acid at 30° C. Next, it was washed again in a water washing bath at room temperature and dried in a hot air stream at 100° C.

(Production of Polarizer)

To a stretched polyvinyl alcohol film, iodine was adsorbed to form a polarizer. On one side of the polarizer, the normal wavelength dispersion film 101 having been saponified as described above was bonded with a polyvinyl alcohol-based adhesive as a polarizing plate protective film in such a manner that the absorption axis of the polarizer and the slow axis of the cellulose acylate film were arranged in parallel to each other.

Further, the commercially available cellulose triacetate film having been saponified as described above was bonded on the other side with a polyvinyl alcohol-based adhesive. Thus, a polarizing plate 101 was constructed.

Example 8

Production of Polarizing Plates 102 to 115

Polarizing plates 102 to 115 were produced by respectively using the normal dispersion films 102 to 115 by the same method as in Example 7.

Comparative Example 3

Production of Polarizing Plates 201 to 207

Polarizing plates 201 to 207 were produced by respectively using the cellulose acylate films 201 to 207 by the same method as in Example 7.

Example 9

Production of Polarizing Plate 301

Also, a polarizing plate 301 was also produced as in Example 7 by using the optically compensatory film 301.

Example 10

Production of Liquid Crystal Display Devices A to V

In FIG. 1, a VA mode liquid crystal cell was equipped with the polarizing plate 101 as the upper polarizing plate 1 in FIG. 1 so that the normal wavelength dispersion film 101 according to the invention was located on the liquid crystal cell side, and with the polarizing plate 301 as the lower polarizing plate 12 so that the optically compensatory film 301 was located on the liquid crystal cell side, respectively on the viewer side and the backlight side with the use of an adhesive. These polarizing plates were arranged in cross-Nicol position so that the transmission axis of the viewer side polarizing plate was located in the vertical direction while the transmission axis of the backlight side polarizing plate was located in the horizontal direction. Thus, a liquid crystal display device A was constructed Liquid crystal display devices B to V were produced by respectively using the polarizing plates listed in Table 3 as a substitute for the polarizing plate in the liquid crystal display device A.

[Evaluation of Liquid Crystal Display Device]
(Evaluation of Viewing Angle of Tint of Panel)

In each of the VA mode liquid crystal display devices A to V having been produced by the methods as described above, a backlight was provided in the polarizing plate 12 side in FIG. 1. Using a tester (EZ-Contrast XL88, manufactured by ELDIM Co.), the oblique contrast was calculated from the brightness at white level/the brightness at black level at a polar angle 60° in the center line direction (azimuthal angle 45°) of the transmission axis of a pair of polarizing plates from the normal direction of the liquid crystal cell at the time of black level. Evaluation was made in accordance with the following criteria.

A: 60≦oblique contrast.
B: 45≦oblique contrast<60
C: oblique contrast<45.

Further, tint change between azimuthal angles 0° and 80° at the polar angle 60° was observed with the naked eye.

Table 3 shows the results.

Table 3 indicates that the liquid crystal display devices A to O respectively using the normal dispersion films 101 to 115 according to the invention are preferred to the liquid crystal display devices P to Q and S to V respectively using the comparative samples 201 to 202 and 204 to 207, because of having been improved in oblique contrast. It can be also understood that the products according to the invention are preferable to the polarizing plate R using the comparative sample 203, because of having been improved in tint change.

According to the present invention, it is possible to provide a liquid crystal display device which has a high oblique contrast, a low dependency on viewing angle of tint and an excellent light-fastness and in which the occurrence of bleed-out is regulated.

The entire disclosure of each and every foreign patent application from which the benefit of foreign priority has been claimed in the present application is incorporated herein by reference, as if fully set forth.

What is claimed is:
1. A polymer film, comprising:
a wavelength dispersion regulator represented by formula (I):

TABLE 3

| Liquid crystal display device | Polarizing plate in viewer's side | Phase difference film in backlight side | Oblique contrast | Change in tint | Remarks |
|---|---|---|---|---|---|
| A | Polarizing plate 101 | Polarizing plate 301 | B | Small | Invention |
| B | Polarizing plate 102 | Polarizing plate 301 | B | Small | Invention |
| C | Polarizing plate 103 | Polarizing plate 301 | B | Small | Invention |
| D | Polarizing plate 104 | Polarizing plate 301 | A | Small | Invention |
| E | Polarizing plate 105 | Polarizing plate 301 | A | Small | Invention |
| F | Polarizing plate 106 | Polarizing plate 301 | A | Small | Invention |
| G | Polarizing plate 107 | Polarizing plate 301 | A | Small | Invention |
| H | Polarizing plate 108 | Polarizing plate 301 | A | Small | Invention |
| I | Polarizing plate 109 | Polarizing plate 301 | B | Small | Invention |
| J | Polarizing plate 110 | Polarizing plate 301 | B | Small | Invention |
| K | Polarizing plate 111 | Polarizing plate 301 | A | Small | Invention |
| L | Polarizing plate 112 | Polarizing plate 301 | A | Small | Invention |
| M | Polarizing plate 113 | Polarizing plate 301 | A | Small | Invention |
| N | Polarizing plate 114 | Polarizing plate 301 | A | Small | Invention |
| O | Polarizing plate 115 | Polarizing plate 301 | A | Small | Invention |
| P | Polarizing plate 201 | Polarizing plate 301 | C | Small | Comparison |
| Q | Polarizing plate 202 | Polarizing plate 301 | C | Small | Comparison |
| R | Polarizing plate 203 | Polarizing plate 301 | B | Large | Comparison |
| S | Polarizing plate 204 | Polarizing plate 301 | C | Small | Comparison |
| T | Polarizing plate 205 | Polarizing plate 301 | C | Small | Comparison |
| U | Polarizing plate 206 | Polarizing plate 301 | C | Small | Comparison |
| V | Polarizing plate 207 | Polarizing plate 301 | C | Small | Comparison |

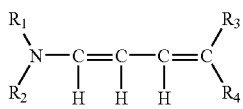

Formula (I)

wherein $R_1$ and $R_2$ each independently represents a hydrogen atom, an alkyl group or an aryl group, provided that both $R_1$ and $R_2$ are not hydrogen atoms at the same time; and $R_3$ and $R_4$ each independently represents an electron-withdrawing substituent, and $R_1$ and $R_2$, or $R_3$ and $R_4$ may be bonded together to form a ring, and wherein the polymer film has a retardation value that satisfies the following formulae (1) and (2):

$$70 \text{ nm} \leq Rth(548) \leq 300 \text{ nm} \qquad \text{Formula (1)}$$

$$Rth(628) < Rth(548) < Rth(446) \qquad \text{Formula (2)}$$

wherein $Rth(\lambda)$ represents a retardation value expressed in nm in a film thickness direction measured at a wavelength of $\lambda$ nm, and wherein the polymer film further comprises a light-fastness improving agent represented by formula (II):

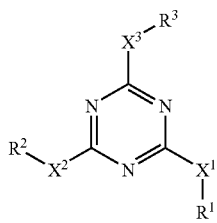

Formula (II)

wherein $X^1$ represents —$NR^4$—, —O— or —S—;
$X^2$ represents —$NR^5$—, —O— or —S—;
$X^3$ represents —$NR^6$—, —O— or —S—;
$R^1$, $R^2$ and $R^3$ each independently represents an alkyl group, an alkenyl group, an aryl group or a heterocyclic group; and
$R^4$, $R^5$ and $R^6$ each independently represents a hydrogen atom, an alkyl group, an alkenyl group, an aryl group or a heterocyclic group.

2. The polymer film according to claim 1, comprising: a cellulose acylate.

3. The polymer film according to claim 2,
wherein the cellulose acylate contains acetyl groups and propionyl groups, and
when a substitution degree of acetyl groups is A and a substitution degree of propionyl groups is P, the acetyl substitution degree A and the propionyl substitution degree P satisfy the following formulae (3) and (4):

$$2.00 \leq A+P \leq 2.70 \qquad \text{Formula (3)}$$

$$(3-A-P) \times 0.5 \leq P \leq (3-A-P) \times 2 \qquad \text{Formula (4).}$$

4. The polymer film according to claim 2, which contains 1.0 to 20% by mass of the wavelength dispersion regulator represented by formula (I) based on the cellulose acylate.

5. The polymer film according to claim 1, which contains 10% by mass or more but not more than 1000% by mass of the light-fastness improving agent represented by formula (II) based on the wavelength dispersion regulator represented by formula (I).

6. The polymer film according to claim 1,
wherein the wavelength dispersion regulator represented by formula (I) is a compound represented by formula (I-2):

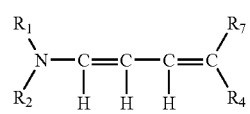

Formula (I-2)

wherein $R_1$, $R_2$ and $R_4$ are each as defined in formula (I); and
$R_7$ represents —$COOR_5$ or —$SO_2R_5$, in which $R_5$ represents a hydrogen atom or a substituent.

7. A polarizing plate protective film, comprising: the polymer film according to claim 1.

8. A polarizing plate, comprising:
a polarizer; and
a protective film that is provided in at least one side of the polarizer,
wherein the protective film is the polarizing plate protective film according to claim 7.

9. A liquid crystal display device, comprising:
a liquid crystal cell; and
the polarizing plate according to claim 8.

* * * * *